(12) United States Patent
Kannan et al.

(10) Patent No.: US 11,066,675 B2
(45) Date of Patent: *Jul. 20, 2021

(54) INCREASED NUCLEIC-ACID GUIDED CELL EDITING IN YEAST

(71) Applicant: Inscripta, Inc., Boulder, CO (US)

(72) Inventors: Krishna Kannan, Boulder, CO (US); Miles Gander, Boulder, CO (US); Eileen Spindler, Boulder, CO (US); Paul Hardenbol, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/140,056

(22) Filed: Jan. 2, 2021

(65) Prior Publication Data

US 2021/0130834 A1    May 6, 2021

Related U.S. Application Data

(63) Continuation of application No. 16/904,405, filed on Jun. 17, 2020, now Pat. No. 10,927,385.

(60) Provisional application No. 62/866,041, filed on Jun. 25, 2019.

(51) Int. Cl.
 *C12N 15/80* (2006.01)
 *C12N 15/10* (2006.01)

(52) U.S. Cl.
 CPC ......... *C12N 15/80* (2013.01); *C12N 15/1058* (2013.01)

(58) Field of Classification Search
 None
 See application file for complete search history.

(56) References Cited

U.S. PATENT DOCUMENTS

| | | | |
|---|---|---|---|
| 4,833,080 A | 5/1989 | Brent et al. |
| 4,959,317 A | 9/1990 | Sauer et al. |
| 5,464,764 A | 11/1995 | Capecchi et al. |
| 5,487,992 A | 1/1996 | Capecchi et al. |
| 5,627,059 A | 5/1997 | Capecchi et al. |
| 5,631,153 A | 5/1997 | Capecchi et al. |
| 5,654,182 A | 8/1997 | Wahl et al. |
| 5,677,177 A | 10/1997 | Wahl et al. |
| 5,710,381 A | 1/1998 | Atwood et al. |
| 5,792,943 A | 8/1998 | Craig |
| 5,885,836 A | 3/1999 | Wahl et al. |
| 5,888,732 A | 3/1999 | Hartley et al. |
| 6,074,605 A | 6/2000 | Meserol et al. |
| 6,127,141 A | 10/2000 | Kopf |
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,391,582 B2 | 5/2002 | Ying et al. |
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,926,977 B2 | 1/2015 | Miller et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,260,505 B2 | 2/2016 | Weir et al. |

(Continued)

FOREIGN PATENT DOCUMENTS

| | | |
|---|---|---|
| CN | 2397122 Y | 9/2000 |
| EP | 2135626 A1 | 12/2009 |

(Continued)

OTHER PUBLICATIONS

Yoshioka, et al., "Development for a mono-promoter-driven CRISPR/CAS9 system in mammalian cells", Scientific Reports, Jul. 3, 2015, p. 1-8.
Remaut, et al., "Plasmid vectors for high-efficiency expression controlled by the PL promoter of coliphage lambda", Laboratory of Molecular Biology, Apr. 15, 1981, p. 81-93.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.
International Search Report and Written Opinion for International Application No. PCT/US19/46526, dated Dec. 18, 2019, p. 1-17.
International Search Report and Written Opinion for International Application No. PCT/US18/34779, dated Nov. 26, 2018, p. 1-39.

(Continued)

*Primary Examiner* — Nancy J Leith
(74) *Attorney, Agent, or Firm* — Sarah Brashears; Dianna L. DeVore

(57) ABSTRACT

The present disclosure provides methods to increase the percentage of edited yeast cells in a cell population using nucleic-acid guided editing, and automated multi-module instruments for performing these methods.

15 Claims, 30 Drawing Sheets

Specification includes a Sequence Listing.

(56) References Cited

U.S. PATENT DOCUMENTS

| | | |
|---|---|---|
| 9,361,427 B2 | 6/2016 | Hillson |
| 9,499,855 B2 | 11/2016 | Hyde et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,266,851 B2 | 4/2019 | Chen |
| 10,927,385 B2* | 2/2021 | Kannan ............... C12N 15/102 |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0110253 A1 | 6/2004 | Kappler et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0002812 A1 | 1/2011 | Asogawa et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0273226 A1 | 9/2014 | Wu et al. |
| 2014/0350456 A1 | 11/2014 | Caccia |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0297887 A1 | 10/2015 | Dhillon et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0281053 A1 | 9/2016 | Sorek et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0313306 A1 | 10/2016 | Ingber et al. |
| 2016/0354487 A1 | 12/2016 | Zhang et al. |
| 2016/0367991 A1 | 12/2016 | Cepheid |
| 2017/0002339 A1 | 1/2017 | Barrangou et al. |
| 2017/0022499 A1 | 1/2017 | Lu et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0218355 A1 | 3/2017 | Buie et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2017/0369870 A1 | 12/2017 | Gill et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0142196 A1 | 5/2018 | Coppeta et al. |
| 2018/0155665 A1 | 6/2018 | Zenhausern et al. |
| 2018/0169148 A1 | 6/2018 | Adair et al. |
| 2018/0179485 A1 | 6/2018 | Borenstein et al. |
| 2018/0200342 A1 | 7/2018 | Bikard et al. |
| 2018/0230460 A1 | 8/2018 | Gill et al. |
| 2019/0017072 A1 | 1/2019 | Ditommaso et al. |
| 2019/0169605 A1 | 6/2019 | Masquelier et al. |

FOREIGN PATENT DOCUMENTS

| | | |
|---|---|---|
| EP | 2240238 | 10/2010 |
| EP | 2395087 | 12/2011 |
| EP | 3030652 | 6/2016 |
| EP | 1766004 | 8/2016 |
| EP | 3199632 | 8/2017 |
| EP | 2459696 | 11/2017 |
| WO | WO 2003/057819 | 7/2001 |
| WO | WO2002/010183 | 2/2002 |
| WO | WO 2003/087341 | 10/2003 |
| WO | WO 2009/091578 | 7/2009 |
| WO | WO 2010/079430 | 7/2010 |
| WO | WO 2011/072246 | 6/2011 |
| WO | WO2011/143124 | 11/2011 |
| WO | WO 2012/012779 A3 | 1/2012 |
| WO | WO2013/142578 | 9/2013 |
| WO | WO 2013/176772 | 11/2013 |
| WO | WO2014/018423 | 1/2014 |
| WO | WO2014/144495 | 9/2014 |
| WO | WO 2015/021270 | 2/2015 |
| WO | WO 2016/003485 | 1/2016 |
| WO | WO 2016/054939 | 4/2016 |
| WO | WO2016/110453 | 7/2016 |
| WO | WO 2016/145290 | 9/2016 |
| WO | WO2017/053902 | 3/2017 |
| WO | WO 2017/078631 | 5/2017 |
| WO | WO2017/083722 | 5/2017 |
| WO | WO2017/106414 | 6/2017 |
| WO | WO2017/161371 | 9/2017 |
| WO | WO2017/174329 | 10/2017 |
| WO | WO2017/186718 | 11/2017 |
| WO | WO2017/216392 | 12/2017 |
| WO | WO2017/223330 | 12/2017 |
| WO | WO 2018/015544 | 1/2018 |
| WO | WO2018/031950 | 2/2018 |
| WO | WO2018/071672 | 4/2018 |
| WO | WO2018/083339 | 5/2018 |
| WO | WI 2018/191715 | 10/2018 |
| WO | WO2019/006436 | 1/2019 |

OTHER PUBLICATIONS

International Search Report and Written Opinion for International Application No. PCT/US19/57250, dated Feb. 25, 2020, p. 1-16.
International Search Report and Written Opinion for International Application No. PCT/US20/24341, dated Jun. 19, 2020, p. 1-9.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.

(56) References Cited

OTHER PUBLICATIONS

Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Eklund, et al., "Altered target site specificity variants of the I-Ppol His-Cys bis homing endonuclease" Nucleic Acids Research, 35(17):5839-50 (2007).
Garst, et al., "Genome-wide mapping of mutations at single-nucleotide resolution for protein, metabolic and genome engineering", Nature Biotechnology, 35(1):48-59 (2017).
Boles, et al., "Digital-to-biological converter for on-demand production of biologics", Nature Biotechnology, doi:10.1038/nbt.3859 (May 29, 2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Pines, et al., "Codon Compression Algorithms for Saturation Mutagenesis", ACS Synthetic Biology, 4:604-14 (2015).
Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).

Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962, 2003.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Lefevre et al., "Alanine-stretch scanning mutagenesis: a simple and efficient method to probe protein structure and function," Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
International Search Report and Written Opinion for International Application No. PCT/US2018/040519, dated Sep. 26, 2018, p. 1-8.
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.

(56) References Cited

OTHER PUBLICATIONS

International Search Report and Written Opinion for International Application No. PCT/US2019/023342 dated Jun. 6, 2019, p. 1-12.
International Search Report and Written Opinion for International Application No. PCT/US2019/026836 dated Jul. 2, 2019, p. 1-10.
International Search Report and Written Opinion for International Application No. PCT/US2019/028821 dated Aug. 2, 2019, p. 1-14.
International Search Report and Written Opinion for Interational Application No. PCT/US2019/028883 dated Aug. 16, 2019, p. 1-12.
International Search Report and Written Opinion for International Application No. PCT/US2019/030085 dated Jul. 23, 2019, p. 1-14.
NonFinal Office Action for U.S. Appl. No. 16/024,816 dated Sep. 4, 2018, p. 1-10.
1Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
First Office Action Interview Pilot Program Pre-Interview Communication for U.S. Appl. No. 16/360,404 dated Jul. 1, 2019, p. 1-27.
First Office Action Interview Pilot Program Pre Interview Communication for U.S. Appl. No. 16/360,423 dated Jul. 1, 2019, p. 1-27.
Non Final Office Action for U.S. Appl. No. 16/399,988 dated Jul. 31, 2019, p. 1-20.
First Office Action Interview Pilot Program Pre-Interview Communication for U.S. Appl. No. 16/454,865 dated Aug. 16, 2019, p. 1-36.

\* cited by examiner

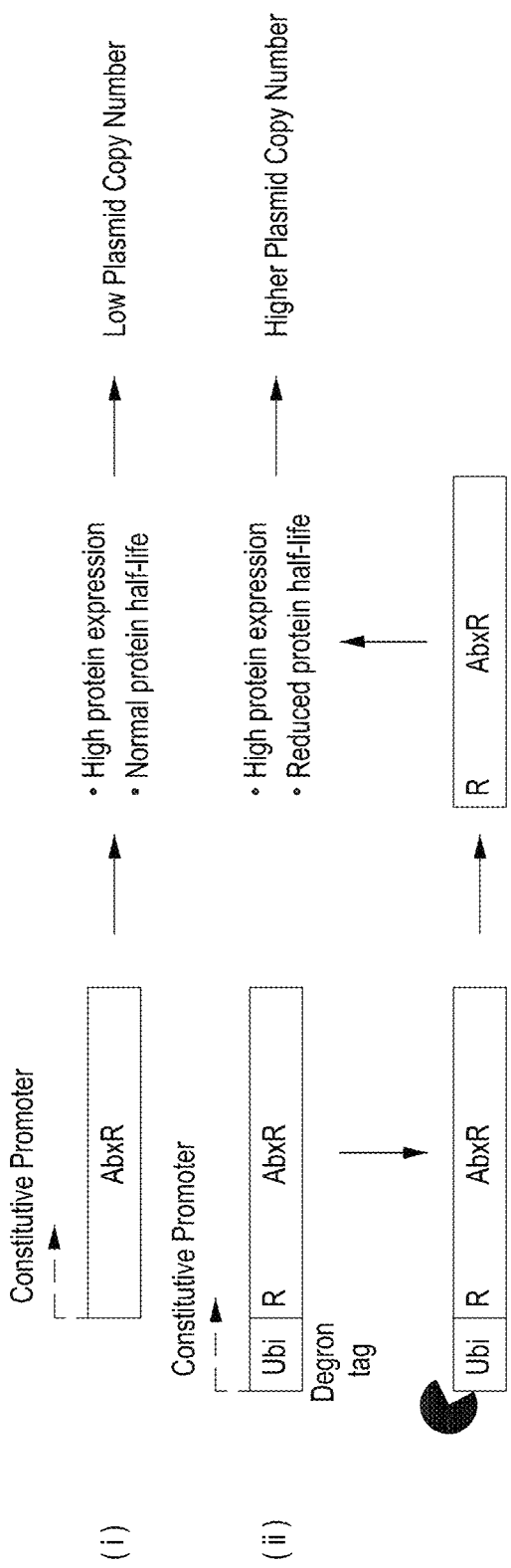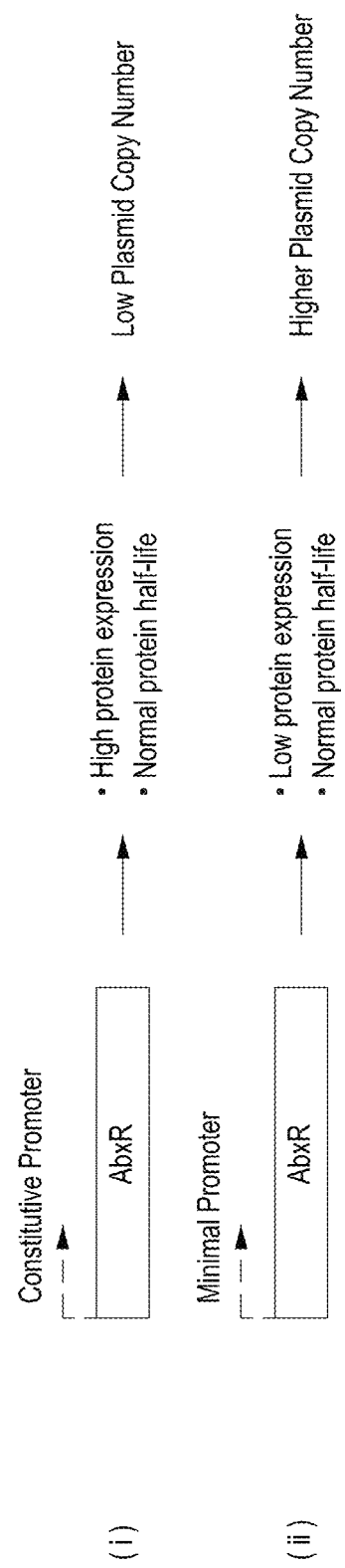

```
                       SEQUENCE LISTING

<160> NUMBER OF SEQ ID NOS: 30

<210> SEQ ID NO 1
<211> LENGTH: 47
<212> TYPE: DNA
<213> ORGANISM: Artificial Sequence
<220> FEATURE:
<223> OTHER INFORMATION: Truncated promoter

<400> SEQUENCE: 1
taacccaact gcacagaaca aaaacctgca ggaaacgaag ataaatc               47

<210> SEQ ID NO 2
<211> LENGTH: 100
<212> TYPE: DNA
<213> ORGANISM: Artificial Sequence
<220> FEATURE:
<223> OTHER INFORMATION: TRUNCATED PROMOTER SEQUENCE

<400> SEQUENCE: 2
attggcatta tcacataatg aattatacat tatataaagt aatgtgattt cttcgaagaa   60
tatactaaaa aatgagcagg caagataaac gaaggcaaag                       100

<210> SEQ ID NO 3
<211> LENGTH: 50
<212> TYPE: DNA
<213> ORGANISM: Artificial Sequence
<220> FEATURE:
<223> OTHER INFORMATION: TRUNCATED PROMOTER SEQUENCE

<400> SEQUENCE: 3
cttcgaagaa tatactaaaa aatgagcagg caagataaac gaaggcaaag             50

<210> SEQ ID NO 4
<211> LENGTH: 30
<212> TYPE: DNA
<213> ORGANISM: Artificial Sequence
<220> FEATURE:
<223> OTHER INFORMATION: AATGAGCAGGCAAGATAAACGAAGGCAAAG

<400> SEQUENCE: 4
aatgagcagg caagataaac gaaggcaaag                                   30

<210> SEQ ID NO 5
<211> LENGTH: 20
<212> TYPE: DNA
<213> ORGANISM: Artificial Sequence
<220> FEATURE:
<223> OTHER INFORMATION: TRUNCATED PROMOTER SEQUENCE

<400> SEQUENCE: 5
caagataaac gaaggcaaag                                              20

<210> SEQ ID NO 6
<211> LENGTH: 100
<212> TYPE: DNA
<213> ORGANISM: Artificial Sequence
<220> FEATURE:
<223> OTHER INFORMATION: TRUNCATED PROMOTER SEQUENCE

<400> SEQUENCE: 6
```

-continued

```
ttcggtcgaa aaaagaaaag gagagggcca agagggaggg cattggtgac tattgagcac    60
gtgagtatac gtgattaagc acacaaaggc agcttggagt                         100
```

<210> SEQ ID NO 7
<211> LENGTH: 50
<212> TYPE: DNA
<213> ORGANISM: Artificial Sequence
<220> FEATURE:
<223> OTHER INFORMATION: TRUNCATED PROMOTER SEQUENCE

<400> SEQUENCE: 7

```
tattgagcac gtgagtatac gtgattaagc acacaaaggc agcttggagt               50
```

<210> SEQ ID NO 8
<211> LENGTH: 30
<212> TYPE: DNA
<213> ORGANISM: Artificial Sequence
<220> FEATURE:
<223> OTHER INFORMATION: TRUNCATED PROMOTER SEQUENCE

<400> SEQUENCE: 8

```
gtgattaagc acacaaaggc agcttggagt                                     30
```

<210> SEQ ID NO 9
<211> LENGTH: 20
<212> TYPE: DNA
<213> ORGANISM: Artificial Sequence
<220> FEATURE:
<223> OTHER INFORMATION: TRUNCATED PROMOTER SEQUENCE

<400> SEQUENCE: 9

```
acacaaaggc agcttggagt                                                20
```

<210> SEQ ID NO 10
<211> LENGTH: 100
<212> TYPE: DNA
<213> ORGANISM: Artificial Sequence
<220> FEATURE:
<223> OTHER INFORMATION: TRUNCATED PROMOTER SEQUENCE

<400> SEQUENCE: 10

```
ttttccaata ggtggttagc aatcgtctta ctttctaact tttcttacct tttacatttc    60
agcaatatat atatatatat ttcaaggata taccattcta                         100
```

<210> SEQ ID NO 11
<211> LENGTH: 50
<212> TYPE: DNA
<213> ORGANISM: Artificial Sequence
<220> FEATURE:
<223> OTHER INFORMATION: TRUNCATED PROMOTER SEQUENCE

<400> SEQUENCE: 11

```
tttacatttc agcaatatat atatatatat ttcaaggata taccattcta               50
```

<210> SEQ ID NO 12
<211> LENGTH: 30
<212> TYPE: DNA
<213> ORGANISM: Artificial Sequence
<220> FEATURE:
<223> OTHER INFORMATION: TRUNCATED PROMOTER SEQUENCE

<400> SEQUENCE: 12

```
atatatatat ttcaaggata taccattcta                                     30
```

<210> SEQ ID NO 13
<211> LENGTH: 20
<212> TYPE: DNA
<213> ORGANISM: Artificial Sequence
<220> FEATURE:
<223> OTHER INFORMATION: TRUNCATED PROMOTER SEQUENCE

<400> SEQUENCE: 13
ttcaaggata taccattcta                                               20

<210> SEQ ID NO 14
<211> LENGTH: 100
<212> TYPE: DNA
<213> ORGANISM: Artificial Sequence
<220> FEATURE:
<223> OTHER INFORMATION: TRUNCATED PROMOTER SEQUENCE

<400> SEQUENCE: 14
ggtatatata cgcatatgtg gtgttgaaga aacatgaaat tgcccagtat tcttaaccca   60
actgcacaga acaaaaacct gcaggaaacg aagataaatc                        100

<210> SEQ ID NO 15
<211> LENGTH: 50
<212> TYPE: DNA
<213> ORGANISM: Artificial Sequence
<220> FEATURE:
<223> OTHER INFORMATION: TRUNCATED PROMOTER SEQUENCE

<400> SEQUENCE: 15
tcttaaccca actgcacaga acaaaaacct gcaggaaacg aagataaatc              50

<210> SEQ ID NO 16
<211> LENGTH: 30
<212> TYPE: DNA
<213> ORGANISM: Artificial Sequence
<220> FEATURE:
<223> OTHER INFORMATION: TRUNCATED PROMOTER SEQUENCE

<400> SEQUENCE: 16
acaaaaacct gcaggaaacg aagataaatc                                    30

<210> SEQ ID NO 17
<211> LENGTH: 20
<212> TYPE: DNA
<213> ORGANISM: Artificial Sequence
<220> FEATURE:
<223> OTHER INFORMATION: TRUNCATED PROMOTER SEQUENCE

<400> SEQUENCE: 17
gcaggaaacg aagataaatc                                               20

<210> SEQ ID NO 18
<211> LENGTH: 100
<212> TYPE: DNA
<213> ORGANISM: Artificial Sequence
<220> FEATURE:
<223> OTHER INFORMATION: TRUNCATED PROMOTER SEQUENCE

<400> SEQUENCE: 18
tcaagtttca gtttcatttt tcttgttcta ttacaacttt ttttacttct tgctcattag   60
aaagaaagca tagcaatcta atctaagttt taattacaaa                        100

<210> SEQ ID NO 19
<211> LENGTH: 50

```
<212> TYPE: DNA
<213> ORGANISM: Artificial Sequence
<220> FEATURE:
<223> OTHER INFORMATION: TRUNCATED PROMOTER SEQUENCE

<400> SEQUENCE: 19
tgctcattag aaagaaagca tagcaatcta atctaagttt taattacaaa              50

<210> SEQ ID NO 20
<211> LENGTH: 30
<212> TYPE: DNA
<213> ORGANISM: Artificial Sequence
<220> FEATURE:
<223> OTHER INFORMATION: TRUNCATED PROMOTER SEQUENCE

<400> SEQUENCE: 20
tagcaatcta atctaagttt taattacaaa                                    30

<210> SEQ ID NO 21
<211> LENGTH: 20
<212> TYPE: DNA
<213> ORGANISM: Artificial Sequence
<220> FEATURE:
<223> OTHER INFORMATION: TRUNCATED PROMOTER SEQUENCE

<400> SEQUENCE: 21
atctaagttt taattacaaa                                               20

<210> SEQ ID NO 22
<211> LENGTH: 100
<212> TYPE: DNA
<213> ORGANISM: Artificial Sequence
<220> FEATURE:
<223> OTHER INFORMATION: TRUNCATED PROMOTER SEQUENCE

<400> SEQUENCE: 22
taaaataata aaacatcaag aacaaacaag ctcaacttgt cttttctaag aacaaagaat   60
aaacacaaaa acaaaaagtt tttttaattt taatcaaaaa                        100

<210> SEQ ID NO 23
<211> LENGTH: 50
<212> TYPE: DNA
<213> ORGANISM: Artificial Sequence
<220> FEATURE:
<223> OTHER INFORMATION: TRUNCATED PROMOTER SEQUENCE

<400> SEQUENCE: 23
aacaaagaat aaacacaaaa acaaaaagtt tttttaattt taatcaaaaa              50

<210> SEQ ID NO 24
<211> LENGTH: 30
<212> TYPE: DNA
<213> ORGANISM: Artificial Sequence
<220> FEATURE:
<223> OTHER INFORMATION: TRUNCATED PROMOTER SEQUENCE

<400> SEQUENCE: 24
acaaaaagtt tttttaattt taatcaaaaa                                    30

<210> SEQ ID NO 25
<211> LENGTH: 20
<212> TYPE: DNA
<213> ORGANISM: Artificial Sequence
<220> FEATURE:
<223> OTHER INFORMATION: TRUNCATED PROMOTER SEQUENCE
```

<400> SEQUENCE: 25 ttttaattt taatcaaaaa                                          20

<210> SEQ ID NO 26
<211> LENGTH: 566
<212> TYPE: DNA
<213> ORGANISM: Artificial Sequence
<220> FEATURE:
<223> OTHER INFORMATION: WEAK PROMOTER SEQUENCE

<400> SEQUENCE: 26
tcgacaaatt gttacgttgt gctttgattt ctaaagcgct tcttcacctg caggttctga      60
gccctaagaa aaaaatttc cttggttgaa atggcggaa aaaaaaaatt cagaaaaga       120 aataaagcac gtgtgcgcgg tgtgtggatg atggtttcat cattgtcaac ggcattttcg     180
ttcttgtgga ttgttgtaaa ctttccagaa cattctagaa agaaagcaca cggaacgttt     240
agaagctgtc atttgcgttt tttctccaga ttttagttga gaaagtaatt aaattattct    300
tcttttccca gaacgttcca tcggcggcaa aaggagaga agaacccaa aaagaagggg     360 ggccatttag attagctgat cgtttcgagg acttcaaggt tatataaggg gtggattgat     420
gtatcttcga gaagggattg agttgtagtt tcgtttccca attcttactt aagttgtttt    480
attttctcta tttgtaagat aagcacatca aagaaaagt aatcaagtat tacaagaaac     540
aaaaattcaa gtaaataaca gataat                                           566

<210> SEQ ID NO 27
<211> LENGTH: 654
<212> TYPE: DNA
<213> ORGANISM: Artificial Sequence
<220> FEATURE:
<223> OTHER INFORMATION: WEAK PROMOTER SEQUENCE

<400> SEQUENCE: 27
gaaattcaaa actctccaga caaagcctgc catttggcca agcaagcttt tgacgacgct      60
attgctgagt tggacactct gtctgaagaa tcatacaaag atagcacact tatcatgcaa     120
ctgctaaggg acaatttaac cttatggact tcagacatgt ccgagtccgg tcaagctgaa     180
gaccaacaac aacaacaaca acatcagcaa cagcagccac ctgctgccgc cgaaggtgaa     240
gcaccaaagt aagtattctg ataaatctaa agagaaatta ctaaaaaaaa gaaaaaaaaa     300
agaacggggg tgtaataatt tgtagttcat tattgcaatt atatatctat atctatatat     360
gtatataaca ttaacatgtg catgtacaca cgtaatcgcg cgtgtacatg tctatatgtg     420
ttacttgaac tatactgttt tgacgtgtat gtttatttat ctctcttctg attcctccac     480
cccttcctta ctcaaccggg taaatgtcgc atcatgactc ccgacaataa tcccctctgg    540
tatagcgaga agcaacttta gcttcttaac ggcaagaact ttttatgtt tgtcgcacct     600 gtatcttcac aaaagttgga tacagcaata agaaaggaaa ccacatttgt gcca          654

<210> SEQ ID NO 28
<211> LENGTH: 600
<212> TYPE: DNA
<213> ORGANISM: Artificial Sequence
<220> FEATURE:
<223> OTHER INFORMATION: WEAK PROMOTER SEQUENCE

<400> SEQUENCE: 28
agaaagatgt caactgaaaa aaaaaaggt gaacacagga aaaaaataa aaaaaaaaa       60 aaaaaagga ggacgaaaca aaaaagtgaa aaaaaatgaa aatttttttg gaaaaccaag   120

```
aaatgaatta tatttccgtg tgagacgaca tcgtcgaata tgattcaggg taacagtatt      180
gatgtaatca atttcctacc tgaatctaaa attcccggga gcaagatcaa gatgttttca      240
ccgatctttc cggtctcttt ggccggggtt tacggacgat ggcagaagac caaagcgcca      300
gttcatttgg cgagcgttgg ttggtggatc aagcccacgc gtaggcaatc ctcgagcaga      360
tccgccaggc gtgtatatat agcgtggatg gccaggcaac tttagtgctg acacatacag      420
gcatatatat atgtgtgcga cgacacatga tcatatggca tgcatgtgct ctgtatgtat      480
ataaaactct tgtttcttc ttttctctaa atattctttc cttatacatt aggacctttg       540
cagcataaat tactatactt ctatagacac acaaacacaa atacacacac taaattaata      600

<210> SEQ ID NO 29
<211> LENGTH: 600
<212> TYPE: DNA
<213> ORGANISM: Artificial Sequence
<220> FEATURE:
<223> OTHER INFORMATION: WEAK PROMOTER SEQUENCE

<400> SEQUENCE: 29
aacccggtct cgaagaacat cagcaccacg cccgcaacga caaagaacat tgcaatacac       60
ttgcatatgt gagcatagtc gagcggtccg ttctgtggtt gatgctgttg ttcttttcttc    120 tgtttgtcag gggtgatagc catatcttcg tgctcttgtt gcgattgttc tgttccatct     180
gcaccagaac aaagaacaaa agaacaagga acaaagtcca agcacgtcag cgctgtttat    240
aaggggattg acgagggatc gggcctagag tgccagcgcg ccaggagag ggagcccct      300 gggccctcat ccgcaggctg ataggggtca ccccgctggg caggtcaggg caggggctct    360
caggggggcg ccatggacaa actgcactga ggttctaaga cacatgtatt attgtgagta    420
tgtatatata gagagagatt aaggcgtaca gccgggtggt agagattgat taacttggta    480
gtcttatctt gtcaattgag tttctgtcag tttcttcttg aacaagcacg cagctaagta   540
agcaacaaag caggctaaca aactaggtac tcacatacag acttattaag acatagaact   600

<210> SEQ ID NO 30
<211> LENGTH: 500
<212> TYPE: DNA
<213> ORGANISM: Artificial Sequence
<220> FEATURE:
<223> OTHER INFORMATION: WEAK PROMOTER SEQUENCE

<400> SEQUENCE: 30
cagaggagta cacacgggac ttgatcgaac agatcgtgtt acagttgcgc tcgcaaagaa       60
tgaaaatggt tcagacaaag gatcagttcc tatttatcta ccatgctgcc aagtatctta     120
acagtctttc cgtgaaccaa tagacagcta tataaaagtt cctaattgtg catttttca     180 ataacaatac ttattcatcc ttataattat attctagctt cgttgtcatg ggaacatagc   240
ccatacaccg cagttattta tgatcatttc gaacgggaag tatggatgaa tctttttttt   300
ttttttttta tagcacgcaa ctgaaaaaaa aaaaagaaa aatttttcat cttcgctcga    360
cgtttctttt gtagtactca tctctttta tataaagatt aattagttat tgtcgctttg    420
cttttccttc tttaaaaaat gtttcttgct tttggatttt cagatgtccc aagatcatta   480
cagtatttta attgaacaaa                                                500
```

INCREASED NUCLEIC-ACID GUIDED CELL EDITING IN YEAST

RELATED CASES

This application is a continuation of U.S. Ser. No. 16/904, 405, filed 17 Jun. 2020, entitled "Increased Nucleic-Acid Guided Cell Editing in Yeast", now U.S. Pat. No. 10,927, 385; which claims priority to U.S. Ser. No. 62/866,041 filed 25 Jun. 2020.

INCORPORATION BY REFERENCE

Submitted with the present application is an electronically filed sequence listing via EFS-Web as an ASCII formatted sequence listing, entitled "INSC041US2 SEQ_LIST", created Dec. 28, 2020, and 10,245 bytes in size. The sequence listing is part of the specification filed Jan. 2, 2021 and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences; hence gene function. The nucleases include nucleic acid-guided nucleases, which enable researchers to generate permanent edits in live cells. Of course, it is desirable to attain the highest editing rates possible in a cell population; however, in many instances the percentage of edited cells resulting from nucleic acid-guided nuclease editing can be in the single digits.

There is thus a need in the art of nucleic acid-guided nuclease editing for improved methods, compositions, modules and instruments for increasing the efficiency of editing. The present disclosure addresses this need.

FIELD OF THE INVENTION

The present disclosure relates to methods and compositions to increase the percentage of edited yeast cells in a cell population using nucleic-acid guided editing, and automated multi-module instruments for performing these methods and using these compositions.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to methods, compositions, modules and automated multi-module cell processing instruments that increase the efficiency nucleic-acid guided editing in a yeast cell population.

Thus, in some embodiments there is provided an editing vector for performing nucleic acid-guided nuclease editing in yeast comprising: a yeast 2-µ backbone, a 2µ origin of replication; a standard constitutive or inducible (e.g., non-minimal or non-core) promoter driving transcription of a gRNA sequence and donor DNA (HA) sequence followed by a terminator element 3' to the gRNA and donor DNA sequences; a standard constitutive (e.g., non-minimal or non-core) promoter driving transcription of a coding sequence for a degron-survival marker fusion gene followed by a terminator element 3' to the degron-survival marker fusion gene; a standard constitutive or inducible (e.g., non-minimal or non-core) promoter driving transcription of a nuclease or nuclease fusion coding sequence with a terminator element 5' to the nuclease coding sequence; and an origin of replication for propagation of the editing vector in bacteria.

In some aspects of this embodiment, the degron is an ubiquitin-dependent degron and the degron is ubiquitin. In some aspects, the survival marker is selected from the group of hygromycin, blasticidin, nourseothricin or kanamycin.

Additionally there is provided in another embodiment an editing vector for performing nucleic acid-guided nuclease editing in yeast comprising: a yeast 2-µ backbone, a 2µ origin of replication; a standard constitutive or inducible (e.g., non-minimal or non-core) promoter driving transcription of a gRNA sequence and donor DNA (HA) sequence with followed by a terminator element 3' to the gRNA and donor DNA sequences; a minimal promoter driving transcription of a coding sequence for a survival marker gene followed by a terminator element 3' to the survival marker gene; a standard constitutive or inducible (e.g., non-minimal or non-core) promoter driving transcription of a nuclease coding sequence with a terminator element 5' to the nuclease or nuclease fusion coding sequence; and an origin of replication for propagation of the editing vector in bacteria.

In some aspects, the minimal promoter is the URA3-d promoter, and in some aspects, the survival marker is selected from the group of hygromycin, blasticidin, nourseothricin or kanamycin. In other aspects, the minimal promoter is the pHIS3 promoter, the pTRP1 promoter, the pLEU2 promoter, the pURA3 promoter, the pTEF1 promoter, or the pHXT7 promoter. In other aspects, the promoter is a weak constitutive promoter such as the pSSA1 promoter, the pPDA1 promoter, the pCYC1 promoter, the pTPS1 promoter, or the pSSB1 promoter.

In yet another embodiment there is provided a method for performing editing in yeast comprising: providing a population of yeast cells; transforming the population of yeast cells with a population of editing vectors, wherein each editing vector comprises: a yeast 2-µ backbone, a 2µ origin of replication; a standard constitutive or inducible (e.g., non-minimal or non-core) promoter driving transcription of a gRNA sequence and donor DNA (HA) sequence with followed by a terminator element 3' to the gRNA and donor DNA sequences; a standard constitutive (e.g., non-minimal or non-core) promoter driving transcription of a coding sequence for a degron-survival marker fusion gene followed by a terminator element 3' to the degron-survival marker fusion gene; a standard constitutive or inducible (e.g., non-minimal or non-core) promoter driving transcription of a nuclease or nuclease fusion coding sequence with a terminator element 5' to the nuclease coding sequence; and an origin of replication for propagation of the editing vector in bacteria; growing the transformed yeast cells in selective medium to select for cells expressing a degron-survival marker fusion protein; providing conditions to allow the transformed yeast cells to edit nucleic acid sequences in the yeast cells; and growing the edited yeast cells.

In some aspects, the degron portion of the degron-survival marker fusion gene is selected from a Ura3-d degon, Ubi-R degron, Ubi-M degron, Ubi-Q degron, Ubi-E degron, ZF1 degron, C-terminal phosphodegron; Ts-degron; lt-degron; auxin inducible degron; DD-degron, LID-degron; PSD degron, B-LID degron, and a TIPI degron.

Also provided is a method for performing editing in yeast comprising: providing a population of yeast cells; transforming the population of yeast cells with a population of editing vectors, wherein each editing vector comprises: a yeast 2-µ backbone, a 2µ origin of replication; a standard constitutive or inducible (e.g., non-minimal or non-core) promoter driving transcription of a gRNA sequence and donor DNA (HA) sequence with followed by a terminator element 3' to the gRNA and donor DNA sequences; a minimal promoter driving transcription of a coding sequence for a survival marker gene followed by a terminator element 3' to the survival marker gene; a standard constitutive or inducible (e.g., non-minimal or non-core) promoter driving transcription of a nuclease or nuclease fusion coding sequence with a terminator element 5' to the nuclease coding sequence; and an origin of replication for propagation of the editing vector in bacteria; growing the transformed yeast cells in selective medium to select for cells expressing a survival marker protein; providing conditions to allow the transformed yeast cells to edit nucleic acid sequences in the yeast cells; and growing the edited yeast cells.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1A is a representation of (i) a standard constitutive promoter driving transcription of an antibiotic resistance gene and (ii) a standard constitutive promoter driving transcription of an antibiotic resistance gene fused at its N-terminus with a ubiquitin peptide. FIG. 1B is a representation of (i) a standard constitutive promoter driving transcription of an antibiotic resistance gene and (ii) a minimal constitutive promoter driving transcription of an antibiotic resistance gene.

It should be understood that the drawings are not necessarily to scale, and that like reference numbers refer to like features.

DETAILED DESCRIPTION

Figure 1C:
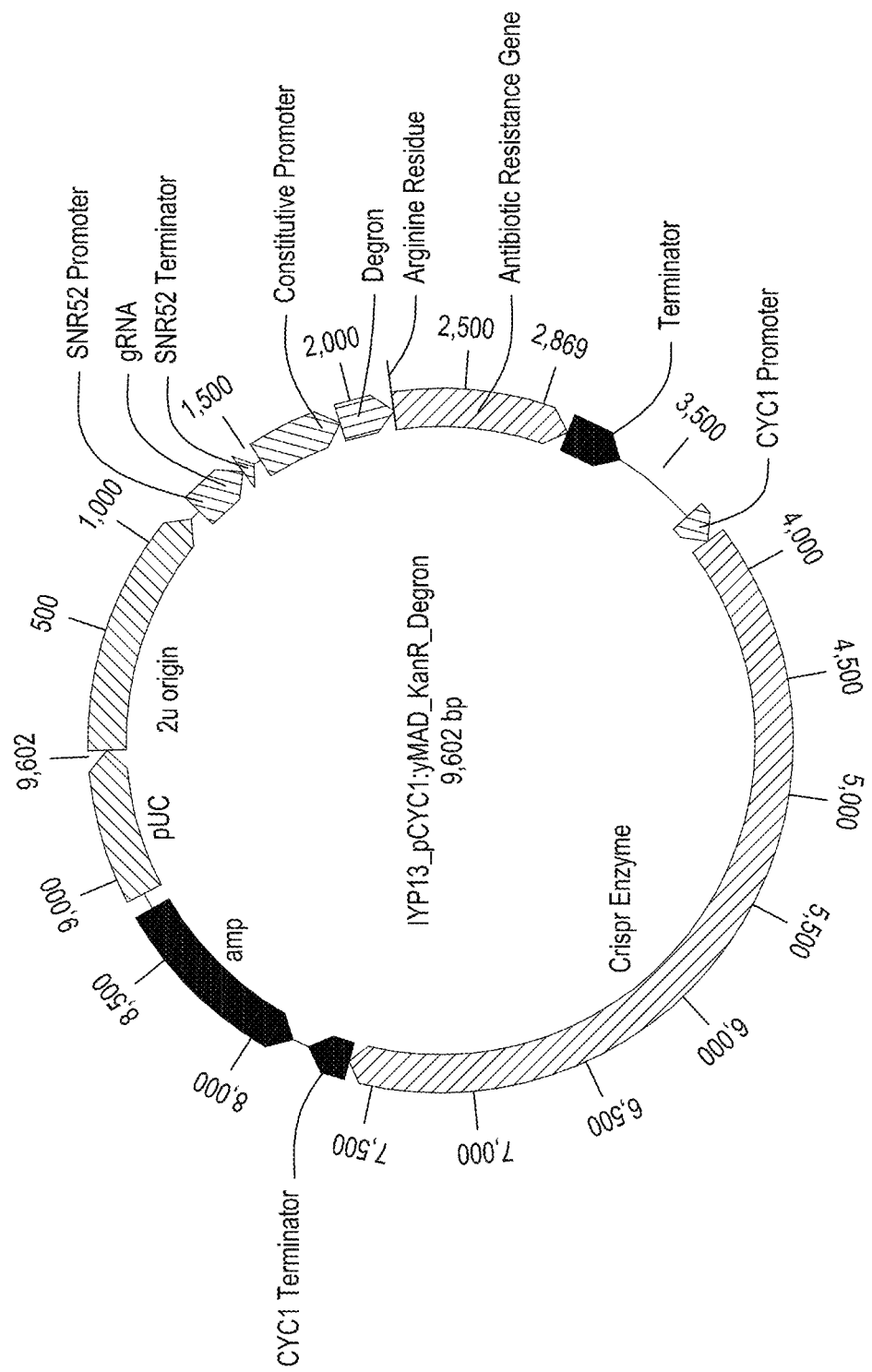
FIG. 1C is an exemplary vector map of a yeast 2-µ plasmid configured for nucleic acid-guided nuclease editing of a yeast genome, where an antibiotic resistance gene is fused at its 5' end to a degron coding sequence.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual*. 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and-for some components-translated in an appropriate host cell.

As used herein the term "donor DNA" or "donor nucleic acid" refers to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region-the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

The terms "editing cassette", "CREATE cassette" or "CREATE editing cassette" refers to a nucleic acid molecule comprising a coding sequence for transcription of a guide nucleic acid or gRNA covalently linked to a coding sequence for transcription of a donor DNA or homology arm.

As used herein, "enrichment" refers to enriching for edited cells by singulation, inducing editing, and growth of singulated cells into terminal-sized colonies (e.g., saturation or normalization of colony growth).

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, nourseothricin N-acetyl transferase, chloramphenicol, erythromycin, tetracycline, gentamicin, bleomycin, streptomycin, rifampicin, puromycin, hygromycin, blasticidin, and G418 may be employed. In other embodiments, selectable markers include, but are not limited to sugars such as rhamnose, human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); herpes simplex virus thymidine kinase (enables negative selection in yeast by 5-Fluoro-2'-deoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers As used herein the term "survival marker" refers to a gene introduced into a cell which confers to that cell the ability to survive growth in a selective medium.

The term "specifically binds" as used herein includes an interaction between two molecules, e.g., an engineered peptide antigen and a binding target, with a binding affinity represented by a dissociation constant of about $10^{-7}$M, about $10^{-8}$M, about $10^{-9}$M, about $10^{-10}$M, about $10^{-11}$M, about $10^{-12}$M, about $10^{-13}$M, about $10^{-14}$M or about $10^{-15}$M.

The terms "target genomic DNA sequence", "cellular target sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. The engine/editing vector for yeast as described herein comprises a coding sequence for a nuclease or nuclease fusion to be used in the nucleic acid-guided nuclease systems; a donor nucleic acid, optionally including an alteration to the cellular target sequence that prevents nuclease binding at a PAM or spacer in the cellular target sequence after editing has taken place; a coding sequence for a gRNA where the gRNA is compatible with the nuclease or nuclease fusion; and a coding sequence for a survival marker gene either fused to a coding sequence for a degron or under transcriptional control of an minimal promoter as described in more detail herein. Further, the engine/editing vector may also and preferably does comprise a barcode. In some embodiments, the engine vector and editing vector may be separate. In this instance, the survival marker fused to a degron or under transcriptional control of a minimal promoter is on the editing vector comprising the gRNA and donor DNA. Further, the engine and editing vectors (whether separate or combined) comprise control sequences operably linked to, e.g., the nuclease coding sequence, recombineering system coding sequences (if present), donor nucleic acid, guide nucleic acid(s), and antibiotic resistance gene(s).

Nuclease-Directed Genome Editing Generally

The automated instruments and methods described herein perform nuclease-directed genome editing, introducing typically tens, to hundreds, to thousands, to tens of thousands of edits to a population of yeast cells. In some embodiments, recursive cell editing is performed where edits are introduced in successive rounds of editing. A nucleic acid-guided nuclease or nuclease fusion complexed with an appropriate synthetic guide nucleic acid in a cell can cut the genome of the cell at a desired location. The guide nucleic acid helps the nucleic acid-guided nuclease or nuclease fusion recognize and cut the DNA at a specific target sequence (either a cellular target sequence or a curing target sequence). By manipulating the nucleotide sequence of the guide nucleic acid, the nucleic acid-guided nuclease or nuclease fusion may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences.

In general, a guide nucleic acid (e.g., gRNA) complexes with a compatible nucleic acid-guided nuclease or nuclease fusion and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette and is optionally under the control of an inducible promoter as described below. For additional information regarding "CREATE" editing cassettes, see U.S. Patent Nos. 9,982,278; 10,266,849; 10,240,167; 10,351,877; 10,364,442; 10,435,715; and 10,465,207 and U.S. Ser. Nos. 16/551,517; 16/773,618; and 16/773,712, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease or nuclease fusion to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acids are provided as a sequence to be expressed from a plasmid or vector and comprises both the guide sequence and the scaffold sequence as a single transcript optionally under the control of an inducible promoter. The guide nucleic acids are engineered to target a desired target sequence (either cellular target sequence or curing target sequence) by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease or nuclease fusion recognizes a protospacer adjacent motif (PAM) sequence adjacent to the target sequence. The target sequence can be any polynucleotide endogenous or exogenous to a yeast cell, or in vitro. For example, the target sequence can be a polynucleotide residing in the nucleus of any eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be and preferably is part of an editing cassette that encodes the donor nucleic acid that targets a cellular target sequence. Alternatively, the guide nucleic acid may not be part of the editing cassette and instead may be encoded on the editing vector backbone. For example, a sequence coding for a guide nucleic acid can be assembled or inserted into a vector backbone first, followed by insertion of the donor nucleic acid in, e.g., an editing cassette. In other cases, the donor nucleic acid in, e.g., an editing cassette can be inserted or assembled into a vector backbone first, followed by insertion of the sequence coding for the guide nucleic acid. Preferably, the sequence encoding the guide nucleic acid and the donor nucleic acid are located together in a rationally-designed editing cassette and are simultaneously inserted or assembled into a vector backbone to create an editing vector. In yet other embodiments, the sequence encoding the guide nucleic acid and the sequence encoding the donor nucleic acid are both included in the editing cassette.

The target sequence is associated with a proto-spacer mutation (PAM), which is a short nucleotide sequence recognized by the gRNA/nuclease complex. The precise preferred PAM sequence and length requirements for different nucleic acid-guided nucleases or nuclease fusions vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease or nuclease fusion may allow for alteration of PAM specificity, improve target site recognition fidelity, decrease target site recognition fidelity, or increase the versatility of a nucleic acid-guided nuclease or nuclease fusion.

In certain embodiments, the genome editing of a cellular target sequence both introduces a desired DNA change to a cellular target sequence, e.g., the genomic DNA of a cell, and removes, mutates, or renders inactive a proto-spacer mutation (PAM) region in the cellular target sequence. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease or nuclease fusion complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

The range of target sequences that nucleic acid-guided nucleases or nuclease fusions can recognize is constrained by the need for a specific PAM to be located near the desired target sequence. As a result, it often can be difficult to target edits with the precision that is necessary for genome editing. It has been found that nucleases and nuclease fusions can recognize some PAMs very well (e.g., canonical PAMs), and other PAMs less well or poorly (e.g., non-canonical PAMs). Because the methods disclosed herein allow for identification of edited cells in a background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease or nuclease fusion component of the nucleic acid-guided nuclease editing system, a polynucleotide sequence encoding the nucleic acid-guided nuclease or nuclease fusion can be codon optimized for expression in particular cell types, such as yeast cells. The choice of nucleic acid-guided nuclease or nuclease fusion to be employed depends on many factors, such as what type of edit is to be made in the target sequence and whether an appropriate PAM is located close to the desired target sequence. Nucleases of use in the methods described herein include but are not limited to Cas 9, Cas 12/Cpf1, MAD2, or MAD7 or other MADzymes. Nuclease fusion enzymes typically comprise a CRISPR nucleic acid-guided nuclease engineered to cut one DNA strand in the target DNA rather than making a double-stranded cut, and the nuclease portion is fused to a reverse transcriptase. For more information on nickases and nuclease fusion editing see U.S. Ser. Nos. 16/740,418; 16/740,420 and 16/740,421, all filed 11 Jan. 2020. As with the guide nucleic acid, the nuclease or nuclease fusion is encoded by a DNA sequence on a vector and may be under the control of an inducible promoter. In some embodiments, the promoter may be separate from but the same as the promoter controlling transcription of the guide nucleic acid; that is, a separate promoter drives the transcription of the nuclease or nuclease fusion and guide nucleic acid sequences but the two promoters may be the same type of promoter. Alternatively, the promoter controlling expression of the nuclease or nuclease fusion may be different from the promoter controlling transcription of the guide nucleic acid; that is, e.g., the nuclease may be under the control of, e.g., the pCYC1 promoter, and the guide nucleic acid may be under the control of the, e.g., SNR52 promoter.

Another component of the nucleic acid-guided nuclease system is the donor nucleic acid comprising homology to the cellular target sequence. The donor nucleic acid is on the same vector and even in the same editing cassette as the guide nucleic acid and preferably is (but not necessarily is) under the control of the same promoter as the editing gRNA (that is, a single promoter driving the transcription of both the editing gRNA and the donor nucleic acid). The donor nucleic acid is designed to serve as a template for homologous recombination with a cellular target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm). When optimally aligned, the donor nucleic acid overlaps with (is complementary to) the cellular target sequence by, e.g., about 20, 25, 30, 35, 40, 50, 60, 70, 80, 90 or more nucleotides. In many embodiments, the donor nucleic acid comprises two homology arms (regions complementary to the cellular target sequence) flanking the mutation or difference between the donor nucleic acid and the cellular target sequence. The donor nucleic acid comprises at least one mutation or alteration compared to the cellular target sequence, such as an insertion, deletion, modification, or any combination thereof compared to the cellular target sequence.

As noted supra, the donor nucleic acid is preferably provided as part of a rationally-designed editing cassette or CREATE cassette, which is inserted into an editing vector backbone where the editing vector backbone may comprise a promoter driving transcription of the editing gRNA and the donor DNA. Moreover, there may be more than one, e.g., two, three, four, or more gRNA/donor nucleic acid pairs inserted into an editing vector (alternatively, a single rationally-designed editing cassette may comprise two to several editing gRNA/donor DNA pairs), where each editing gRNA is under the control of separate different promoters, separate like promoters, or where all gRNAs/donor nucleic acid pairs are under the control of a single promoter. In some embodiments the promoter driving transcription of the editing gRNA and the donor nucleic acid (or driving more than one editing gRNA/donor nucleic acid pair) is optionally an inducible promoter and the promoter driving transcription of the nuclease optionally is an inducible promoter as well. In some embodiments and preferably, the nuclease and editing gRNA/donor DNA are under the control of the same promoter.

Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as possibly a lag in growth for the edited cells that do survive but must repair and recover following editing. However, once the edited cells have a chance to recover, the size of the colonies of the edited cells will eventually catch up to the size of the colonies of unedited cells.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may comprise-in addition to the at least one mutation relative to a cellular target sequence-one or more PAM sequence alterations that mutate, delete or render inactive the PAM site in the cellular target sequence. The PAM sequence alteration in the cellular target sequence renders the PAM site "immune" to the nucleic acid-guided nuclease and protects the cellular target sequence from further editing in subsequent rounds of editing if the same nuclease is used.

In addition, the editing cassette may comprise a barcode. A barcode is a unique DNA sequence that corresponds to the donor DNA sequence such that the barcode can identify the edit made to the corresponding cellular target sequence. The barcode typically comprises four or more nucleotides. In some embodiments, the editing cassettes comprise a collection or library editing gRNAs and of donor nucleic acids representing, e.g., gene-wide or genome-wide libraries of editing gRNAs and donor nucleic acids. The library of editing cassettes is cloned into vector backbones where, e.g., each different donor nucleic acid is associated with a different barcode.

Additionally, in some embodiments, an editing vector or plasmid encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The editing vector comprises (or, if the engine and editing vector are separate, both the engine and editing vectors comprise) control sequences operably linked to the component sequences to be transcribed. As stated above, the promoters driving transcription of one or more components of the nucleic acid-guided nuclease editing system optionally are inducible.

Increasing Efficiency of Editing in Yeast

The present disclosure is drawn to increasing the efficiency of nucleic acid-guided nuclease editing in yeast. It has been found that two different approaches increase editing efficiency in yeast by placing selective pressure on yeast cells to replicate a plasmid or vector comprising the nuclease, guide nucleic acid (gRNA), and donor DNA sequences. The first approach involves transforming yeast cells with an editing plasmid or vector comprising a coding sequence for a nuclease or nuclease fusion enzyme, a coding sequence for a guide RNA (gRNA) compatible with the nuclease or nuclease fusion enzyme, a coding sequence for a donor DNA, an origin of replication, and a coding sequence for a fusion protein comprising a coding sequence for a degron fused 5' to a coding sequence for a survival marker (e.g., an antibiotic resistance gene). This first approach results in destabilizing the survival marker protein leading to a decreased half-life for the survival marker protein. The second approach involves transforming yeast cells with an editing plasmid or vector comprising a coding sequence for a nuclease or nuclease fusion or nuclease fusion enzyme, a coding sequence for a guide RNA (gRNA) compatible with the nuclease enzyme, a coding sequence for a donor DNA, an origin of replication, and a minimal promoter driving transcription of a coding sequence for a survival marker. This second approach decreases the level of transcription of the survival marker gene.

As described above, the term "survival marker" refers to a coding sequence for a gene product that allows a cell expressing the gene product to survive in selective medium. That is, cells expressing the survival marker gene product can grow and proliferate in a selective medium and cells that do not express the survival marker gene product cannot grow and proliferate in the selective medium. Survival markers include the G418 resistance gene (allowing cells expressing this gene to be able to grow in medium containing G418), the blasticidin resistance gene (allowing cells expressing this gene to be able to grow in medium containing blasticidin), the nourseothricin acetyl transferase gene (allowing cells expressing this gene to be able to grow in medium containing nourseothricin) and the hygromycin resistance gene (allowing cells expressing this gene to be able to grow in medium containing hygromycin). The key to both approaches is that the yeast cells transformed with the editing vector express the survival marker protein allowing the yeast cells to grow in selective medium; however, in these yeast cells the survival marker protein is expressed at a low level-due to, in the first instance, a short protein half-life, and due to, in the second instance, a low level of transcription/translation of the survival marker protein-such that selective pressure is placed on these yeast cells to increase replication of the editing plasmid or vector thereby increasing the number of copies of the nuclease, gRNA, and donor DNA present.

In the first approach, graphically depicted in FIG. 1A, a coding sequence for a degron is fused to the 5' terminus of a coding region for a survival marker, in this case an antibiotic resistance gene ("AbxR"). The top-most construct (i) depicts the antibiotic resistance gene (AbxR) under the control of a eukaryotic constitutive promoter. A constitutive promoter driving transcription of AbxR results in high protein expression (high transcription of the antibiotic resistance gene and thus high expression of the antibiotic resistance protein) and the antibiotic resistance protein has a regular half-life. That is, survival marker proteins typically are stable enough to sustain levels of the protein required for normal growth under selective conditions. Below the first construct is a second construct (ii) depicting the antibiotic resistance gene (AbxR) fused at its 5' terminus to a degron ("Ubi"), where the transcription of the degron-AbxR fusion is under the control of a eukaryotic constitutive promoter (e.g., the same eukaryotic constitutive promoter as the first construct (i)). Fusing the survival marker gene (AbxR) to a degron ("Ubi") under constitutive expression results in high protein expression; however, the degron promotes destabilization/degradation of the AbxR protein.

A degron is a portion of a protein that is important in regulation of protein degradation rates. Known degrons include short amino acid sequences, structural motifs, and exposed amino acids located anywhere in the protein. Degrons are present in a variety of organisms, from the N-degrons first characterized in yeast, to the PEST sequence of mouse ornithine decarboxylase. Although there are many types of different degrons- and a high degree of variability amongst them-degrons are all similar for their involvement in regulating the rate of protein degradation. Mechanisms of degradation are often deemed "ubiquitin dependent" or "ubiquitin independent." Ubiquitin-dependent degrons are so named because they are implicated in the polyubiquitination process for targeting a protein to the proteasome. In contrast, ubiquitin independent degrons are not necessary for polyubiquitination. Ubiquitin is a small regulator protein consisting of 76 amino acids and is found ubiquitously (hence the name) in most tissues of eukaryotic organisms.

The addition of ubiquitin to a substrate protein (in this case, a survival marker protein/antibiotic resistance protein) is called ubiquitination and thereby marks the substrate protein for degradation. Ubiquitin degron tags of use in the present methods and compositions include Ubi-R, a 228 ubiquitin sequence with an Arginine (R) appended on the 3' end; Ubi-M, a 228 bp ubiquitin sequence with a Methionine (M) appended on the 3' end; Ubi-Q, a 228 bp ubiquitin sequence with a Glutamine (Q) appended on the 3' end; and Ubi-E, a 228 bp ubiquitin sequence with a Methionine (M) appended on the 3' end. In addition to the ubiquitin tags, are ubiquitin independent degrons such as the ZF1 degron, a 36 amino acid motif recognized by the SOCS-box protein ZIF-1, which binds to the elongin C subunit of an ECS ubiquitin ligase complex; the C-terminal phosphodegrons (CTPD) from the C. elegans OMA-1 protein; and conditional degrons (e.g., inducible degrons) such as the Ts-degron and lt-degrons, which are induced by temperature shift and function when added to the N terminus of a coding protein; the auxin inducible degron (AID), which is a small protein tag that interacts with an F-Box ubiquitin ligase complex in the presence of a small molecule called auxin; DD-based degrons, which are induced by Shield-1 ligand binding; LID, which is induced by Shield-1 ligand binding and functions only when fused to the C-terminus of a protein; the PSD and B-LID degrons, which are blue light inducible degrons; and TIPI, which is a TEV protease expression induced degron. (See, e.g., Chen, et al., Yeast Research, 12(5):598-607 (2012).)

In the present degron construct (ii) of FIG. 1A, a coding sequence for a ubiquitin/N-degron tag ("Ubi") is fused to the N-terminus of the coding sequence for the survival marker protein (e.g., the antibiotic resistance gene "AbxR") resulting in a Ubi-AbxR fusion protein. The ubiquitin/N-degron tag is cleaved off the fusion protein in vivo (depicted by the "Pac Man"-like element), generating a protein with an N-terminal amino acid other than methionine. Certain destabilizing N-terminal amino acid residues (primarily arginine) decrease the half-life of the protein carrying the N-degron tag. Here, the ubiquitin tag is cleaved off, exposing an arginine residue ("R") at the 5' terminus of the survival marker/antibiotic resistance protein. When arginine ("R") is exposed at the N-terminus of the survival marker protein, the survival marker protein is degraded. Degradation of the survival marker protein places selective pressure on the yeast cell in selective medium; thus, the yeast cell must replicate the editing plasmid or vector-that is, increase the plasmid copy number-in order to survive. The increase in plasmid copy number leads to a concurrent increase in the copy numbers of the expressed nuclease, the transcribed gRNA, and the donor DNA.

FIG. 1B is a representation of (i) a standard constitutive promoter driving an antibiotic resistance gene and (ii) a minimal constitutive promoter driving an antibiotic resistance gene. As an alternative to the approach of destabilizing the survival marker protein to influence plasmid copy number shown in FIG. 1A, the approach depicted in FIG. 1B influences plasmid copy number via the expression level of the survival marker gene. It has been found that expression levels of a protein can be down-regulated by using inducible promoters and truncated or minimal (also termed "core") promoters. Minimal or core promoters typically comprise the minimal portion of a promoter required to properly initiate transcription, including one or more of a transcription start site, a binding site for RNA polymerase, a general transcription factor binding site such as a TATA box or B recognition element, and a downstream core promoter element (DPE). Often, the minimal promoter is located between −35 to +35 of the transcription start site. Use of a minimal promoter typically guarantees that there is always at least a low amount of transcription of the target gene (in this case the survival marker gene). Table 1 lists a number of exemplary minimal constitutive promoters and Table 2 lists weak constitutive promoters. (See, e.g., Natsuma and Kanemaki, Ann. Rev. Genetics, 51:83-102 (2017).)

TABLE 1

Minimal Promoters

| Promoter Name | Sequence | SEQ ID No. |
|---|---|---|
| Ura3-d | TAACCCAACTGCACAGAACAAAAACCTGCAGGAAACGAAGATAAATC | 1 |
| pHIS3 (100 bp) | ATTGGCATTATCACATAATGAATTATACATTATATAAAGTAATGTGATTT CTTCGAAGAATATACTAAAAAATGAGCAGGCAAGATAAACGAAGGCAAAG | 2 |
| pHIS3 (50 bp) | CTTCGAAGAATATACTAAAAAATGAGCAGGCAAGATAAACGAAGGCAAAG | 3 |
| pHIS3 (30 bp) | AATGAGCAGGCAAGATAAACGAAGGCAAAG | 4 |
| pHIS3 (20 bp) | CAAGATAAACGAAGGCAAAG | 5 |
| pTRP1 (100 bp) | TTCGGTCGAAAAAAGAAAAGGAGAGGGCCAAGAGGGAGGGCATTGGTGAC TATTGAGCACGTGAGTATACGTGATTAAGCACACAAAGGCAGCTTGGAGT | 6 |
| pTRP1 (50 bp) | TATTGAGCACGTGAGTATACGTGATTAAGCACACAAAGGCAGCTTGGAGT | 7 |
| pTRP1 (30 bp) | GTGATTAAGCACACAAAGGCAGCTTGGAGT | 8 |

TABLE 1-continued

Minimal Promoters

| Promoter Name | Sequence | SEQ ID No. |
|---|---|---|
| pTRP1 (20 bp) | ACACAAAGGCAGCTTGGAGT | 9 |
| pLEU2 (100 bp) | TTTTCCAATAGGTGGTTAGCAATCGTCTTACTTTCTAACTTTTCTTACCT TTTACATTTCAGCAATATATATATATATATTTCAAGGATATACCATTCTA | 10 |
| pLEU2 (50 bp) | TTTACATTTCAGCAATATATATATATATATTTCAAGGATATACCATTCTA | 11 |
| pLEU2 (30 bp) | ATATATATATTTCAAGGATATACCATTCTA | 12 |
| pLEU2 (20 bp) | TTCAAGGATATACCATTCTA | 13 |
| pURA3 (100 bp) | GGTATATATACGCATATGTGGTGTTGAAGAAACATGAAATTGCCCAGTAT TCTTAACCCAACTGCACAGAACAAAAACCTGCAGGAAACGAAGATAAATC | 14 |
| pURA3 (50 bp) | TCTTAACCCAACTGCACAGAACAAAAACCTGCAGGAAACGAAGATAAATC | 15 |
| pURA3 (30 bp) | ACAAAAACCTGCAGGAAACGAAGATAAATC | 16 |
| pURA3 (20 bp) | GCAGGAAACGAAGATAAATC | 17 |
| pTEF1 (100 bp) | TCAAGTTTCAGTTTCATTTTTCTTGTTCTATTACAACTTTTTTTACTTCT TGCTCATTAGAAAGAAAGCATAGCAATCTAATCTAAGTTTTAATTACAAA | 18 |
| pTEF1 (50 bp) | TGCTCATTAGAAAGAAAGCATAGCAATCTAATCTAAGTTTTAATTACAAA | 19 |
| pTEF1 (30 bp) | TAGCAATCTAATCTAAGTTTTAATTACAAA | 20 |
| pTEF1 (20 bp) | ATCTAAGTTTTAATTACAAA | 21 |
| pHXT7 (100 bp) | TAAAATAATAAAACATCAAGAACAAACAAGCTCAACTTGTCTTTTCTAAG AACAAAGAATAAACACAAAAACAAAAGTTTTTTTAATTTTAATCAAAAA | 22 |
| pHXT7 (50 bp) | AACAAAGAATAAACACAAAAACAAAAGTTTTTTTAATTTTAATCAAAAA | 23 |
| pHXT7 (30 bp) | ACAAAAGTTTTTTTAATTTTAATCAAAAA | 24 |
| pHXT7 (20 bp) | TTTTTAATTTTAATCAAAAA | 25 |

TABLE 2

Weak Constitutive Promoters

| Promoter Name | Sequence | SEQ ID No. |
|---|---|---|
| pSSA1 | TCGACAAATTGTTACGTTGTGCTTTGATTTCTAAAGCGCTTCTTCACCTGCAG GTTCTGAGCCCTAAGAAAAAAATTTCCTTGGTTGAAAATGGCGGAAAAAAA AATTCAGAAAAAGAAATAAAGCACGTGTGCGCGGTGTGTGGATGATGGTTTCA TCATTGTCAACGGCATTTTCGTTCTTGTGGATTGTTGTAAACTTTCCAGAACA TTCTAGAAAGAAAGCACACGGAACGTTTAGAAGCTGTCATTTGCGTTTTTTCT CCAGATTTTAGTTGAGAAAGTAATTAAATTATTCTTCTTTTTCCAGAACGTTC CATCGGCGGCAAAAGGGAGAGAAAGAACCCAAAAAGAAGGGGGGCCATTTAGA TTAGCTGATCGTTTCGAGGACTTCAAGGTTATATAAGGGGTGGATTGATGTAT CTTCGAGAAGGGATTGAGTTGTAGTTTCGTTTCCCAATTCTTACTTAAGTTGT TTTATTTTCTCTATTTGTAAGATAAGCACATCAAAGAAAAGTAATCAAGTAT TACAAGAAACAAAAATTCAAGTAAATAACAGATAAT | 26 |

TABLE 2-continued

Weak Constitutive Promoters

| Promoter Name | Sequence | SEQ ID No. |
|---|---|---|
| pPDA1 | GAAATTCAAAACTCTCCAGACAAAGCCTGCCATTTGGCCAAGCAAGCTTTTGA CGACGCTATTGCTGAGTTGGACACTCTGTCTGAAGAATCATACAAAGATAGCA CACTTATCATGCAACTGCTAAGGGACAATTTAACCTTATGGACTTCAGACATG TCCGAGTCCGGTCAAGCTGAAGACCAACAACAACAACAACAACATCAGCAACA GCAGCCACCTGCTGCCGCCGAAGGTGAAGCACCAAAGTAAGTATTCTGATAAA TCTAAAGAGAAATTACTAAAAAAAAGAAAAAAAAAAGAACGGGGGTGTAATAA TTTGTAGTTCATTATTGCAATTATATATCTATATCTATATATGTATATAACAT TAACATGTGCATGTACACACGTAATCGCGCGTGTACATGTCTATATGTGTTAC TTGAACTATACTGTTTTGACGTGTATGTTTATTTATCTCTCTTCTGATTCCTC CACCCCTTCCTTACTCAACCGGGTAAATGTCGCATCATGACTCCCGACAATAA TCCCCTCTGGTATAGCGAGAAGCAACTTTAGCTTCTTAACGGCAAGAACTTTT TTATGTTTGTCGCACCTGTATCTTCACAAAAGTTGGATACAGCAATAAGAAAG GAAACCACATTTGTGCCA | 27 |
| pCYC1 | AGAAAGATGTCAACTGAAAAAAAAAAAGGTGAACACAGGAAAAAAAATAAAAA AAAAAAAAAAAAAAGGAGGACGAAACAAAAAAGTGAAAAAAAATGAAAATTTT TTTGGAAAACCAAGAAATGAATTATATTTCCGTGTGAGACGACATCGTCGAAT ATGATTCAGGGTAACAGTATTGATGTAATCAATTTCCTACCTGAATCTAAAA TTCCCGGGAGCAAGATCAAGATGTTTTCACCGATCTTTCCGGTCTCTTTGGCC GGGGTTTACGGACGATGGCAGAAGACCAAAGCGCCAGTTCATTTGGCGAGCGT TGGTTGGTGGATCAAGCCCACGCGTAGGCAATCCTCGAGCAGATCCGCCAGGC GTGTATATATAGCGTGGATGGCCAGGCAACTTTAGTGCTGACACATACAGGCA TATATATATGTGTGCGACGACACATGATCATATGGCATGCATGTGCTCTGTAT GTATATAAAACTCTTGTTTTCTTCTTTTCTCTAAATATTCTTTCCTTATACAT TAGGACCTTTGCAGCATAAATTACTATACTTCTATAGACACACAAACACAAAT ACACACACTAAATTAATA | 28 |
| pTPS1 | AACCCGGTCTCGAAGAACATCAGCACCACGCCCGCAACGACAAAGAACATTGC AATACACTTGCATATGTGAGCATAGTCGAGCGGTCCGTTCTGTGGTTGATGCT GTTGTTCTTTCTTCTGTTTGTCAGGGGTGATAGCCATATCTTCGTGCTCTTGT TGCGATTGTTCTGTTCCATCTGCACCAGAACAAAGAACAAAAGAACAAGGAAC AAAGTCCAAGCACGTCAGCGCTGTTTATAAGGGGATTGACGAGGGATCGGGCC TAGAGTGCCAGCGCGCCAGGGAGAGGGAGCCCCCTGGGCCCTCATCCGCAGGC TGATAGGGGTCACCCCGCTGGGCAGGTCAGGGCAGGGGCTCTCAGGGGGCGC CATGGACAAACTGCACTGAGGTTCTAAGACACATGTATTATTGTGAGTATGTA TATATAGAGAGAGATTAAGGCGTACAGCCGGGTGGTAGAGATTGATTAACTTG GTAGTCTTATCTTGTCAATTGAGTTTCTGTCAGTTTCTTCTTGAACAAGCACG CAGCTAAGTAAGCAACAAAGCAGGCTAACAAACTAGGTACTCACATACAGACT TATTAAGACATAGAACT | 29 |
| pSSB1 | CAGAGGAGTACACACGGGACTTGATCGAACAGATCGTGTTACAGTTGCGCTCG CAAAGAATGAAAATGGTTCAGACAAAGGATCAGTTCCTATTTATCTACCATGC TGCCAAGTATCTTAACAGTCTTTCCGTGAACCAATAGACAGCTATATAAAAGT TCCTAATTGTGCATTTTTTCAATAACAATACTTATTCATCCTTATAATTATAT TCTAGCTTCGTTGTCATGGGAACATAGCCCATACACCGCAGTTATTTATGATC ATTTCGAACGGGAAGTATGGATGAATCTTTTTTTTTTTTTTTTATAGCACGC AACTGAAAAAAAAAAAAGAAAAATTTTTCATCTTCGCTCGACGTTTCTTTTG TAGTACTCATCTCTTTTTATATAAAGATTAATTAGTTATTGTCGCTTTGCTTT TCCTTCTTTAAAAAATGTTTCTTGCTTTTGGATTTTCAGATGTCCCAAGATCA TTACAGTATTTTAATTGAACAAA | 30 |

As noted in FIG. 1B at (i), the survival marker/antibiotic resistance gene ("AbxR") under the control of a standard constitutive promoter results in high protein expression, normal protein half-life, and a low plasmid copy number. Again, because the survival marker/antibiotic resistance gene is transcribed at a high rate and thus the survival marker/antibiotic resistance protein is expressed at a high rate, there is little to no selective pressure on the yeast cell harboring the editing vector or plasmid to increase replication of the editing vector or plasmid, and thus there is no attendant increase in the expression of the nuclease, transcription of the gRNA, or transcription of the donor DNA.

However, in FIG. 1B at (ii), instead of a standard constitutive promoter, a minimal promoter is used resulting in reduced transcription of the survival marker/antibiotic resistance gene ("AbxR"), and thus reduced expression of the survival marker/antibiotic resistance protein. Here, because the survival marker/antibiotic resistance gene is transcribed at a low rate and thus the survival marker/antibiotic resistance protein is expressed at a low rate, there is increased selective pressure on the yeast cell harboring the editing vector or plasmid to increase replication of the editing vector or plasmid. Increasing replication of the plasmid not only allows the yeast cell to survive, but additionally increases the expression of the nuclease, transcription of the gRNA, and copies of the donor DNA.

FIG. 1C is an exemplary vector map of a yeast 2-μ plasmid configured for nucleic acid-guided nuclease editing of a yeast genome, where an antibiotic resistance gene is fused at its 5' end to a degron. As described in relation to FIG. 1A, such an editing plasmid or vector results in an increase in plasmid copy number in the host yeast cell. Beginning at 12 o'clock, there is a 2μ origin of replication; an SNR52 promoter driving transcription of a gRNA and donor DNA (HA) with SNR52 terminator element; a standard constitutive promoter driving transcription of a coding sequence for a degron-antibiotic resistance fusion gene with a terminator; a CYC1 promoter driving transcription of a CRISPR enzyme or nuclease fusion coding sequence with a CYC1 terminator; an ampicillin resistance gene to allow for selection in bacteria; and a pUC origin of replication for propagation of the editing vector in bacteria. As described above in relation to FIG. 1A, the fusion of the degron to the survival maker protein results in degradation of the survival marker protein, which in turn places selective pressure on the yeast cell in selective medium; thus, the yeast cell must replicate the editing plasmid or vector-that is, increase the plasmid copy number-in order to survive. The increased plasmid copy number leads to an increase in the copy numbers of the expressed nuclease, the transcribed gRNA, and the donor DNA.

Figure 1D:
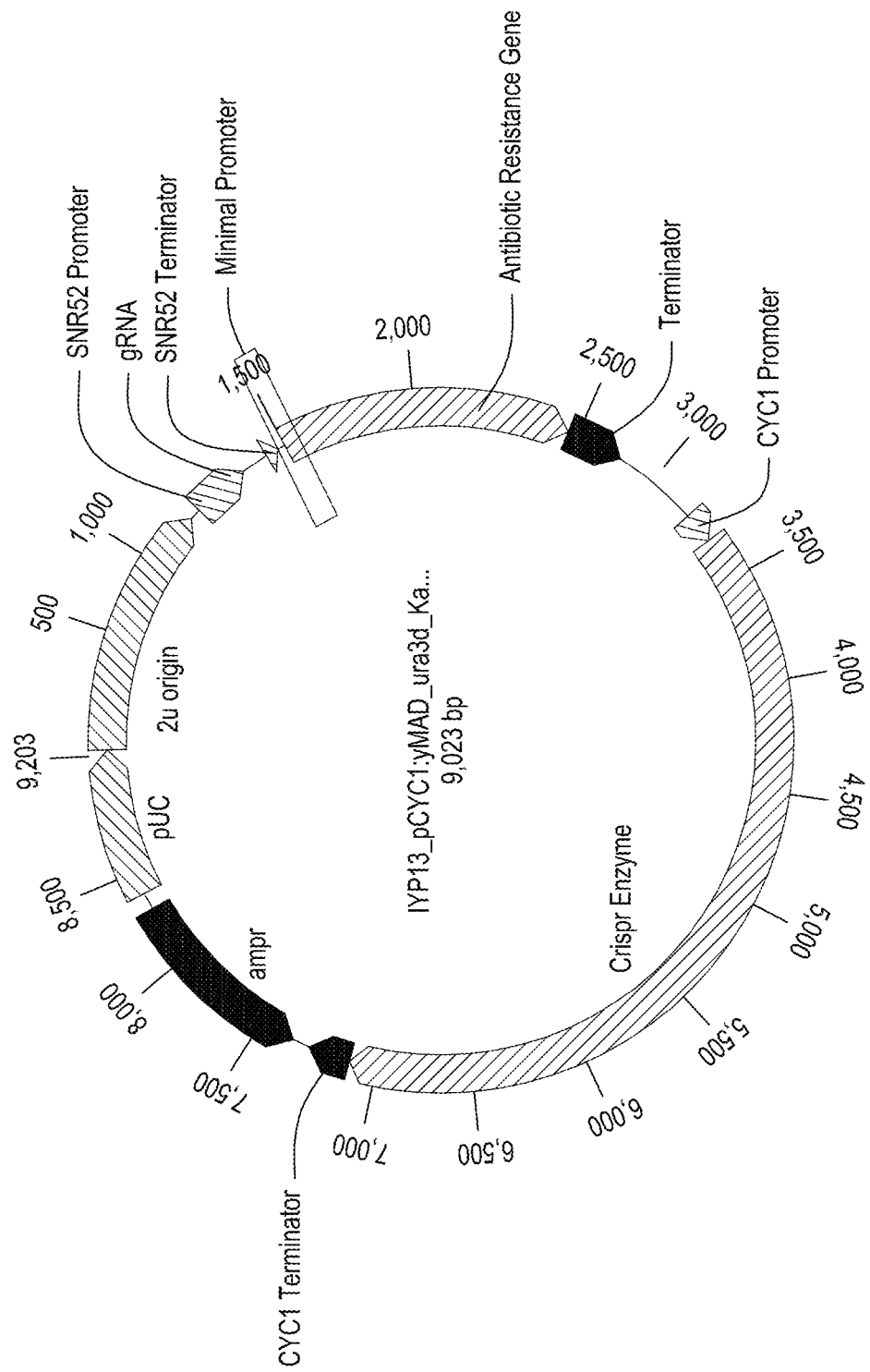
FIG. 1D is an exemplary vector map of a yeast 2-µ plasmid configured for nucleic acid-guided nuclease editing of a yeast genome, where the transcription of an antibiotic resistance gene is driven by a minimal constitutive promoter.

FIG. 1D is an exemplary vector map of a yeast 2-μ plasmid configured for nucleic acid-guided nuclease editing of a yeast genome, where the expression of an antibiotic resistance gene is driven by a minimal constitutive promoter. As described in relation to FIG. 1B and like the vector depicted in FIG. 1C, this editing plasmid or vector results in an increase in plasmid copy number in the host yeast cell. Beginning at 12o'clock, there is a 2μ origin of replication; an SNR52 promoter driving transcription of a gRNA and donor DNA (HA) with SNR52 terminator element; a minimal promoter driving transcription of a coding sequence for an antibiotic resistance gene with a terminator; a CYC1 promoter driving transcription of a CRISPR enzyme or nuclease fusion coding sequence with a CYC1 terminator; an ampicillin resistance gene to allow for selection in bacteria; and a pUC origin of replication for propagation of the editing vector in bacteria. Again, because the survival marker/antibiotic resistance gene is transcribed at a low rate and thus the survival marker/antibiotic resistance protein is expressed at a low rate, there is increased selective pressure on the yeast cell harboring the editing vector or plasmid to increase replication of the vector or plasmid. Increasing replication of the plasmid not only allows the yeast cell to survive, but increases the expression of the nuclease, transcription of the gRNA, and copies of the donor DNA.

Figure 2A:
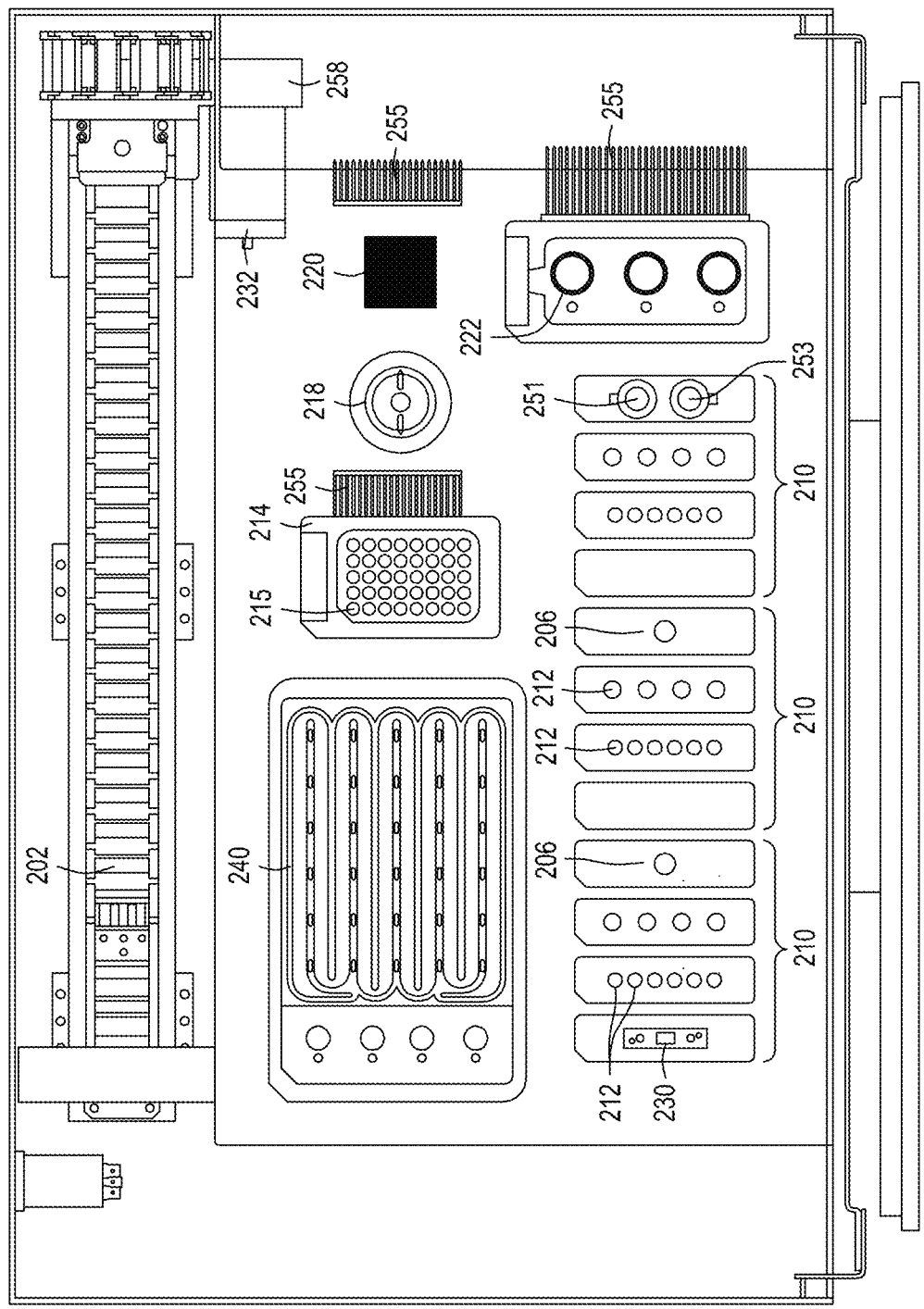
FIGS. 2A-2C depict three different views of an exemplary automated multi-module cell processing instrument for performing nucleic acid-guided nuclease editing.

Automated Cell Editing Instruments and Modules to Perform Nucleic Acid-Guided Nuclease Editing in Yeast Cells
Automated Cell Editing Instruments FIG. 2A depicts an exemplary automated multi-module cell processing instrument 200 to, e.g., perform one of the exemplary workflows for targeted gene editing of live yeast cells. The instrument 200, for example, may be and preferably is designed as a stand-alone desktop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 comprising reservoirs 212 and transformation module 230 (e.g., a flow-through electroporation device as described in detail in relation to FIGS. 5B-5F), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge 210 and wash cartridge 204 may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips 215 may be provided in a pipette transfer tip supply 214 for use with the air displacement pipettor 232.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (described in greater detail below in relation to FIGS. 3A-3D). Additionally seen is the TFF module 222 (described above in detail in relation to FIGS. 4A-4E). Also illustrated as part of the automated multi-module cell processing instrument 200 of FIG. 2A is a singulation module 240 (e.g., a solid wall isolation, incubation and normalization device (SWIIN device) is shown here) described herein in relation to FIGS. 6D-6G, served by, e.g., robotic liquid handling system 258 and air displacement pipettor 232. Additionally seen is a selection module 220. Also note the placement of three heatsinks 255.

Figure 2B:
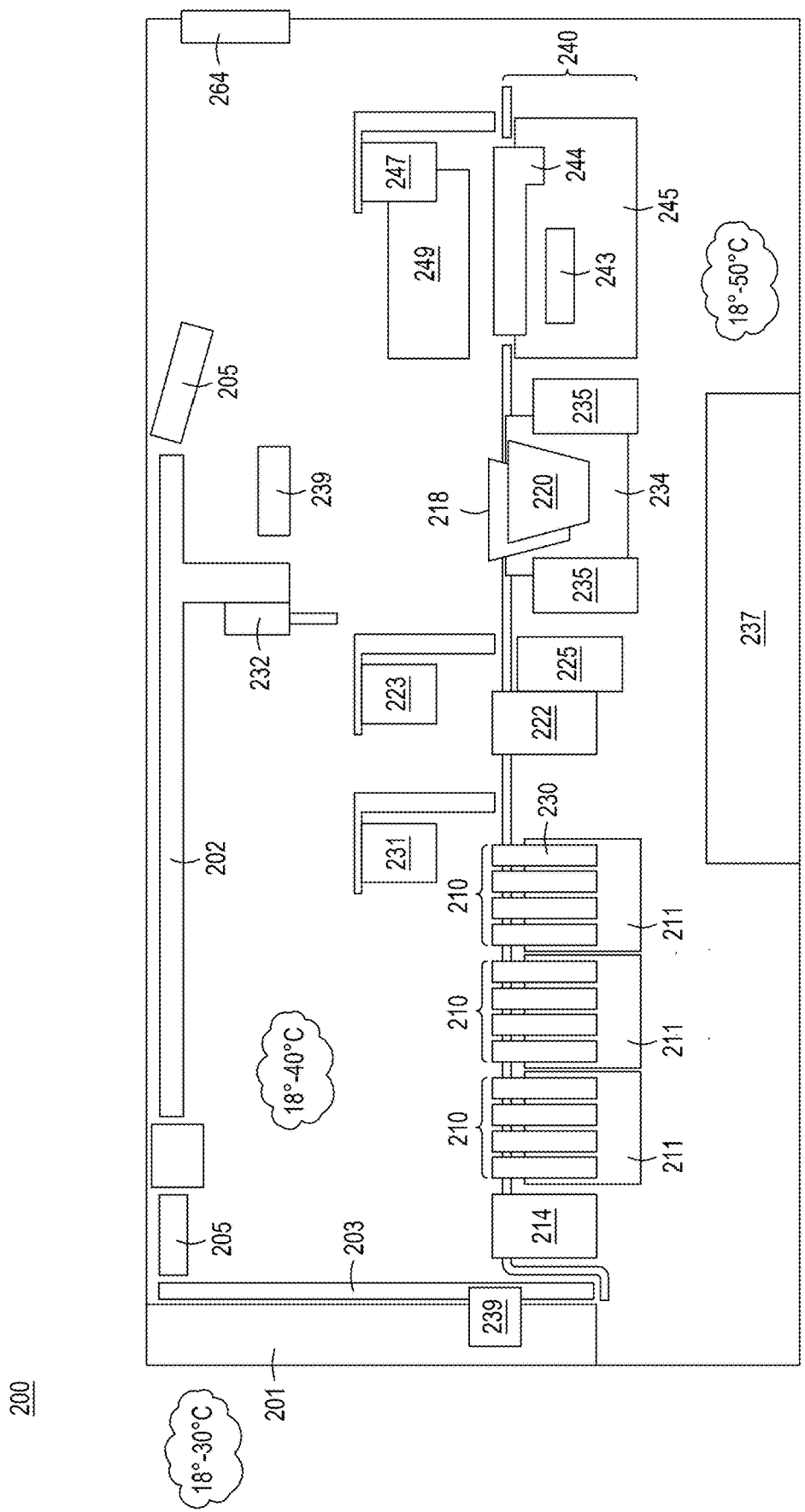

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232. The deck of the multi-module cell processing instrument 200 may include a protection sink such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 233. Thermal assemblies 225, 235, and 245 encompass thermal electric devices such as Peltier devices, as well as heatsinks, fans and coolers. The rotating growth vial 218 is within a growth module 234, where the growth module is served by two thermal assemblies 235. Selection module is seen at 220. Also seen is the SWIIN module 240, comprising a SWIIN cartridge 241, where the SWIIN module also comprises a thermal assembly 245, illumination 243 (in this embodiment, backlighting), SWIIN cover 244, evaporation and condensation control 249, and where the SWIIN module is served by SWIIN interface (e.g., manifold arm) and actuator 247. Also seen in this view is touch screen display 201, display actuator 203, illumination 205 (one on either side of multi-module cell processing instrument 200), and cameras 239 (one illumination device on either side of multi-module cell processing instrument 200). Finally, element 237 comprises electronics, such as circuit control boards, high-voltage amplifiers, power supplies, and power entry; as well as pneumatics, such as pumps, valves and sensors.

Figure 2C:
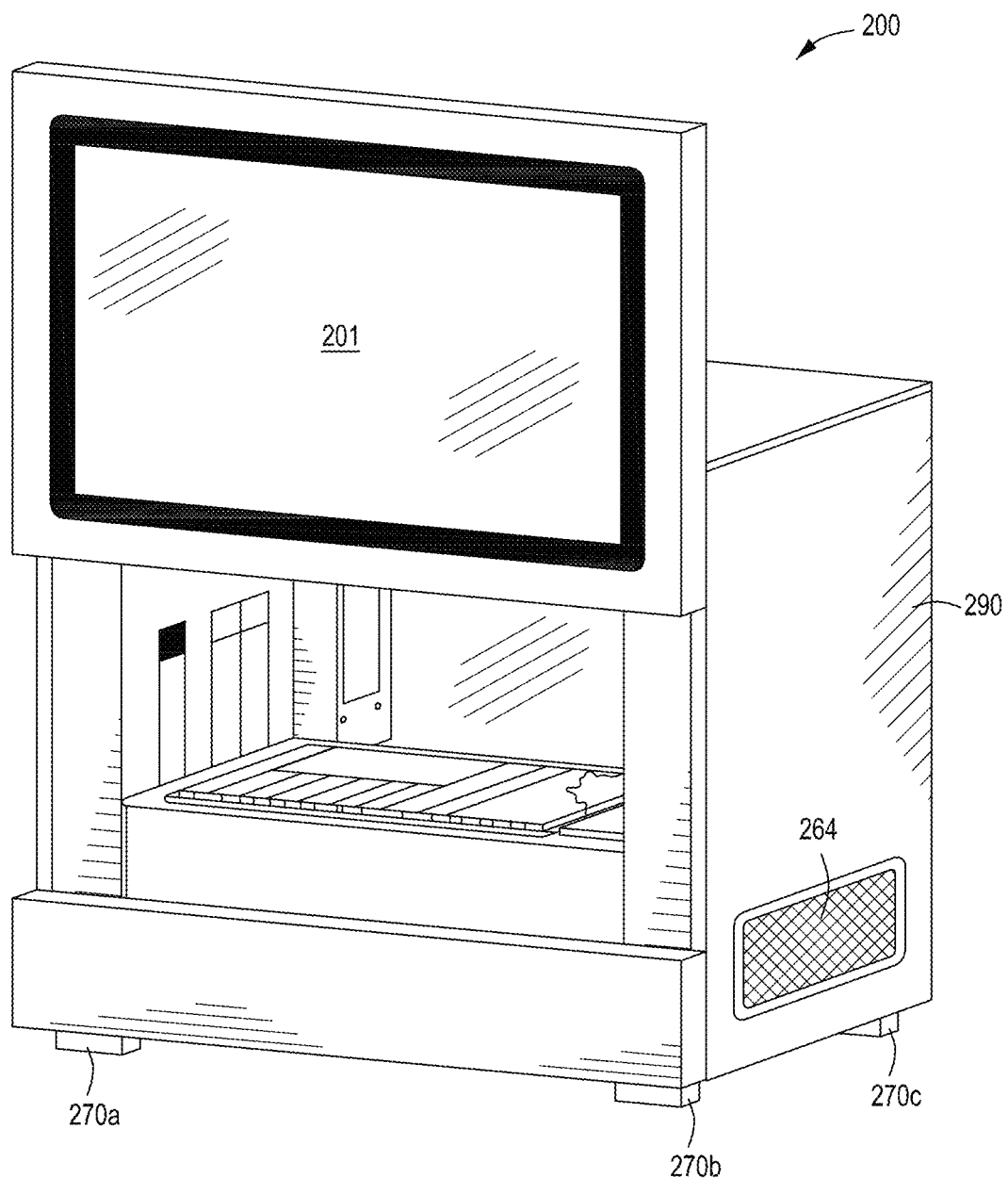

FIG. 2C illustrates a front perspective view of multi-module cell processing instrument 200 for use in as a desktop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device, a rotating growth vial 218 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. Nos. 10,253,316; 10,329,559; 10,323,242; 10,421,959; 10,465,185; 10,519,437; 10,584,333; and 10,584,334 and U.S. Ser. No. 16/750,369, filed 23 Jan. 2020; Ser. No. 16/822,249, filed 18 Mar. 2020; and Ser. No. 16/837,985, filed 1 Apr. 2020, all of which are herein incorporated by reference in their entirety.

The Rotating Cell Growth Module

Figure 3A:
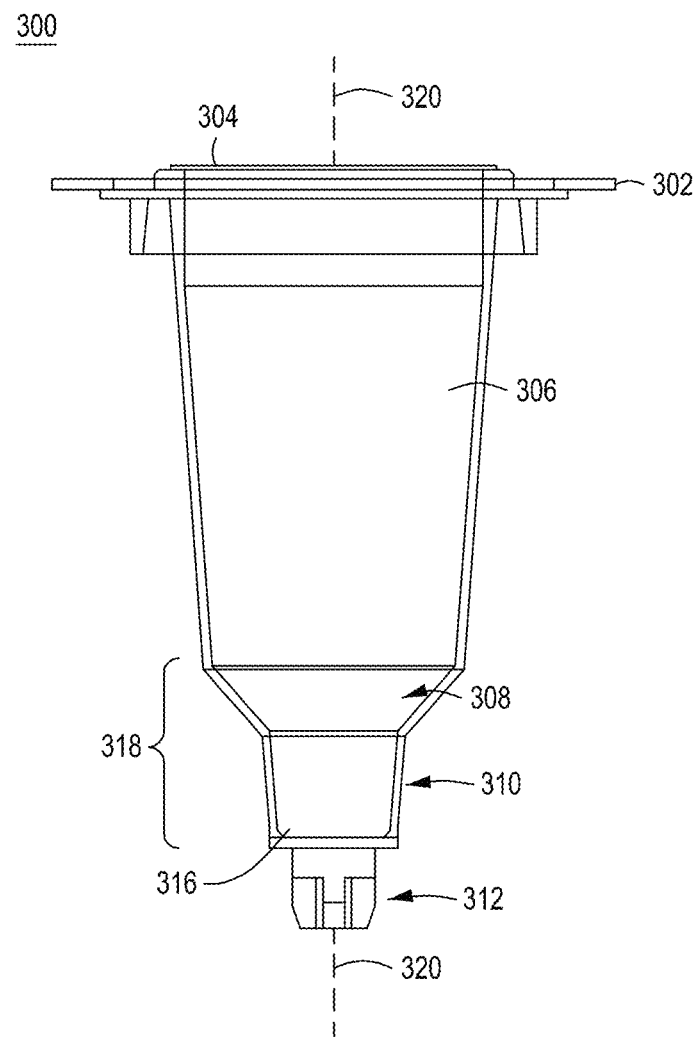
FIG. 3A depicts one embodiment of a rotating growth vial for use with the cell growth module described herein and in relation to FIGS. 3B-3D.

FIG. 3A shows one embodiment of a rotating growth vial 300 for use with the cell growth device and in the automated multi-module cell processing instruments described herein. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for sensitive measurement of OD values when the OD values of the cell culture in the vial are at a high level (e.g., later in the cell growth process), whereas the second light path 308 allows for sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 400 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 302 to overlap and engage with the cell growth device. In automated systems, the rotating growth vial 300 may be tagged with a barcode or other identifying means that can be read by a scanner or camera (not shown) that is part of the automated system.

The volume of the rotating growth vial 300 and the volume of the cell culture (including growth medium) may vary greatly, but the volume of the rotating growth vial 300 must be large enough to generate a specified total number of cells. In practice, the volume of the rotating growth vial 300 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 300. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 300 preferably is fabricated from a bio-compatible optically transparent material-or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
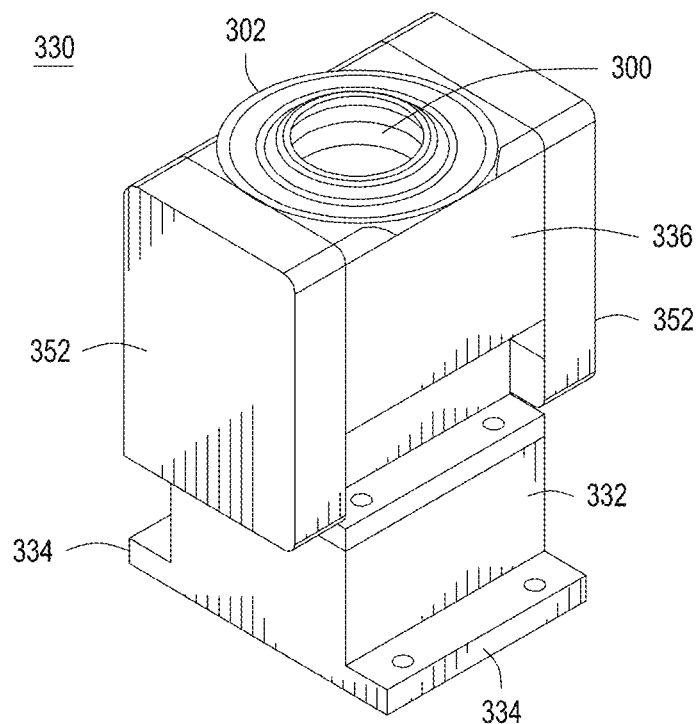
FIG. 3B illustrates a perspective view of one embodiment of a rotating growth vial in a cell growth module housing.
Figure 3C:
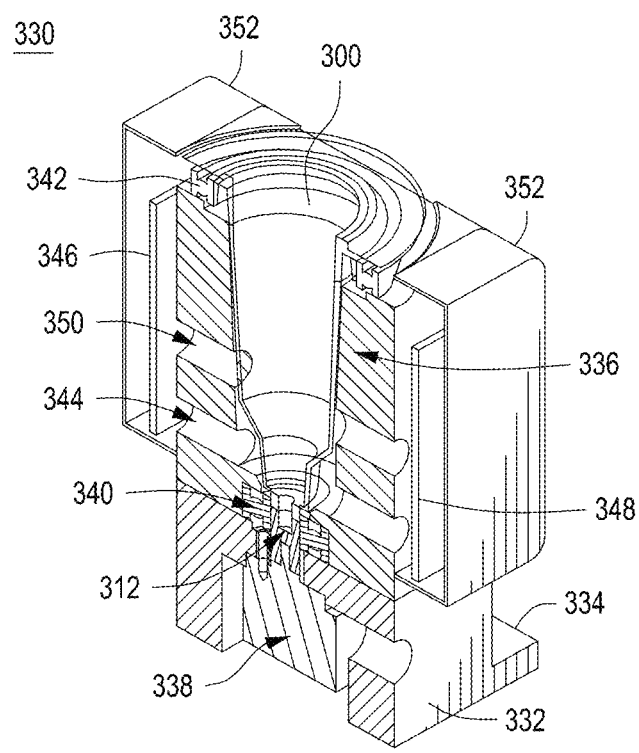
FIG. 3C depicts a cut-away view of the cell growth module from FIG. 3B.

FIG. 3B is a perspective view of one embodiment of a cell growth device 330. FIG. 3C depicts a cut-away view of the cell growth device 330 from FIG. 3B. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3C depicts additional detail. In FIG. 3C, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C comprises two light paths: a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3C but may be seen in FIG. 3A. In addition to light paths 344 and 340, there is an emission board 348 to illuminate the light path(s), and detector board 346 to detect the light after the light travels through the cell culture liquid in the rotating growth vial 300.

The motor 338 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

The processor (not shown) of the cell growth device 330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 330-may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 330, where the second spectrophotometer is used to read a blank at designated intervals.

Figure 3D:
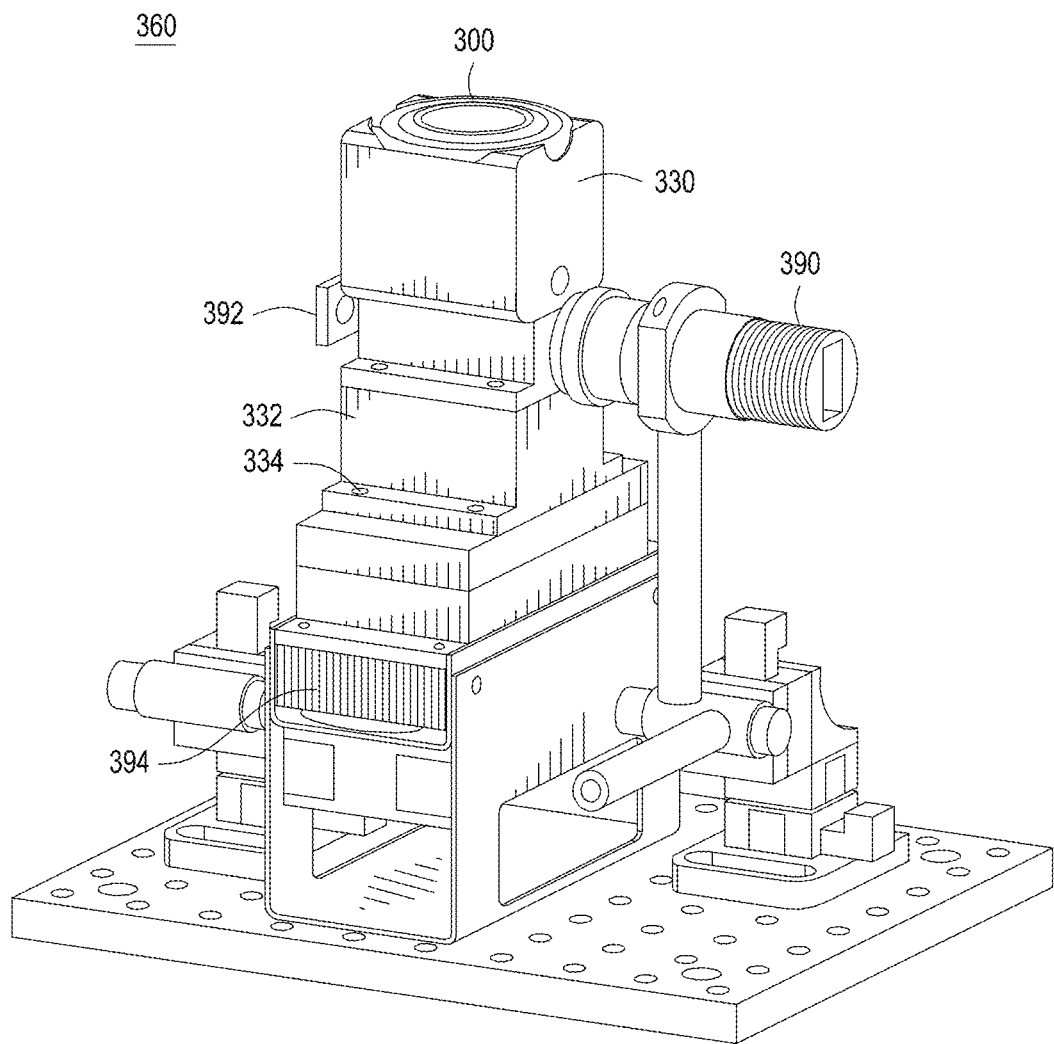
FIG. 3D illustrates the cell growth module of FIG. 3B coupled to LED, detector, and temperature regulating components.

FIG. 3D illustrates a cell growth device 330 as part of an assembly 360 comprising the cell growth device 330 of FIG. 3B coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 330 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 330 may include additional sensors for measuring, e.g., dissolved oxygen, carbon dioxide, pH, conductivity, and the like. For additional details regarding rotating growth vials and cell growth devices see U.S. Ser. Nos. 10,435,662; 10,443,031; 10,590,375 and U.S. Ser. No. 16/552,981, filed 7 Aug. 2019; Ser. No. 16/780,640, filed 3 Feb. 2020.

The Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one subcomponent or module that is desired in cell processing systems for the processes listed above is a module or component that can grow, perform buffer exchange, and/or concentrate cells and render them competent so that they may be transformed or transfected with the nucleic acids needed for engineering or editing the cell's genome.

Figure 4A:
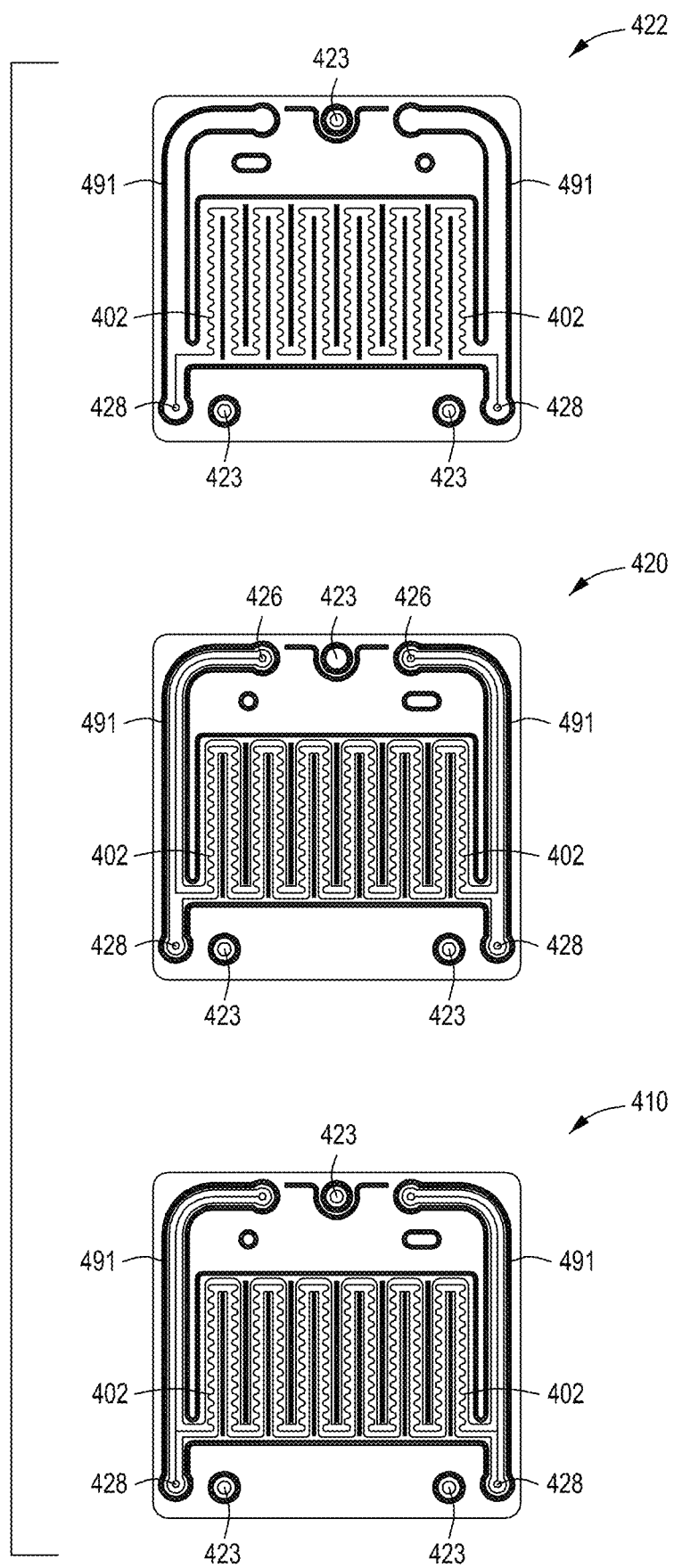
FIG. 4A depicts retentate (top) and permeate (middle) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422-specifically at retentate port 428-traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

At bottom of FIG. 4A is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 102 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

Figure 4B:
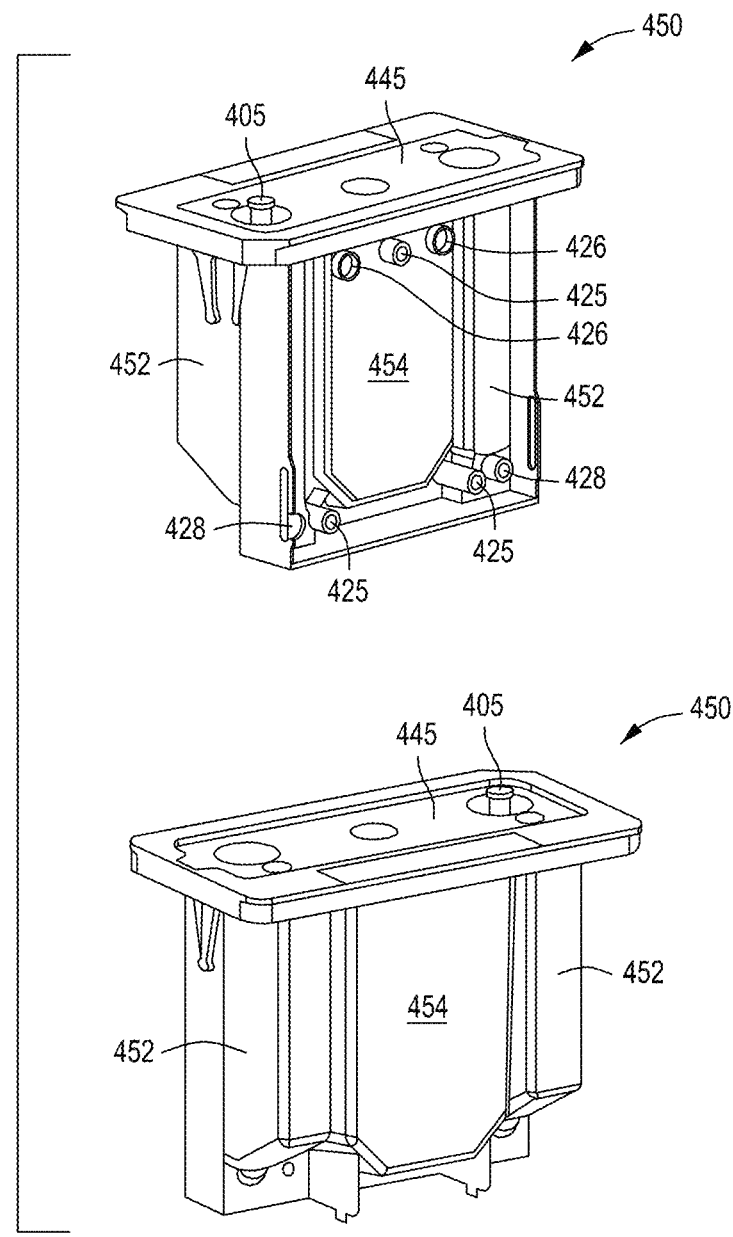
FIG. 4B depicts two side perspective views of a reservoir assembly of a tangential flow filtration module.

FIG. 4B shows front perspective (top) and rear perspective (bottom) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E. At left in FIG. 4B is a rear perspective view of reservoir assembly 450, where "rear" is the side of reservoir assembly 450 that is not coupled to the tangential flow assembly. Seen are retentate reservoirs 452, permeate reservoir 454, and gasket 445, where there is a pipette tip 405 inserted in one retentate reservoir 452.

The TFF device may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
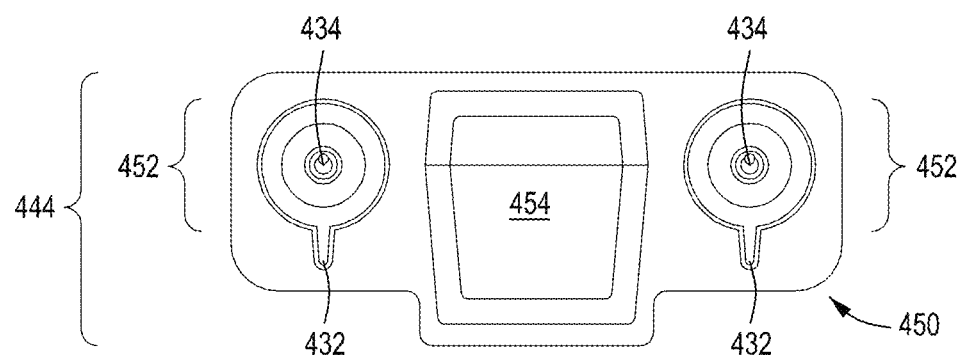
FIGS. 4C-4E depict an exemplary top, with fluidic and pneumatic ports and gasket suitable for the reservoir assemblies shown in FIG. 4B.
Figure 4D:
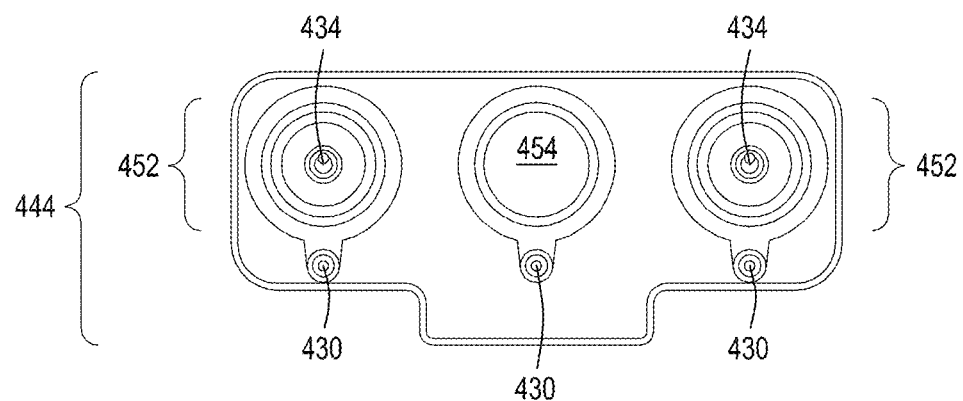
Figure 4E:
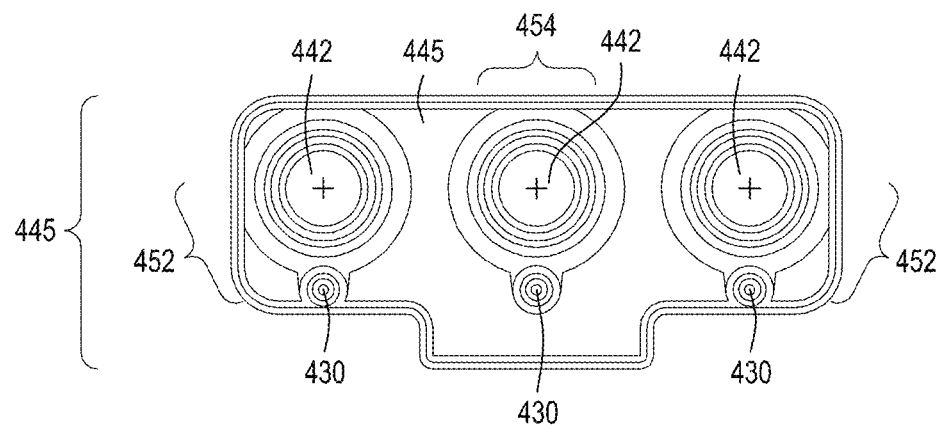

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configured to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 406, collecting the cell culture through a second retentate port 404 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicone photodiode. Generally, optical density is shown as the absolute value of the logarithm with base 10 of the power transmission factors of an optical attenuator: OD=−log 10 (Power out/Power in). Since OD is the measure of optical attenuation-that is, the sum of absorption, scattering, and reflection-the TFF device OD measurement records the overall power transmission, so as the cells grow and become denser in population, the OD (the loss of signal) increases. The OD system is pre-calibrated against OD standards with these values stored in an on-board memory accessible by the measurement program.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 406. Alternatively, cells can be grown in one reservoir with bubbling or agitation without passing the cells through the TFF channel from one reservoir to the other.

The overall workflow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 404, and the medium/buffer that has passed through the membrane is collected through one or both of the permeate/filtrate ports 406. All types of prokaryotic and eukaryotic cells-both adherent and non-adherent cells-can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as LB, SOC, TPD, YPG, YPAD, MEM, DMEM, IMDM, RPMI, Hanks', PBS and Ringer's solution, where the media may be provided in a reagent cartridge as part of a kit.

In both the cell growth and concentration processes, passing the cell sample through the TFF device and collecting the cells in one of the retentate ports 404 while collecting the medium in one of the permeate/filtrate ports 406 is considered "one pass" of the cell sample. The transfer between retentate reservoirs "flips" the culture. The retentate and permeate ports collecting the cells and medium, respectively, for a given pass reside on the same end of TFF device/module with fluidic connections arranged so that there are two distinct flow layers for the retentate and permeate/filtrate sides, but if the retentate port 404 resides on the retentate member of device/module (that is, the cells are driven through the channel above the membrane and the filtrate (medium) passes to the portion of the channel below the membrane), the permeate/filtrate port 406 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 404 and into the retentate reservoir (not shown). To initiate another "pass", the cell sample is passed again through the TFF device, this time in a flow direction that is reversed from the first pass. The cell sample is collected by passing through the retentate port 404 and into retentate reservoir (not shown) on the opposite end of the device/module from the retentate port 404 that was used to collect cells during the first pass. Likewise, the medium/buffer that passes through the membrane on the second pass is collected through the permeate port 406 on the opposite end of the device/module from the permeate port 406 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/798, 302, filed 22 Sep. 2020.

The Cell Transformation Module

Figure 5A:
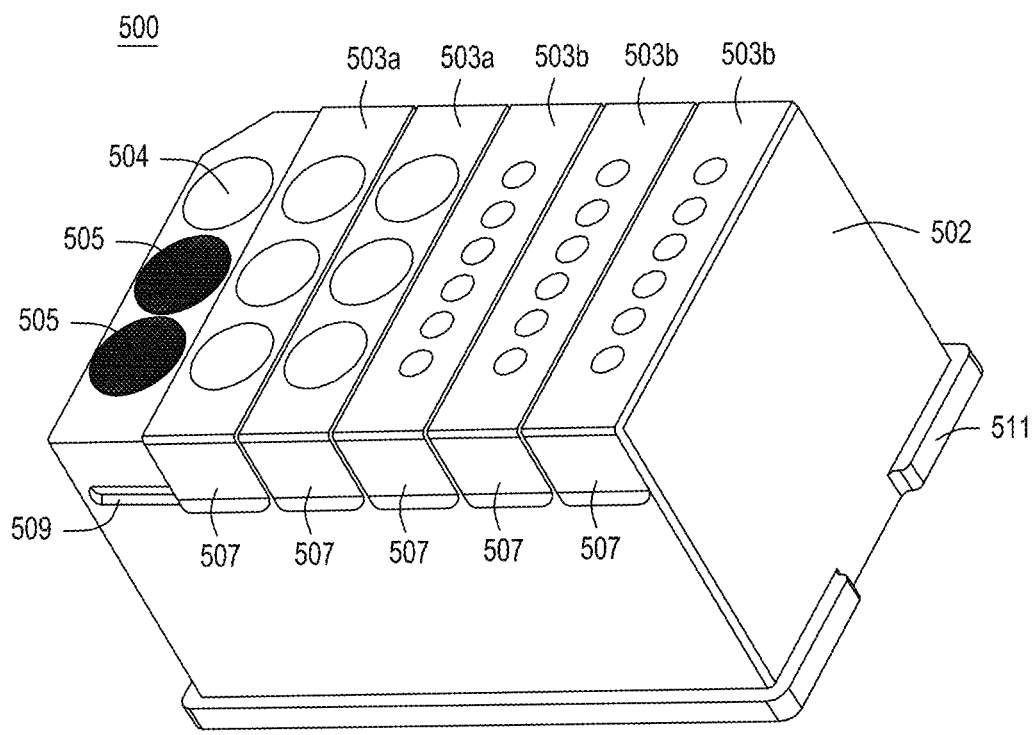
FIGS. 5A and 5B depict the structure and components of an embodiment of a reagent cartridge.
Figure 5B:
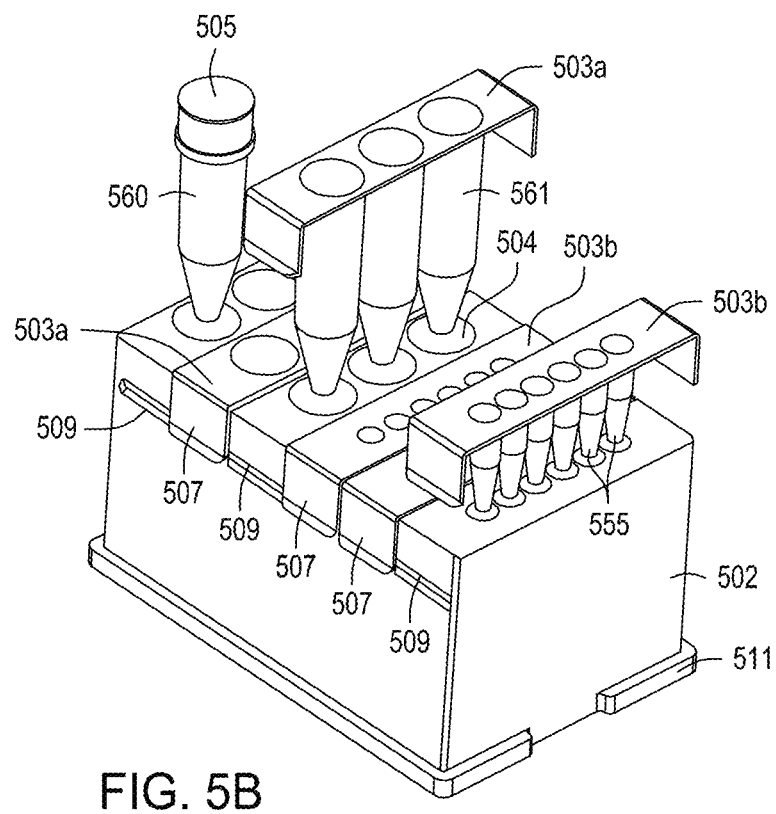

FIGS. 5A and 5B depict the structure and components of an embodiment of an exemplary reagent cartridge useful in the automated multi-module instrument described therein. In FIG. 5A, reagent cartridge 500 comprises a body 502, which has reservoirs 504. One reservoir 504 is shown empty, and two of the reservoirs have individual tubes (not shown) inserted therein, with individual tube covers 505. Additionally shown are rows of reservoirs into which have been inserted co-joined rows of large tubes 503a, and co-joined rows of small tubes 503b. The co-joined rows of tubes are presented in a strip, with outer flanges 507 that mate on the backside of the outer flange (not shown) with an indentation 509 in the body 502, so as to secure the co-joined rows of tubes (503a and 503b) to the reagent cartridge 500. Shown also is a base 511 of reagent cartridge body 502. Note that the reservoirs 504 in body 502 are shaped generally like the tubes in the co-joined tubes that are inserted into these reservoirs 504.

FIG. 5B depicts the reagent cartridge 500 in FIG. 5A with a row of co-joined large tubes 503a, a row of co-joined small tubes 503b, and one large tube 560 with a cover 505 removed from (i.e., depicted above) the reservoirs 504 of the reagent cartridge 500. Again, the co-joined rows of tubes are presented in a strip, with individual large tubes 561 shown, and individual small tubes 555 shown. Again, each strip of co-joined tubes comprises outer flanges 507 that mate on the backside (not shown) of the outer flange with an indentation 509 in the body 502, to secure the co-joined rows of tubes (503a and 503b) to the reagent cartridge 500. As in FIG. 5A, reagent cartridge body 502 comprises a base 511. Reagent cartridge 500 may be made from any suitable material, including stainless steel, aluminum, or plastics including polyvinyl chloride, cyclic olefin copolymer (COC), polyethylene, polyamide, polypropylene, acrylonitrile butadiene, polycarbonate, polyetheretheketone (PEEK), poly(methyl methylacrylate) (PMMA), polysulfone, and polyurethane, and co-polymers of these and other polymers. Again, if reagent cartridge 500 is disposable, it preferably is made of plastic. In addition, in many embodiments the material used to fabricate the cartridge is thermally-conductive, as reagent cartridge 500 may contact a thermal device (not shown) that heats or cools reagents in the reagent reservoirs 504, including reagents in co-joined tubes. In some embodiments, the thermal device is a Peltier device or thermoelectric cooler.

Figure 5C:
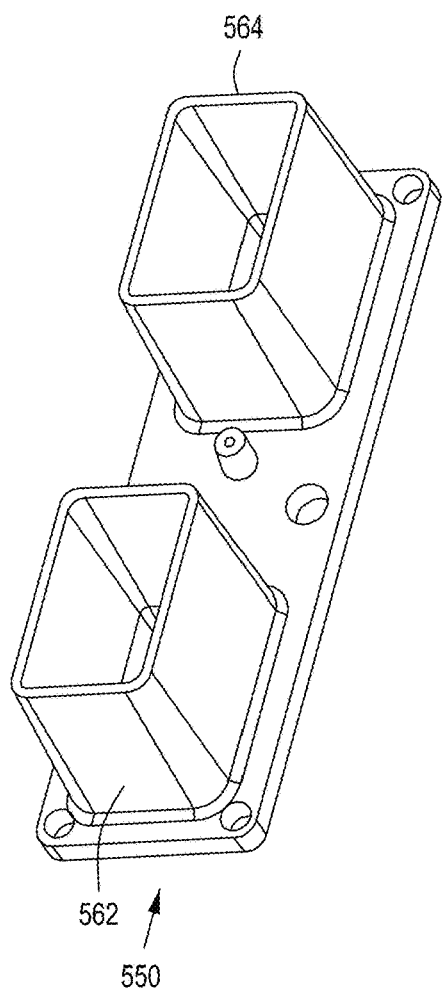
FIG. 5C is a top perspective view of one embodiment of an exemplary flow-through electroporation device that may be part of a reagent cartridge.
Figure 5D:
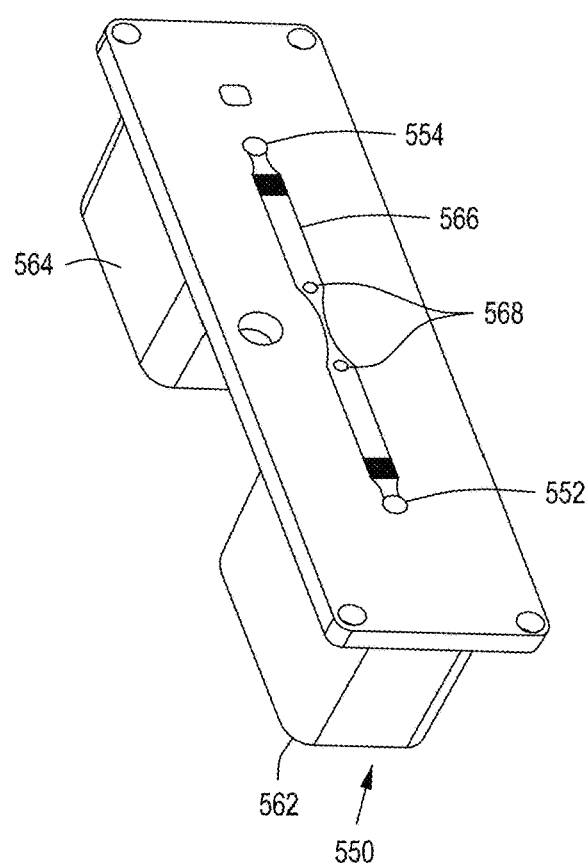
FIG. 5D depicts a bottom perspective view of one embodiment of an exemplary flow-through electroporation device that may be part of a reagent cartridge.

FIGS. 5C and 5D are top perspective and bottom perspective views, respectively, of an exemplary FTEP device 550 that may be part of (e.g., a component in) reagent cartridge 500 in FIGS. 5A and 5B or may be a stand-alone module; that is, not a part of a reagent cartridge or other module. FIG. 5C depicts an FTEP device 550. The FTEP device 550 has wells 562, 564 that define cell sample inlets 552 and cell sample outlets 554. FIG. 5D is a bottom perspective view of the FTEP device 550 of FIG. 5C. An inlet well 562 and an outlet well 564 can be seen in this view. Also seen in FIG. 5D are the bottom of an inlet 552 corresponding to well 562, the bottom of an outlet 554 corresponding to the outlet well 564, the bottom of a defined flow channel 566 and the bottom of two electrodes 568 on either side of flow channel 566. The FTEP devices may comprise push-pull pneumatic means to allow multi-pass electroporation procedures; that is, cells to electroporated may be "pulled" from the inlet toward the outlet for one pass of electroporation, then be "pushed" from the outlet end of the FTEP device toward the inlet end to pass between the electrodes again for another pass of electroporation. Further, this process may be repeated one to many times. For additional information regarding FTEP devices, see, e.g., U.S. Pat. Nos. 10,435,713; 10,443,074; 10,323,258; and 10,508,288. Further, other embodiments of the reagent cartridge may provide or accommodate electroporation devices that are not configured as FTEP devices, such as those described in U.S. Ser. No. 16/109,156, filed 22 Aug. 2018. For reagent cartridges useful in the present automated multi-module cell processing instruments, see, e.g., U.S. Pat. Nos. 10,376,889; 10,406,525; 10,576,474; and U.S. Ser. No. 16/749,757, filed 22 Jan. 2020; and Ser. No. 16/827,222, filed 23 Mar. 2020.

Figure 5E:
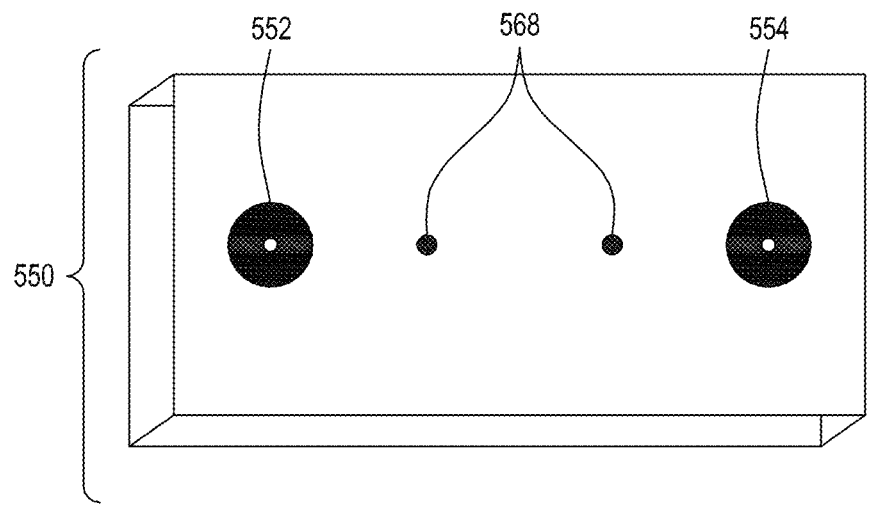
FIGS. 5E-5G depict a top perspective view, a top view of a cross section, and a side perspective view of a cross section of an FTEP device useful in a multi-module automated cell processing instrument such as that shown in FIGS. 2A-2C.
Figure 5F:
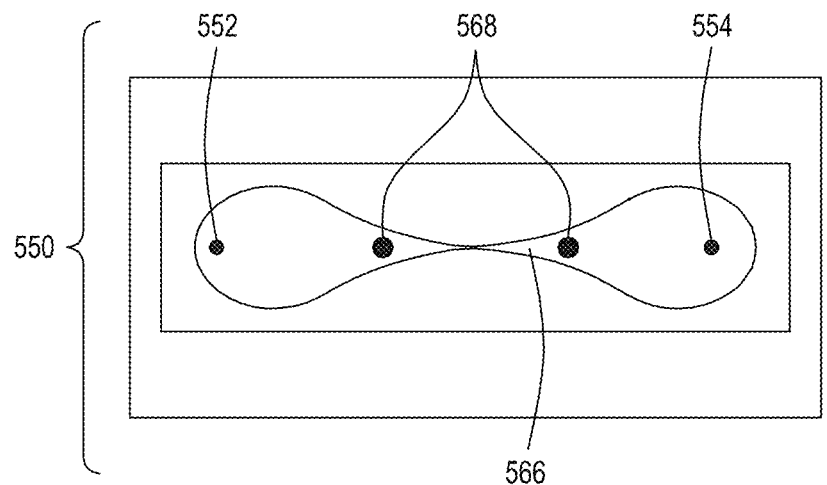
Figure 5G:
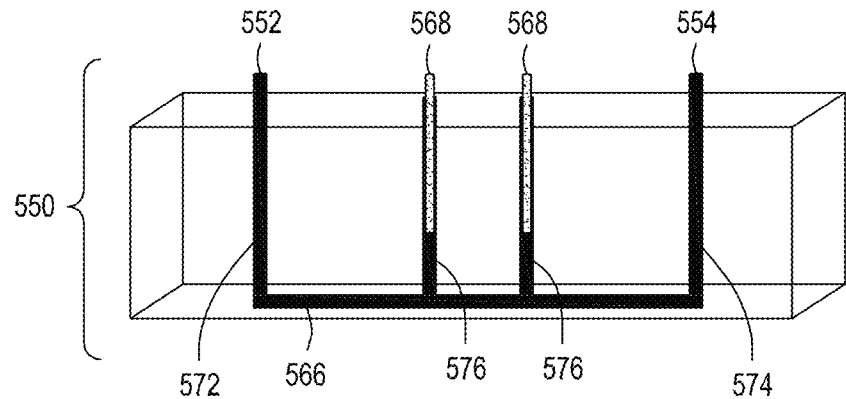

Additional details of the FTEP devices are illustrated in FIGS. 5E-5G. Note that in the FTEP devices in FIGS. 5E-5G the electrodes are placed such that a first electrode is placed between an inlet and a narrowed region of the flow channel, and the second electrode is placed between the narrowed region of the flow channel and an outlet. FIG. 5E shows a top planar view of an FTEP device 550 having an inlet 552 for introducing a fluid containing cells and exogenous material into FTEP device 550 and an outlet 554 for removing the transformed cells from the FTEP following electroporation. The electrodes 568 are introduced through channels (not shown) in the device. FIG. 5F shows a cutaway view from the top of the FTEP device 550, with the inlet 552, outlet 554, and electrodes 568 positioned with respect to a flow channel 566. FIG. 5G shows a side cutaway view of FTEP device 550 with the inlet 552 and inlet channel 572, and outlet 554 and outlet channel 574. The electrodes 568 are positioned in electrode channels 576 so that they are in fluid communication with the flow channel 566, but not directly in the path of the cells traveling through the flow channel 566. Note that the first electrode is placed between the inlet and the narrowed region of the flow channel, and the second electrode is placed between the narrowed region of the flow channel and the outlet. The electrodes 568 in this aspect of the device are positioned in the electrode channels 576 which are generally perpendicular to the flow channel 566 such that the fluid containing the cells and exogenous material flows from the inlet channel 572 through the flow channel 566 to the outlet channel 574, and in the process fluid flows into the electrode channels 576 to be in contact with the electrodes 568. In this aspect, the inlet channel, outlet channel and electrode channels all originate from the same planar side of the device. In certain aspects, however, the electrodes may be introduced from a different planar side of the FTEP device than the inlet and outlet channels.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 508 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired-as opposed to a disposable, one-use flow-through FTEP device-the electrode plates can be coated with metals resistant to electrochemical corrosion. Conductive coatings like noble metals, e.g., gold, can be used to protect the electrode plates.

As mentioned, the FTEP devices may comprise push-pull pneumatic means to allow multi-pass electroporation procedures; that is, cells to be electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, where the flow channel decreases in width, the flow channel may narrow to between 10 µm and 5 mm, or between 25 µm and 3 mm, or between 50 µm and 2 mm, or between 75 µm and 1 mm. The distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is wide enough so that at least two cells can fit in the narrowed portion side-by-side. For example, a typical bacterial cell is 1 µm in diameter; thus, the narrowed portion of the flow channel of the FTEP device used to transform such bacterial cells will be at least 2 µm wide. In another example, if a mammalian cell is approximately 50 µm in diameter, the narrowed portion of the flow channel of the FTEP device used to transform such mammalian cells will be at least 100 µm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 µL to 10 mL, or from 500 µL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 µm are preferred. In another embodiment of the invention, the flow-through electroporation device comprises at least one additional electrode which applies a ground potential to the FTEP device. Flow-through electroporation devices (either as a stand-alone instrument or as a module in an automated multi-module system) are described in, e.g., U.S. Pat. Nos. 10,435,713; 10,443,074; 10,323,258; and 10,508,288.

Cell Singulation and Enrichment Device

Figure 6A:
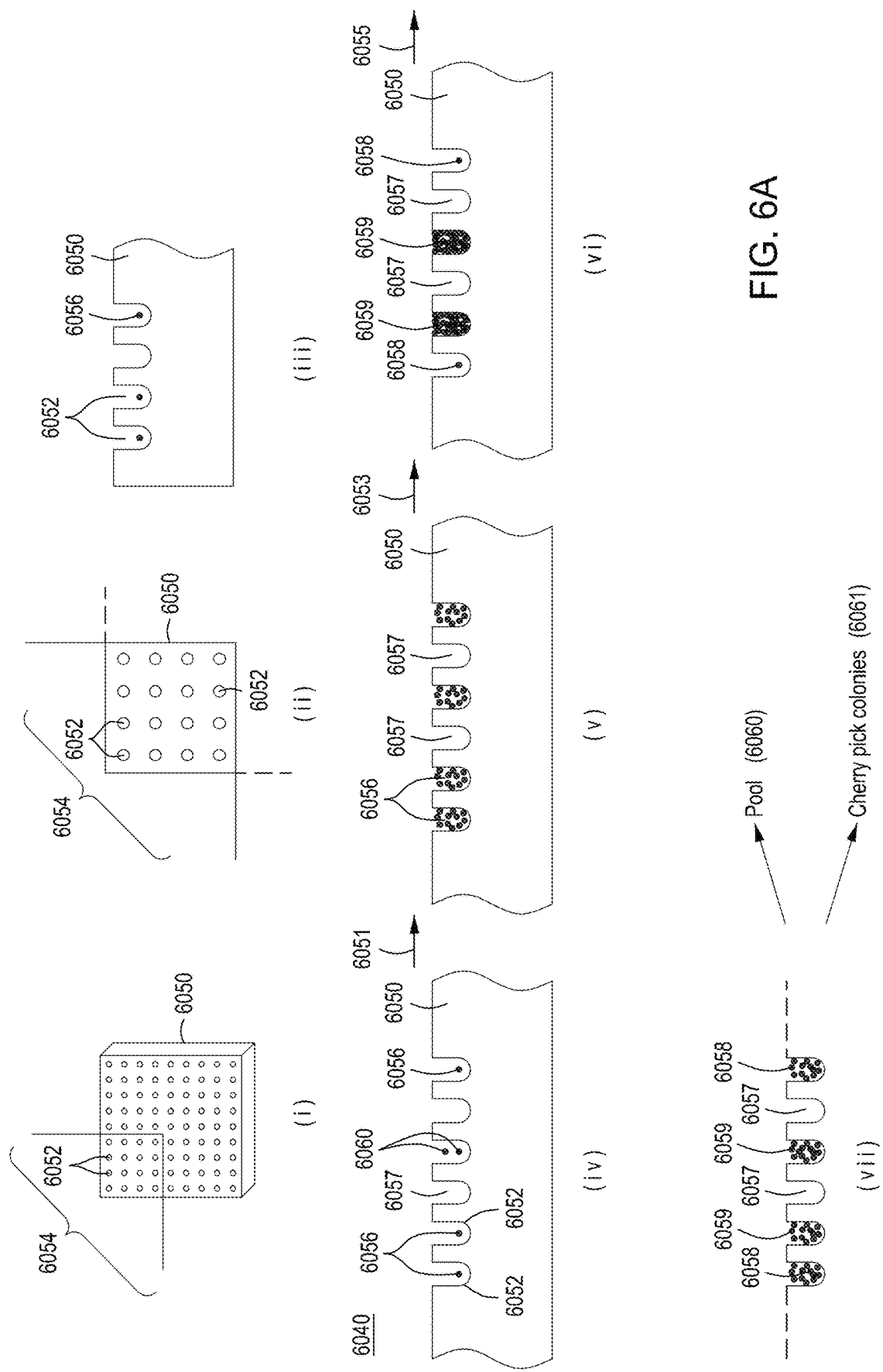
FIG. 6A depicts a simplified graphic of a workflow for singulating, editing and normalizing cells in a solid wall device.

FIG. 6A depicts a solid wall device 6050 and a workflow for singulating cells in microwells in the solid wall device. At the top left of the figure (i), there is depicted solid wall device 6050 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, Poisson or substantial Poisson loading has taken place; that is, each microwell has one or no cells, and the likelihood that any one microwell has more than one cell is low. At (iv), workflow 6040 is illustrated where substrate 6050 having microwells 6052 shows microwells 6056 with one cell per microwell, microwells 6057 with no cells in the microwells, and one microwell 6060 with two cells in the microwell. In step 6051, the cells in the microwells are allowed to double approximately 2-150 times to form clonal colonies (v), then editing is allowed to occur 6053.

After editing 6053, many cells in the colonies of cells that have been edited die as a result of the double-strand cuts caused by active editing and there is a lag in growth for the edited cells that do survive but must repair and recover following editing (microwells 6058), where cells that do not undergo editing thrive (microwells 6059) (vi). All cells are allowed to continue grow to establish colonies and normalize, where the colonies of edited cells in microwells 6058 catch up in size and/or cell number with the cells in microwells 6059 that do not undergo editing (vii). Once the cell colonies are normalized, either pooling 6060 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6058) are identified and selected 6061 (e.g., "cherry picked") resulting in even greater enrichment of edited cells.

In growing the cells, the medium used will depend, of course, on the type of cells being edited-e.g., bacterial, yeast or mammalian. For example, medium for yeast cell growth includes LB, SOC, TPD, YPG, YPAD, MEM and DMEM.

Figure 6B:
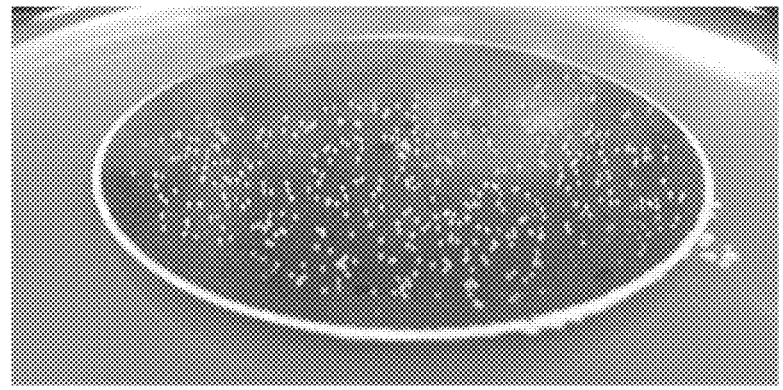
FIG. 6B is a photograph of a solid wall device with a permeable bottom on agar, on which yeast cells have been singulated and grown into clonal colonies.
Figure 6C:
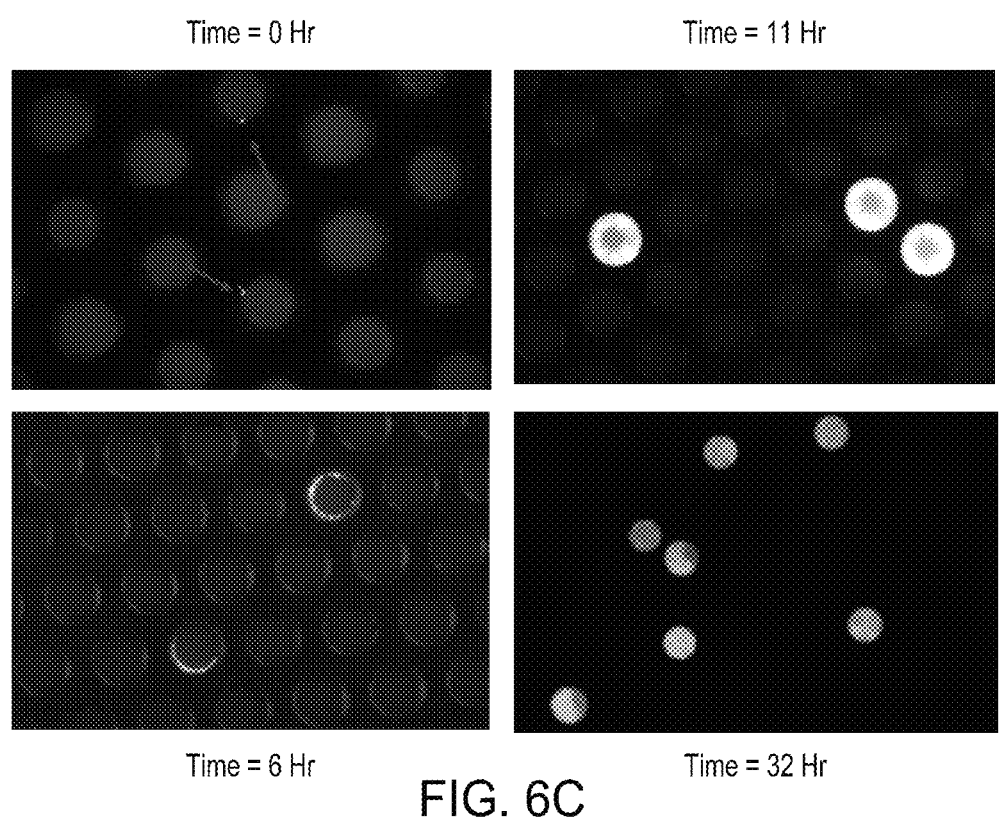
FIG. 6C presents photographs of yeast colony growth at various time points.

FIG. 6B is a photograph of one embodiment of a SWIIN. FIG. 6B is a photograph of a SWIIN device with a permeable bottom on agar, on which yeast cells have been singulated and grown into clonal colonies. FIG. 6C presents photographs of yeast colony growth in a SWIIN at various time points (at 0, 6, 11 and 32 hours).

Figure 6D:
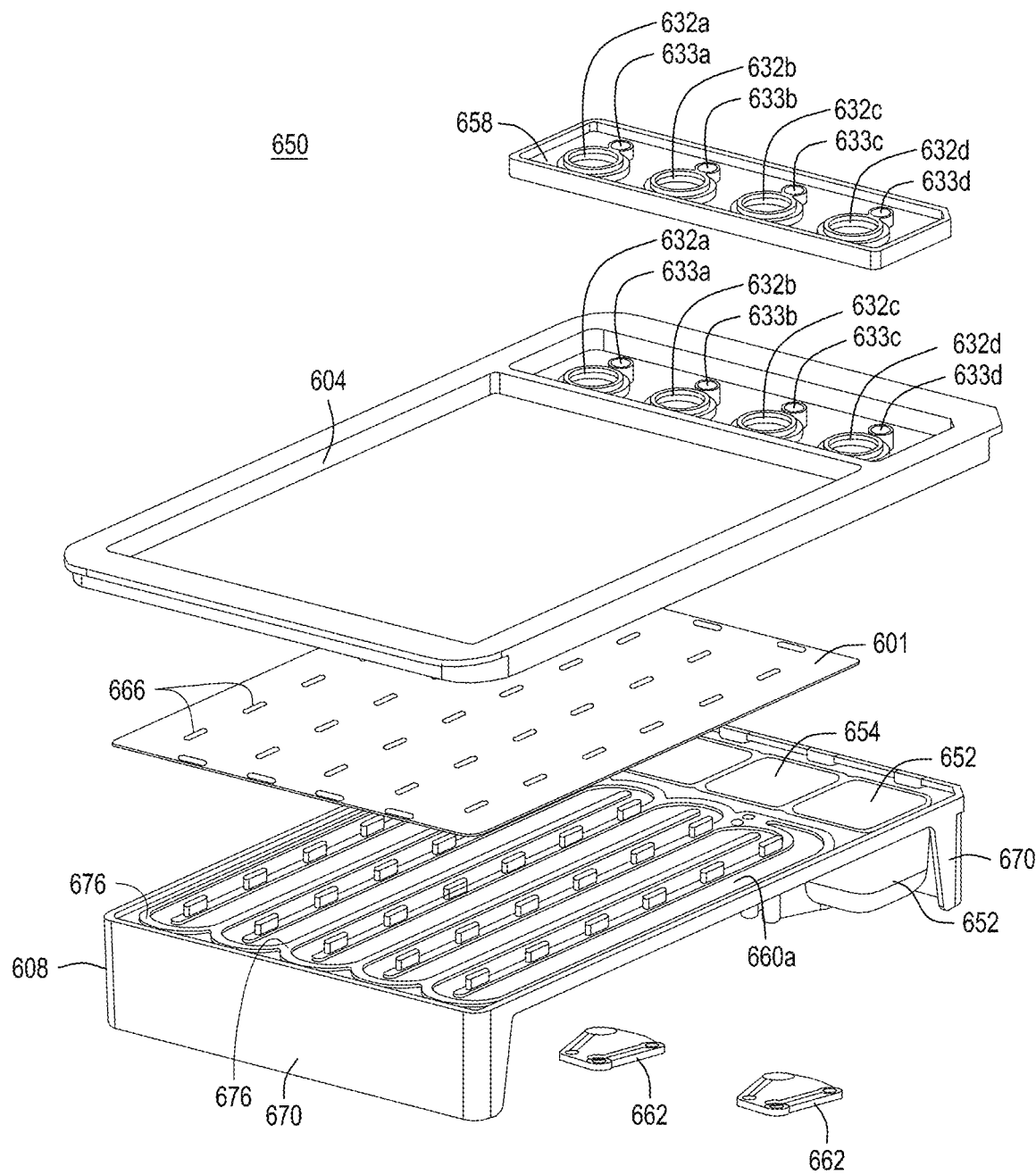
FIGS. 6D-6F depict an embodiment of a solid wall isolation incubation and normalization (SWIIN) module.

A module useful for performing the methods depicted in FIG. 6A is a solid wall isolation, incubation, and normalization (SWIIN) module. FIG. 6D depicts an embodiment of a SWIIN module 650 from an exploded top perspective view. In SWIIN module 650 the retentate member is formed on the bottom of a top of a SWIIN module component and the permeate member is formed on the top of the bottom of a SWIIN module component.

The SWIIN module 650 in FIG. 6D comprises from the top down, a reservoir gasket or cover 658, a retentate member 604 (where a retentate flow channel cannot be seen in this FIG. 6D), a perforated member 601 swaged with a filter (filter not seen in FIG. 6D), a permeate member 608 comprising integrated reservoirs (permeate reservoirs 652 and retentate reservoirs 654), and two reservoir seals 662, which seal the bottom of permeate reservoirs 652 and retentate reservoirs 654. A permeate channel 660a can be seen disposed on the top of permeate member 608, defined by a raised portion 676 of serpentine channel 660a, and ultrasonic tabs 664 can be seen disposed on the top of permeate member 608 as well. The perforations that form the wells on perforated member 601 are not seen in this FIG. 6D; however, through-holes 666 to accommodate the ultrasonic tabs 664 are seen. In addition, supports 670 are disposed at either end of SWIIN module 650 to support SWIIN module 650 and to elevate permeate member 608 and retentate member 604 above reservoirs 652 and 654 to minimize bubbles or air entering the fluid path from the permeate reservoir to serpentine channel 660a or the fluid path from the retentate reservoir to serpentine channel 660b (neither fluid path is seen in this FIG. 6D).

In this FIG. 6D, it can be seen that the serpentine channel 660a that is disposed on the top of permeate member 608 traverses permeate member 608 for most of the length of permeate member 608 except for the portion of permeate member 608 that comprises permeate reservoirs 652 and retentate reservoirs 654 and for most of the width of permeate member 608. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 µm-200 µm in diameter, and the perforated member is approximately 125 µm deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 660a and 660b can have approximately the same volume or a different volume. For example, each "side" or portion 660a, 660b of the serpentine channel may have a volume of, e.g., 2 mL, or serpentine channel 660a of permeate member 608 may have a volume of 2 mL, and the serpentine channel 660b of retentate member 604 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 660a and 660b of the permeate member 608 and retentate member 604, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 6G and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Automated colony pickers may be employed, such as those sold by, e.g., TECAN (Pickolo™ system, Mannedorf, Switzerland); Hudson Inc. (RapidPick™ Springfield, N.J.); Molecular Devices (QPix 400™ system, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 650 may be controlled by, e.g., moving heated air over the top of (e.g., retentate member) of the SWIIN module 650, or by applying a transparent heated lid over at least the serpentine channel portion 660b of the retentate member 604. See, e.g., FIG. 6G and the description thereof infra.

In SWIIN module 650 cells and medium-at a dilution appropriate for Poisson or substantial Poisson distribution of the cells in the microwells of the perforated member-are flowed into serpentine channel 660b from ports in retentate member 604, and the cells settle in the microwells while the medium passes through the filter into serpentine channel 660a in permeate member 608. The cells are retained in the microwells of perforated member 601 as the cells cannot travel through filter 603. Appropriate medium may be introduced into permeate member 608 through permeate ports 611. The medium flows upward through filter 603 to nourish the cells in the microwells (perforations) of perforated member 601. Additionally, buffer exchange can be effected by cycling medium through the retentate and permeate members. In operation, the cells are deposited into the microwells, are grown for an initial, e.g., 2-100 doublings, editing may be induced by, e.g., raising the temperature of the SWIIN to 42° C. to induce a temperature-inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 650 until the growth of the cell colonies in the microwells is normalized. For the normalization protocol, once the colonies are normalized, the colonies are flushed from the microwells by applying fluid or air pressure (or both) to the permeate member serpentine channel 660a and thus to filter 603 and pooled. Alternatively, if cherry picking is desired, the growth of the cell colonies in the microwells is monitored, and slow-growing colonies are directly selected; or, fast-growing colonies are eliminated.

Figure 6E:
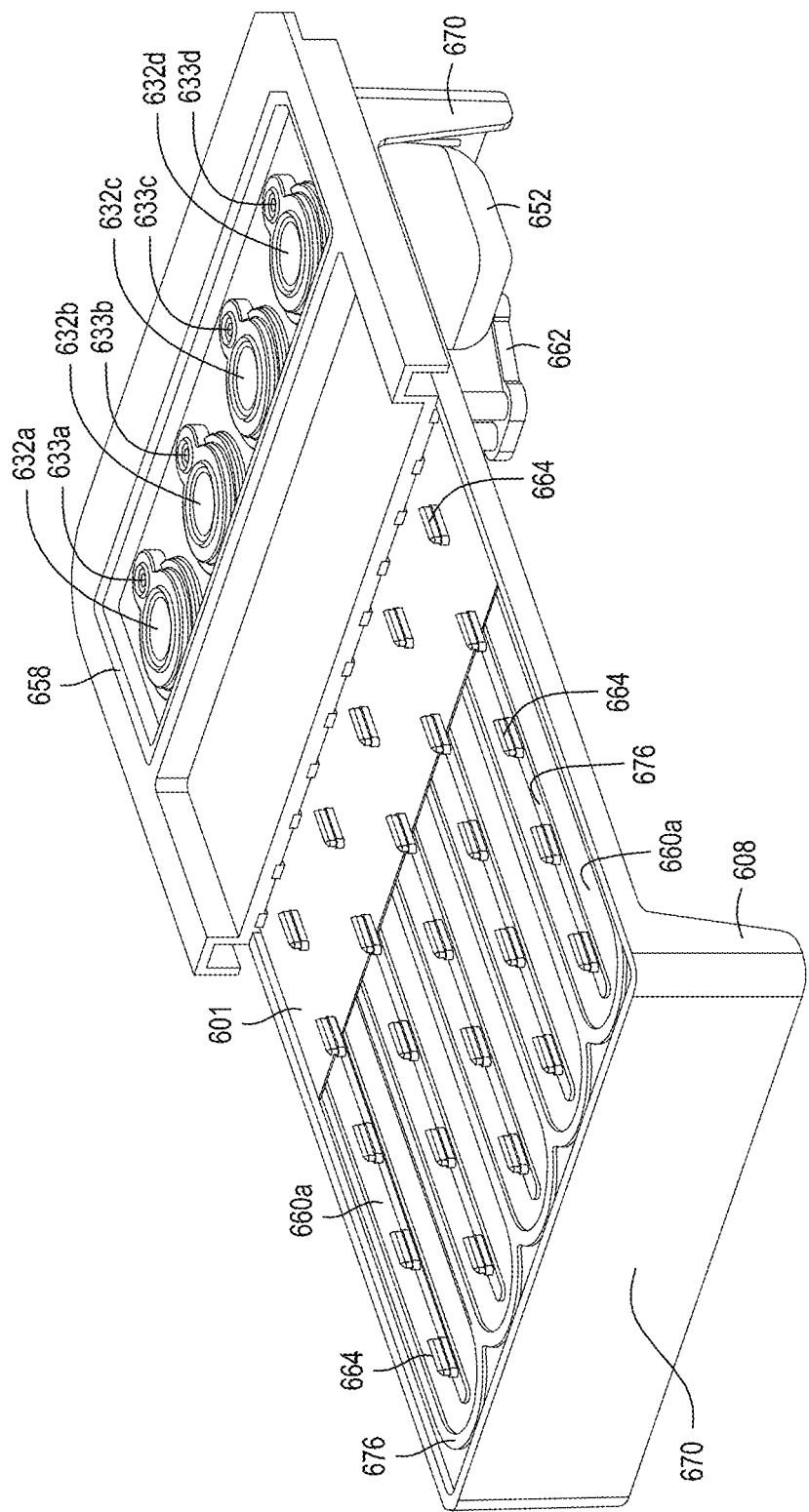

FIG. 6E is a top perspective view of a SWIIN module with the retentate and perforated members in partial cross section. In this FIG. 6E, it can be seen that serpentine channel 660a is disposed on the top of permeate member 608 is defined by raised portions 676 and traverses permeate member 608 for most of the length and width of permeate member 608 except for the portion of permeate member 608 that comprises the permeate and retentate reservoirs (note only one retentate reservoir 652 can be seen). Moving from left to right, reservoir gasket 658 is disposed upon the integrated reservoir cover 678 (cover not seen in this FIG. 6E) of retentate member 604. Gasket 658 comprises reservoir access apertures 632a, 632b, 632c, and 632d, as well as pneumatic ports 633a, 633b, 633c and 633d. Also at the far left end is support 670. Disposed under permeate reservoir 652 can be seen one of two reservoir seals 662. In addition to the retentate member being in cross section, the perforated member 601 and filter 603 (filter 603 is not seen in this FIG. 6E) are in cross section. Note that there are a number of ultrasonic tabs 664 disposed at the right end of SWIIN module 650 and on raised portion 676 which defines the channel turns of serpentine channel 660a, including ultrasonic tabs 664 extending through through-holes 666 of perforated member 601. There is also a support 670 at the end distal reservoirs 652, 654 of permeate member 608.

Figure 6F:
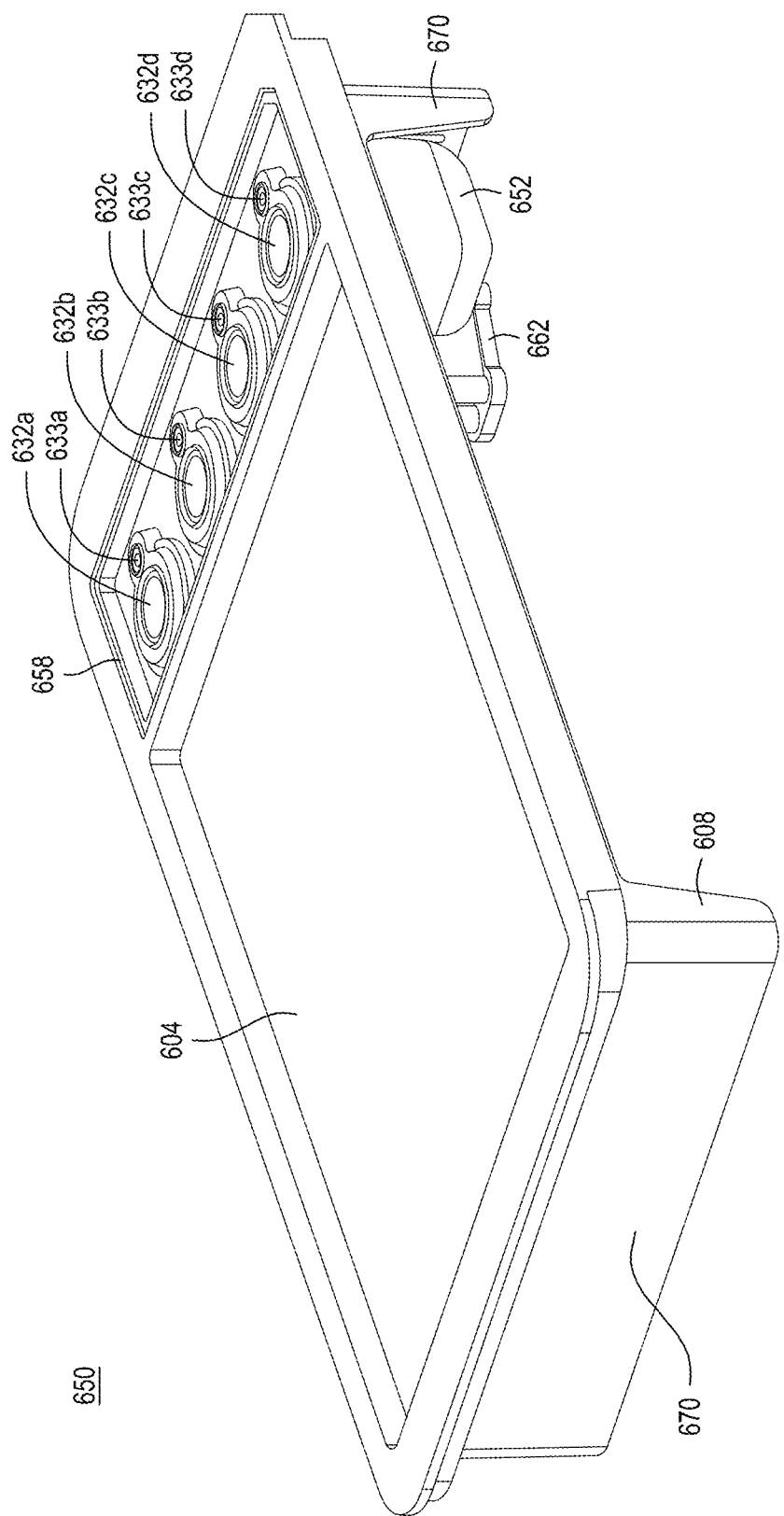

FIG. 6F is a side perspective view of an assembled SWIIIN module 650, including, from right to left, reservoir gasket 658 disposed upon integrated reservoir cover 678 (not seen) of retentate member 604. Gasket 658 may be fabricated from rubber, silicone, nitrile rubber, polytetrafluoroethylene, a plastic polymer such as polychlorotrifluoroethylene, or other flexible, compressible material. Gasket 658 comprises reservoir access apertures 632a, 632b, 632c, and 632d, as well as pneumatic ports 633a, 633b, 633c and 633d. Also at the far-left end is support 670 of permeate member 608. In addition, permeate reservoir 652 can be seen, as well as one reservoir seal 662. At the far-right end is a second support 670.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 660.

Figure 6G:
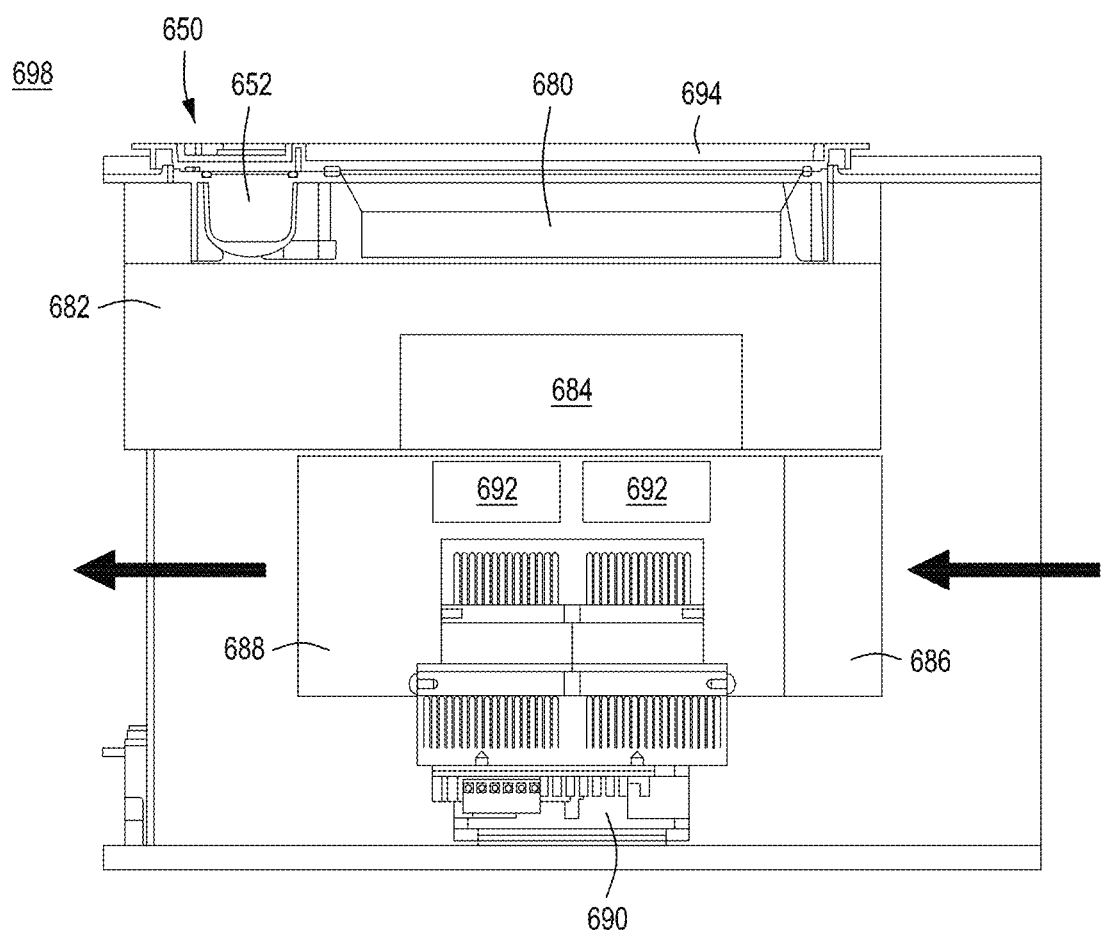
FIG. 6G depicts the embodiment of the SWIIN module in FIGS. 6D-6F further comprising a heater and a heated cover.

FIG. 6G depicts the embodiment of the SWIIN module in FIGS. 6D-6F further comprising a heat management system including a heater and a heated cover. The heater cover facilitates the condensation management that is required for imaging. Assembly 698 comprises a SWIIN module 650 seen lengthwise in cross section, where one permeate reservoir 652 is seen. Disposed immediately upon SWIIN module 650 is cover 694 and disposed immediately below SWIIN module 650 is backlight 680, which allows for imaging. Beneath and adjacent to the backlight and SWIIN module is insulation 682, which is disposed over a heatsink 684. In this FIG. 6G, the fins of the heatsink would be in-out of the page. In addition there is also axial fan 686 and heat sink 688, as well as two thermoelectric coolers 692, and a controller 690 to control the pneumatics, thermoelectric coolers, fan, solenoid valves, etc. The arrows denote cool air coming into the unit and hot air being removed from the unit. It should be noted that control of heating allows for growth of many different types of cells as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Pat. Nos. 10,533,152; 10,550,363; 10,532,324; 10,625,212; and U.S. Ser. Nos. 16/597,826, filed 19 Oct. 2019; Ser. No. 16/597,831, filed 9 Oct. 2019; Ser. No. 16/693,630, filed 25 Nov. 2019; and Ser. No. 16/686,066, filed 15 Nov. 2019.

Use of the Automated Multi-Module Yeast Cell Processing Instrument

Figure 7:
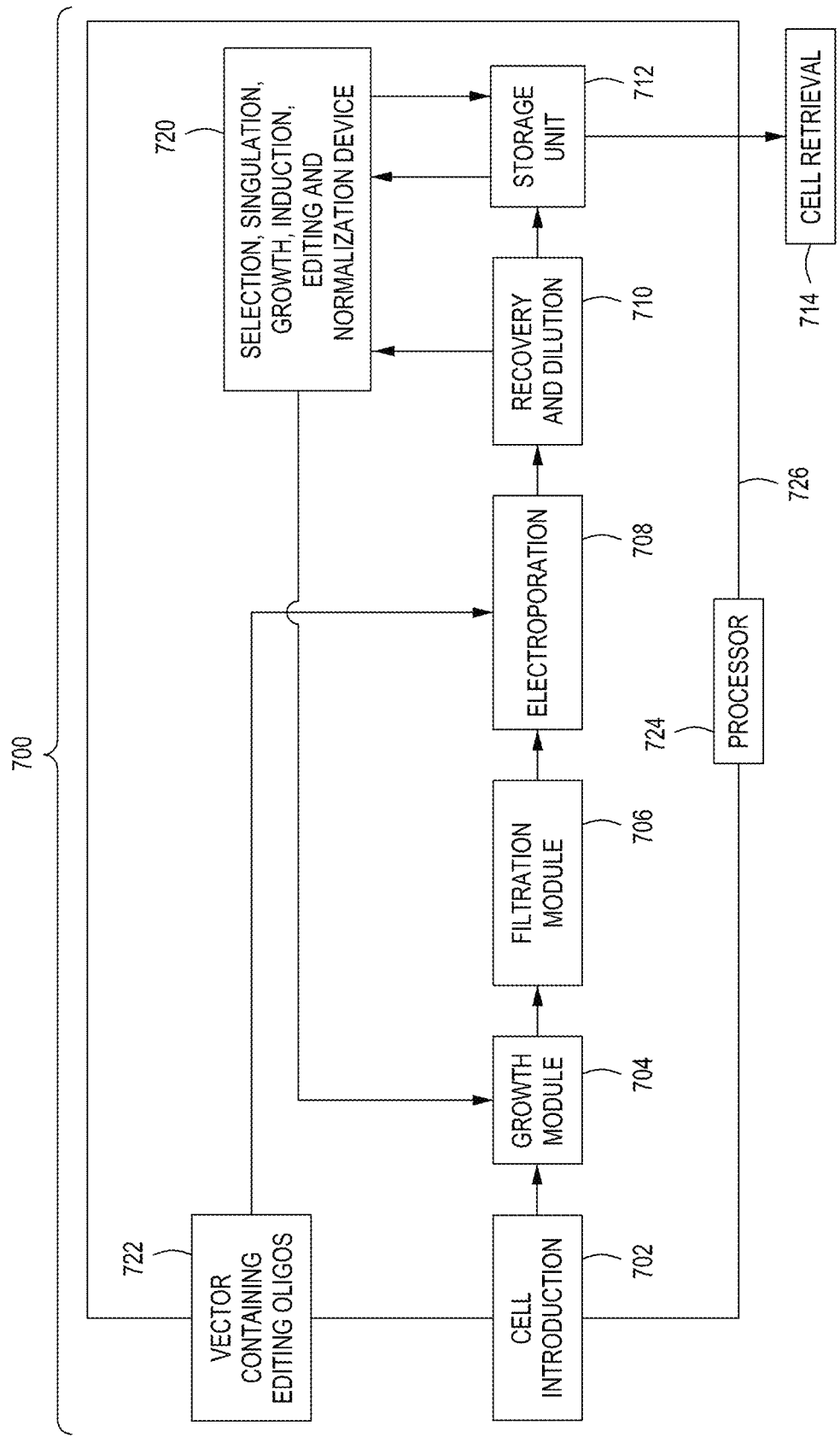
FIG. 7 is a simplified block diagram of an embodiment of an exemplary automated multi-module cell processing instrument comprising a solid wall singulation/growth/editing/normalization module for recursive yeast cell editing.

FIG. 7 illustrates an embodiment of a multi-module cell processing instrument. This embodiment depicts an exemplary system that performs recursive gene editing on a yeast cell population. The cell processing instrument 700 may include a housing 726, a reservoir for storing cells to be transformed or transfected 702, and a cell growth module (comprising, e.g., a rotating growth vial) 704. The cells to be transformed are transferred from a reservoir to the cell growth module to be cultured until the cells hit a target OD. Once the cells hit the target OD, the growth module may cool or freeze the cells for later processing or transfer the cells to a cell concentration/filtration module 706 where the cells are subjected to buffer exchange and rendered electrocompetent, and the volume of the cells may be reduced substantially. Once the cells have been concentrated to an appropriate volume, the cells are transferred to electroporation device 708. In addition to the reservoir for storing cells 702, the multi-module cell processing instrument includes a reservoir for storing the vector pre-assembled with editing oligonucleotide cassettes 722. The pre-assembled nucleic acid vectors are transferred to the electroporation device 708, which already contains the cell culture grown to a target OD. In the electroporation device 708, the nucleic acids are electroporated into the cells. Following electroporation, the cells are transferred into a recovery and dilution module 710, where the cells recover briefly post-transformation.

After recovery, the cells may be transferred to a storage module 712, where the cells can be stored at, e.g., 4° C. for later processing, the cells may be transferred to a reservoir for cell retrieval 714, or the cells may be diluted and transferred to a selection/singulation/growth/induction/editing/normalization (SWIIN) module 720. In the SWIIN 720, the cells are arrayed such that there is an average of one cell per microwell. The arrayed cells may be in selection medium to select for cells that have been transformed or transfected with the editing vector(s). Once singulated, in one embodiment the cells grow through 2-50 doublings and establish colonies. Once colonies are established, editing is induced by providing conditions (e.g., temperature, addition of an inducing or repressing chemical) to induce editing. Editing is then initiated and allowed to proceed, the cells are allowed to grow to terminal size (e.g., normalization of the colonies) in the microwells and then are treated to conditions that cure the editing vector from this round. In another embodiment editing is not induced and the cells are grown, allowed to edit, recover and normalize, and optionally cure.

Once cured, the cells can be flushed out of the microwells and pooled, then transferred to the storage (or recovery) unit 712 or can be transferred back to the growth module 704 for another round of editing. In between pooling and transfer to a growth module, there typically is one or more additional steps, such as cell recovery, medium exchange (rendering the cells electrocompetent), cell concentration (typically concurrently with medium exchange by, e.g., filtration. Note that the selection/singulation/growth/induction/editing/normalization modules may be the same module, where all processes are performed in, e.g., a solid wall device, or selection and/or dilution may take place in a separate vessel before the cells are transferred to the solid wall singulation/growth/induction/editing/normalization/editing module (SWIIN). Similarly, the cells may be pooled after normalization, transferred to a separate vessel, and cured in the separate vessel. As an alternative to singulation in, e.g., a solid wall device, the transformed cells may be grown in- and editing can be induced in-bulk liquid as described in U.S. Ser. No. 16/399,988, filed 30 Apr. 2019. Once the putatively-edited cells are pooled, they may be subjected to another round of editing, beginning with growth, cell concentration and treatment to render electrocompetent, and transformation by yet another donor nucleic acid in another editing cassette via the electroporation module 708.

In electroporation device 708, the yeast cells selected from the first round of editing are transformed by a second set of editing oligos (or other type of oligos) and the cycle is repeated until the cells have been transformed and edited by a desired number of, e.g., editing cassettes. The multi-module cell processing instrument exemplified in FIG. 7 is controlled by a processor 724 configured to operate the instrument based on user input or is controlled by one or more scripts including at least one script associated with the reagent cartridge. The processor 724 may control the timing, duration, and temperature of various processes, the dispensing of reagents, and other operations of the various modules of the instrument 700. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 7, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells.

Curing can be accomplished by, e.g., cleaving the vector(s) using a curing plasmid thereby rendering the editing and/or engine vector (or single, combined engine/editing vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine vector.

Figure 8:
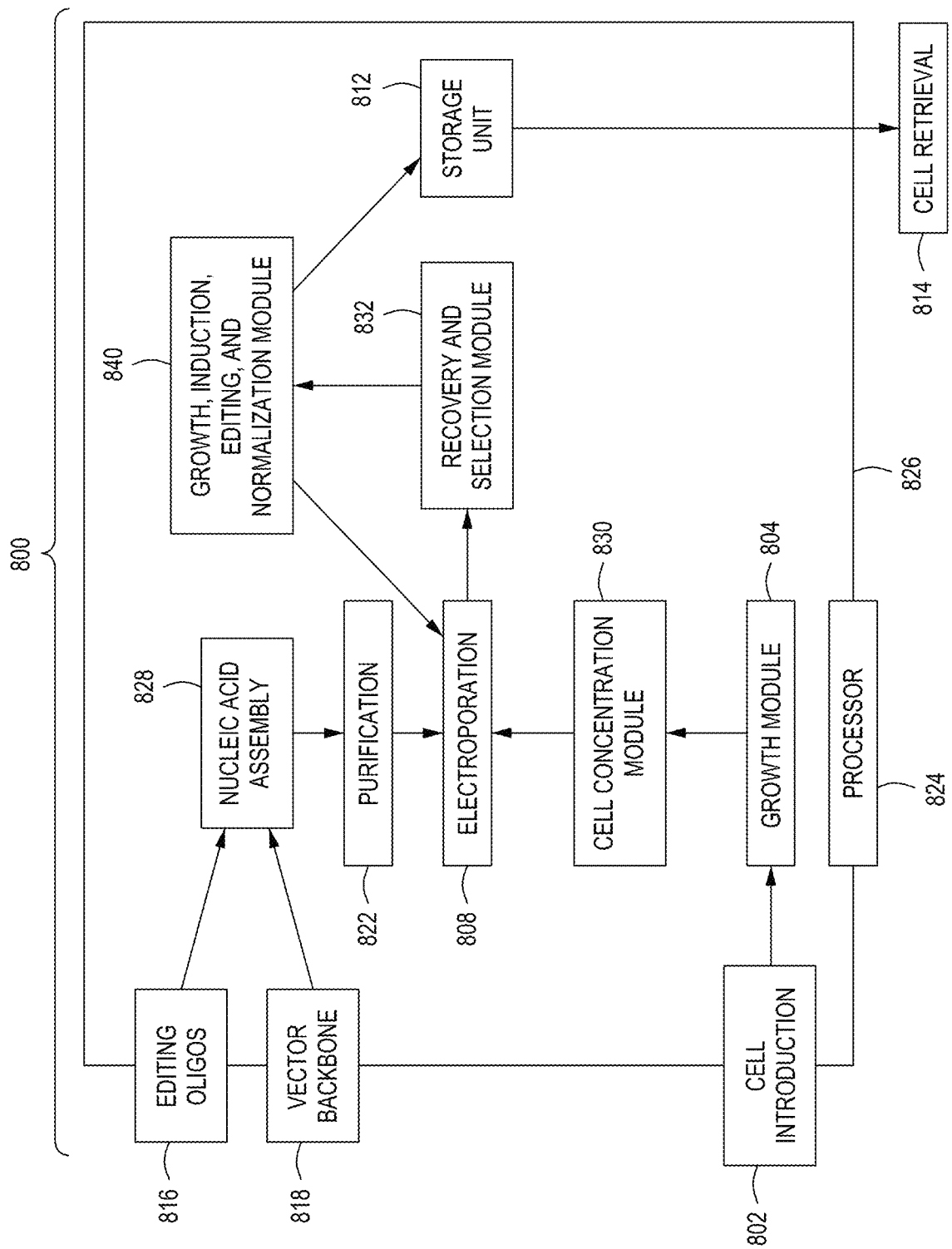
FIG. 8 is a simplified process diagram of an alternative embodiment of an exemplary automated multi-module cell processing instrument useful for recursive yeast cell editing.

FIG. 8 is a simplified block diagram of an embodiment of an exemplary automated multi-module cell processing instrument comprising an isolation, induction, editing, and normalization module such as a SWIIN, or just by dilute plating on a solid substrate. The cell processing instrument 800 may include a housing 826, a reservoir of cells to be transformed or transfected 802, and a growth module (a cell growth device) 804. The cells to be transformed are transferred from a reservoir to the growth module to be cultured until the cells hit a target OD. Once the cells hit the target OD, the growth module may cool or freeze the cells for later processing, or the cells may be transferred to a cell concentration/filtration module 830 where the cells are rendered electrocompetent and concentrated to a volume optimal for cell transformation. Once concentrated, the cells are then transferred to an electroporation device 808 (e.g., transformation/transfection module).

In addition to the reservoir for storing the cells, the system 800 may include a reservoir for storing editing cassettes 816 and a reservoir for storing an expression vector backbone 818. Both the editing oligonucleotide cassettes and the expression vector backbone are transferred from the reagent cartridge to a nucleic acid assembly module 828, where the editing oligonucleotide cassettes are inserted into the expression vector backbone. The assembled nucleic acids may be transferred into an optional purification module 822 for desalting and/or other purification and/or concentration procedures needed to prepare the assembled nucleic acids for transformation. Alternatively, pre-assembled nucleic acids, e.g., an editing vector, may be stored within reservoir 816 or 818. Once the processes carried out by the purification module 822 are complete, the assembled nucleic acids are transferred to, e.g., an electroporation device 808, which already contains the cell culture grown to a target OD and rendered electrocompetent via concentration module 830. In electroporation device 808, the assembled nucleic acids are introduced into the cells. Following electroporation, the cells are transferred into a combined recovery/selection module 832. For examples of multi-module cell editing instruments, see U.S. Pat. Nos. 10,253,316; 10,329,559; 10,323,242; 10,421,959; 10,465,185; 10,519,437; 10,584,333; and 10,584,334; and U.S. Ser. No. 16/750,369, filed 23 Jan. 2020; Ser. No. 16/822,249, filed 18 Mar. 2020; and Ser. No. 16/837,985, filed 1 Apr. 2020, all of which are herein incorporated by reference in their entirety.

Following recovery, and, optionally, selection, the cells are transferred to a growth, induction (optional), and editing module (bulk liquid culture) 840. The cells are allowed to grow until they go through several to many doublings, then editing optionally is induced by induction of transcription of one or both of the nuclease and gRNA. In some embodiments, editing optionally is induced by transcription of one or both of the nuclease and the gRNA being under the control of an inducible promoter. In some embodiments, the inducible promoter is a pL promoter where the promoter is activated by a rise in temperature of the cell culture and "deactivated" by lowering the temperature of the cell culture.

The recovery, selection, isolation, growth, induction, editing and storage modules may all be separate, may be arranged and combined as shown in FIG. 8, or may be arranged or combined in other configurations. In certain embodiments, recovery and selection are performed in one module, and isolation, growth, induction, editing, and re-growth are performed in a separate module. Alternatively, recovery, selection, isolation, growth, induction, editing, and re-growth are performed in a single module.

Once the cells are edited and re-grown (e.g., recovered from editing), the cells may be stored, e.g., in a storage module 812, where the cells can be kept at, e.g., 4° C. until the cells are used in another round of editing, or the cells may be transferred to a reservoir for cell retrieval 814. The multi-module cell processing instrument is controlled by a processor 824 configured to operate the instrument based on user input, as directed by one or more scripts, or as a combination of user input or a script. The processor 824 may control the timing, duration, temperature, and operations of the various modules of the system 800 and the dispensing of reagents. For example, the processor 824 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Growth in the Cell Growth Module

Figure 9:
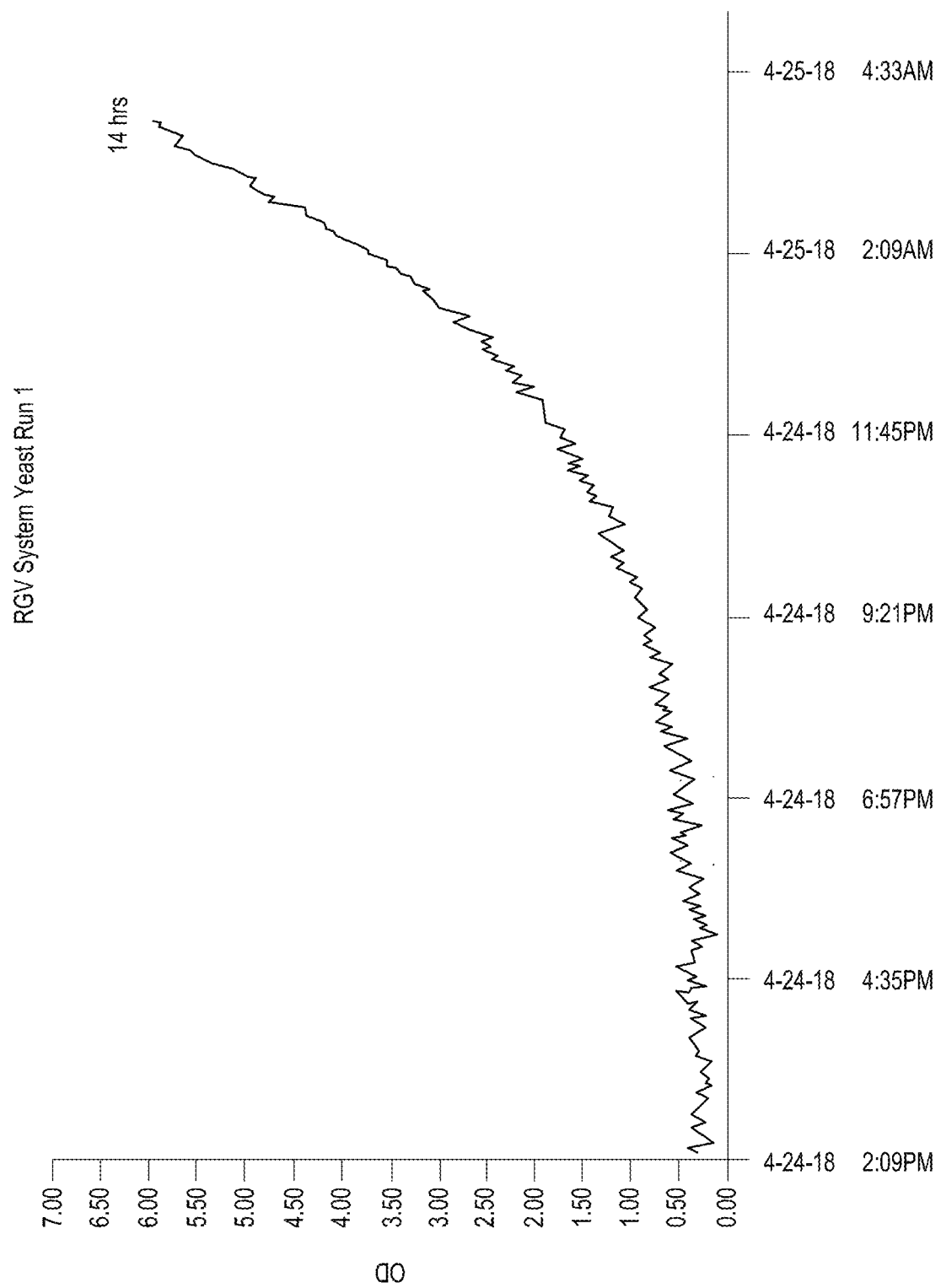
FIG. 9 is a graph demonstrating real-time monitoring of growth of S. cerevisiae str. s288c cell culture $OD_{600}$ employing the cell growth device as described in relation to FIGS. 3A-3D where a 2-paddle rotating growth vial was used.

One embodiment of the cell growth device as described herein was used to grow a yeast cell culture which was monitored in real time using an embodiment of the cell growth device described herein. The rotating growth vial/cell growth device was used to measure $OD_{600}$ in real time of yeast S. cerevisiae str. s288c cells in YPAD medium. The cells were grown at 30° C. using oscillating rotation and employing a 2-paddle rotating growth vial. FIG. 9 is a graph showing the results. Note that $OD_{600}$ 6.0 was reached in 14 hours.

Example II: Cell Concentration

Figure 10:
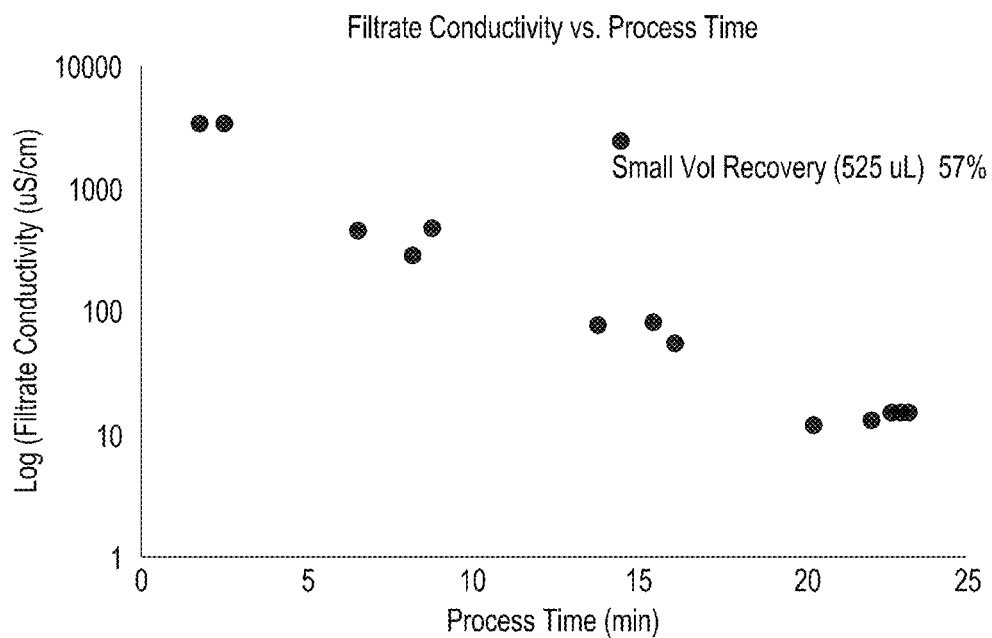
FIG. 10 is a graph plotting filtrate conductivity against filter processing time for a yeast culture processed in the cell concentration device/module described in relation to FIGS. 4A-4E.

The TFF module as described above in relation to FIGS. 4A-4E has been used successfully to process and perform buffer exchange on yeast cultures. A yeast culture was initially concentrated to approximately 5 ml using two passes through the TFF device in opposite directions. The cells were washed with 50 ml of 1M sorbitol three times, with three passes through the TFF device after each wash. After the third pass of the cells following the last wash with 1M sorbitol, the cells were passed through the TFF device two times, wherein the yeast cell culture was concentrated to approximately 525 µl. FIG. 10 presents the filter buffer exchange performance for yeast cells determined by measuring filtrate conductivity and filter processing time. Target conductivity (—10 µS/cm) was achieved in approximately 23 minutes utilizing three 50 ml 1M sorbitol washes and three passes through the TFF device for each wash. The volume of the cells was reduced from 20 ml to 525 µl. Recovery of approximately 90% of the cells has been achieved.

Example III: Production and Transformation of Electrocompetent S. Cerevisiae

For testing transformation of the FTEP device in yeast, electrocompetent S. Cerevisiae cells were created using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/–0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1M sorbitol. These steps were repeated three times for a total of three wash-spin-decant steps. The pellet was suspended in sorbitol to a final OD600 of 150+/–20 per ml.

A comparative electroporation experiment was performed to determine the efficiency of transformation of the electrocompetent S. cerevisiae using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 11:
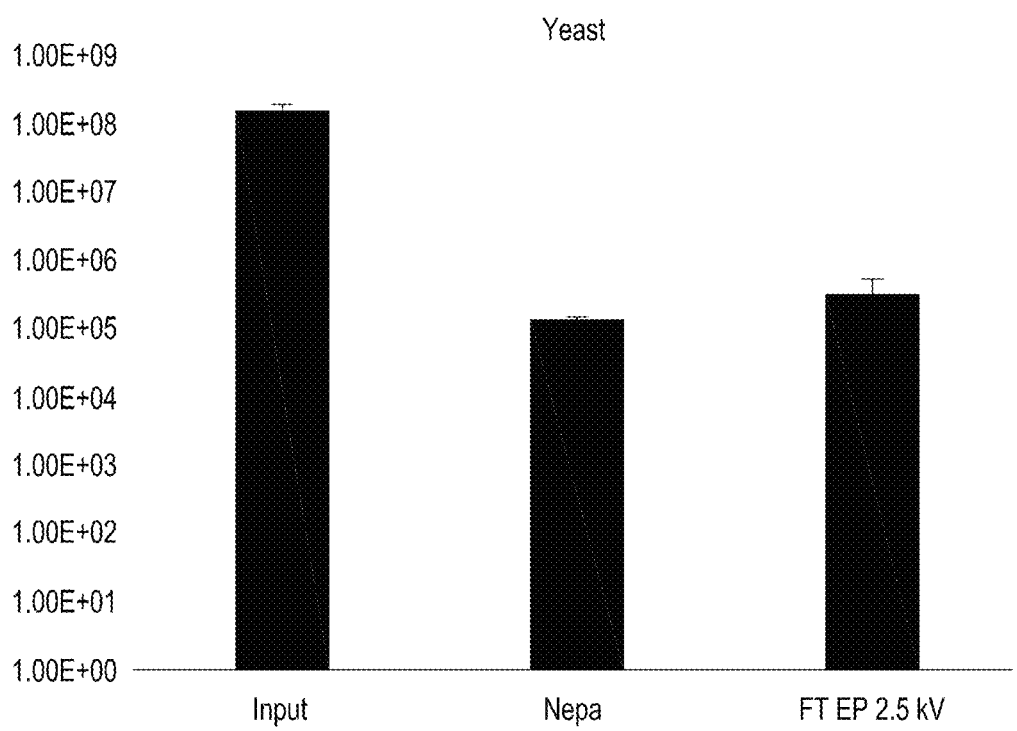
FIG. 11 is a bar graph showing the results of electroporation of S. cerevisiae str. s288c using an FTEP device as described in relation to FIGS. 5C-5G and a comparator electroporation method.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 11. The device showed better transformation and survival of electrocompetent S. cerevisiae at 2.5 kV voltages as compared to the NEPAGENE™ method. Input is total number of cells that were processed.

Example IV: Singulation of Yeast Colonies in a Solid Wall Device

Electrocompetent yeast cells were transformed with a cloned library, an isothermal assembled library, or a process control sgRNA plasmid (escapee surrogate). Electrocompetent Saccharomyces cerevisiae cells were prepared as follows: The afternoon before transformation was to occur, 10 mL of YPAD was inoculated with the selected Saccharomyces cerevisiae strain. The culture was shaken at 250 RPM and 30° C. overnight. The next day, 100 mL of YPAD was added to a 250-mL baffled flask and inoculated with the overnight culture (around 2 mL of overnight culture) until the OD600 reading reached 0.3+/–0.05. The culture was placed in the 30° C. incubator shaking at 250 RPM and allowed to grow for 4-5 hours, with the OD checked every hour. When the culture reached an OD600 of approximately 1.5, 50 mL volumes were poured into two 50 mL conical vials, then centrifuged at 4300 RPM for 2 minutes at room temperature. The supernatant was removed from all 50 mL conical tubes, while avoiding disturbing the cell pellet. 50 mL of a Lithium Acetate/Dithiothreitol solution was added to each conical tube and the pellet was gently resuspended. Both suspensions were transferred to a 250 mL flask and placed in the shaker; then shaken at 30° C. and 200 RPM for 30 minutes.

After incubation was complete, the suspension was transferred to two 50-mL conical vials. The suspensions then were centrifuged at 4300 RPM for 3 minutes, then the supernatant was discarded. Following the lithium acetate/Dithiothreitol treatment step, cold liquids were used and the cells were kept on ice until electroporation. 50 mL of 1M sorbitol was added and the pellet was resuspended, then centrifuged at 4300 RPM, 3 minutes, 4° C., after which the supernatant was discarded. The 1M sorbitol wash was repeated twice for a total of three washes. 50 µL of 1M sorbitol was added to one pellet, cells were resuspended, then transferred to the other tube to suspend the second pellet. The volume of the cell suspension was measured and brought to 1 mL with cold 1M sorbitol. At this point the cells were electrocompetent and could be transformed with a cloned library, an isothermal assembled library, or process control sgRNA plasmids.

In brief, a required number of 2-mm gap electroporation cuvettes were prepared by labeling the cuvettes and then chilling on ice. The appropriate plasmid or DNA mixture was added to each corresponding cuvette and placed back on ice. 100 uL of electrocompetent cells was transferred to each labelled cuvette, and each sample was electroporated using appropriate electroporator conditions. 900 uL of room temperature YPAD Sorbitol media was then added to each cuvette. The cell suspension was transferred to a 14 ml culture tube and then shaken at 30° C., 250 RPM for 3 hours. After a 3 hr recovery, 9 ml of YPAD containing the appropriate antibiotic, e.g., G418 or Hygromycin B, was added. At this point the transformed cells were processed in parallel in the solid wall device and the standard plating protocol, so as to compare "normalization" in the sold wall device with the standard benchtop process. Immediately before cells the cells were introduced to the permeable-bottom solid wall device, the 0.45 µM filter forming the bottom of the microwells was treated with a 0.1% TWEEN™ solution to effect proper spreading/distribution of the cells into the microwells of the solid wall device. The filters were placed into a Swinnex Filter Holder (47 mm, Millipore®, SX0004700) and 3 ml of a solution with 0.85% NaCl and 0.1% TWEEN™ was pulled through the solid wall device and filter through using a vacuum. Different TWEEN™ concentrations were evaluated, and it was determined that for a 47 mm diameter solid wall device with a 0.45 µM filter forming the bottom of the microwells, a pre-treatment of the solid wall device+filter with 0.1% TWEEN™ was preferred (data not shown).

At the end of the incubation the perforated disks and filters (still assembled) were removed from the supporting nutrient source (in this case an agar plate) and were photographed with a focused, "transilluminating" light source so that the number and distribution of loaded microwells on the solid wall device could be assessed (data not shown). To retrieve cells from the permeable-bottom solid wall device, the filter was transferred to a labeled sterile 100 mm petri dish which contained 15 ml of sterile 0.85% NaCl, then the petri dish was placed in a shaking incubator set to 30° C./80 RPM to gently remove the cells from the filter and resuspend the cells in the 0.85% NaCl. The cells were shaken for 15 minutes, then were transferred to a sterile tube, e.g., a 50 ml conical centrifuge tube. The OD600 of the cell suspension was measured; at this point the cells can be processed in different ways depending on the purpose of the study. For example, if an ADE2 stop codon mutagenesis library is used, successfully-edited cells should result in colonies with a red color phenotype when the resuspended cells are spread onto YPD agar plates and allowed to grow for 4-7 days. This phenotypic difference allows for a quantification of percentage of edited cells and the extent of normalization of edited and unedited cells.

Example V: Growth and Editing of *S. cerevisae* Under Selective Pressure

To compare the editing rate of yeast cells transformed with the vectors depicted in FIGS. 1C and 1D, as well as a "standard" vector without a degron fusion or minimal promoter, 10 mL of YPAD medium was inoculated with the IY19 strain of *S. cerevisiae*. The culture was incubated at 30° C. while shaking at 250 rpm overnight. The following day, the overnight culture was diluted to an OD600=0.3 in 100 ml in fresh YPAD media. The diluted culture was placed in the 30° C. incubator shaking at 250 rpm and grown for 4-5 hours. When the culture reached OD600 of ~1.5, cells were harvested by centrifuging at 4300 RPM for 3 minutes at room temperature.

The harvested cells were resuspended in 50 ml of 100 mM lithium acetate+10 mM DTT solution and conditioned by shaking at 30° C./200 rpm for 30 minutes. The cells were then harvested after conditioning by centrifuging at 4300 RPM for 3 minutes at room temperature. Following centrifugation, the cells were washed 3x with 50 mL of ice-cold 1M sorbitol; at the end of the final wash, cells were resuspended with 1ml of ice cold 1M sorbitol. 100 µl of the cell resuspension was used in every transformation (standard plasmid backbone, degron plasmid backbone (see FIG. 1C) and minimal promoter plasmid backbone (see FIG. 1D)). The editing cassettes were the same for each plasmid backbone. The competent cells were electroporated in a 2-mm electroporation cuvette along with the appropriate editing plasmid.

The plasmid backbone/cassette mix comprised 500 ng of linear plasmid backbone (standard, degron, and minimal promoter) and 50 ng of cassette. A Nepagene electroporator used the following conditions to electroporate each sample: for the poring pulse: a single pulse at voltage=1800, pulse length=5.0, pulse interval=50.0 msec; for the transfer pulses, three pulses at voltage=100, pulse length=50.0 msec, pulse interval–50.0. Following electroporation, 900 µL of room temperature YPAD+1M Sorbitol media was added to each cuvette and the cell suspension was transferred to a pop-cap 15 mL tube. This mix was shaken at 30° C./250 RPM for 3 hours. 1-10 µl of the transformation was then plated on YPD+G418 (200 µg/ml) plates and incubated at 30° C. for 3 days. 96 colonies were picked from transformation plates, and these colonies were cultured in 1 mL of YPAD+G418 (200 µg/ml) media in a deep-well plate and grown overnight at 30° C. The 96-well plate was used for DNA extraction using a SV lysis Promega DNA extraction kit (Promega, Madison, Wis.) according to manufacturer's instructions.

Figure 12A:
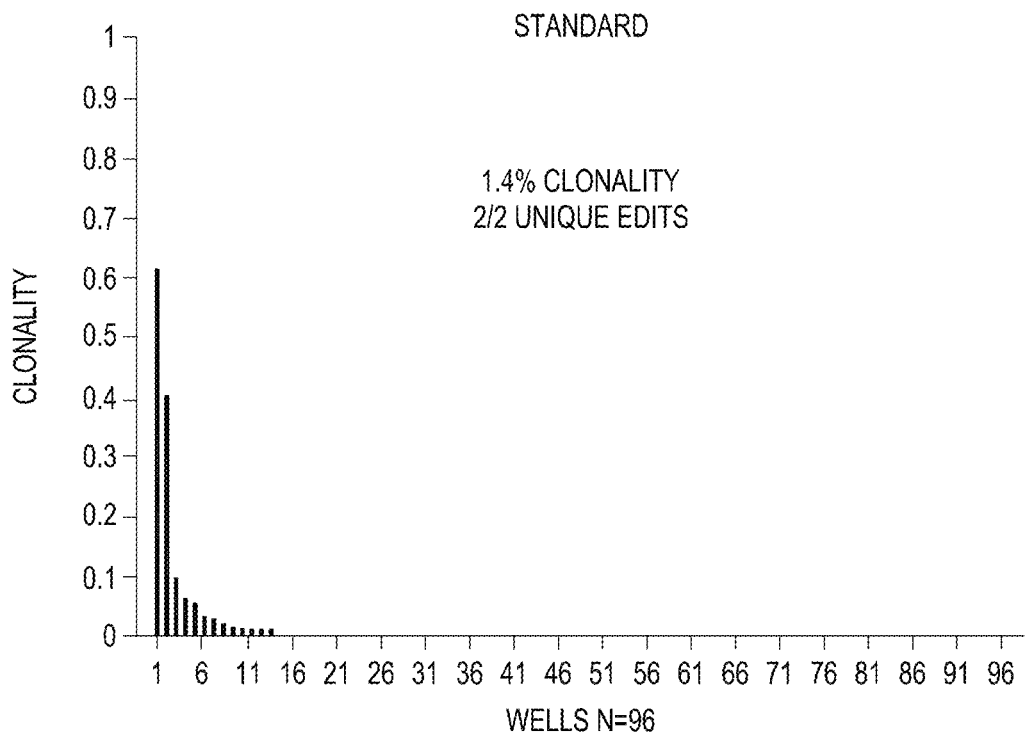
FIGS. 12A-12C comprise three graphs comparing the editing clonality obtained using a yeast editing vector with an unmodified hygromycin resistance gene, a degron-fused hygromycin resistance gene, and a hygromycin resistance gene under the control of a minimal promoter.
Figure 12B:
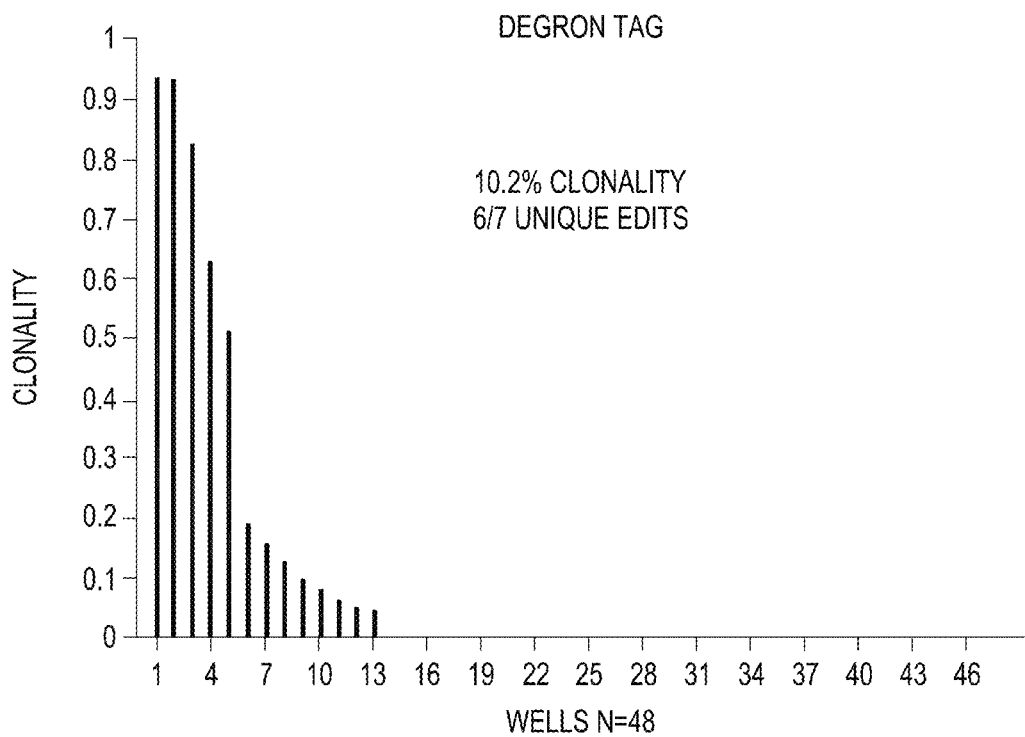
Figure 12C:
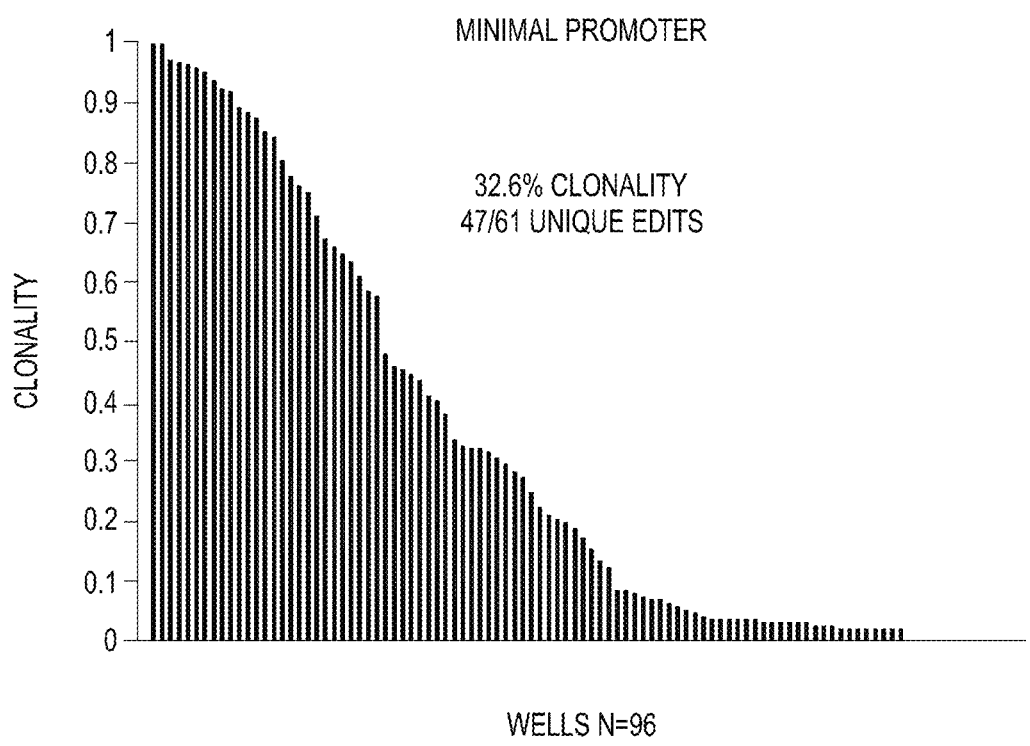
Figure 13A:
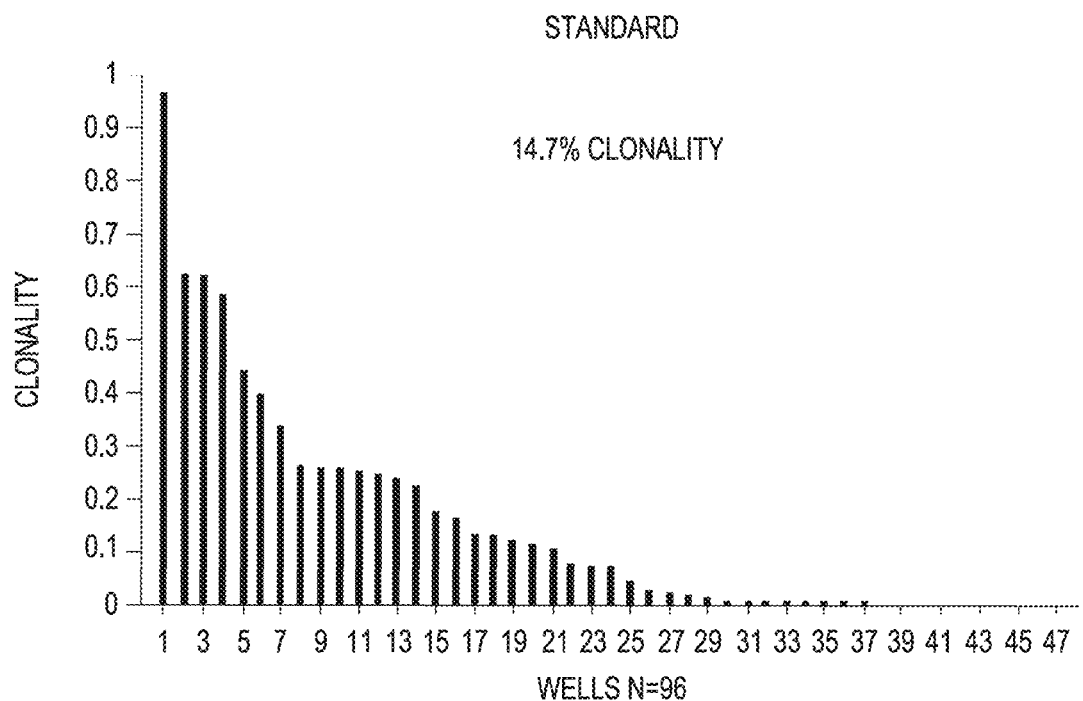
FIGS. 13A-13C comprise three graphs comparing the editing clonality obtained using a yeast editing vector with an unmodified G418 resistance gene, a degron-fused G418 resistance gene, and G418 resistance gene under the control of a minimal promoter.
Figure 13B:
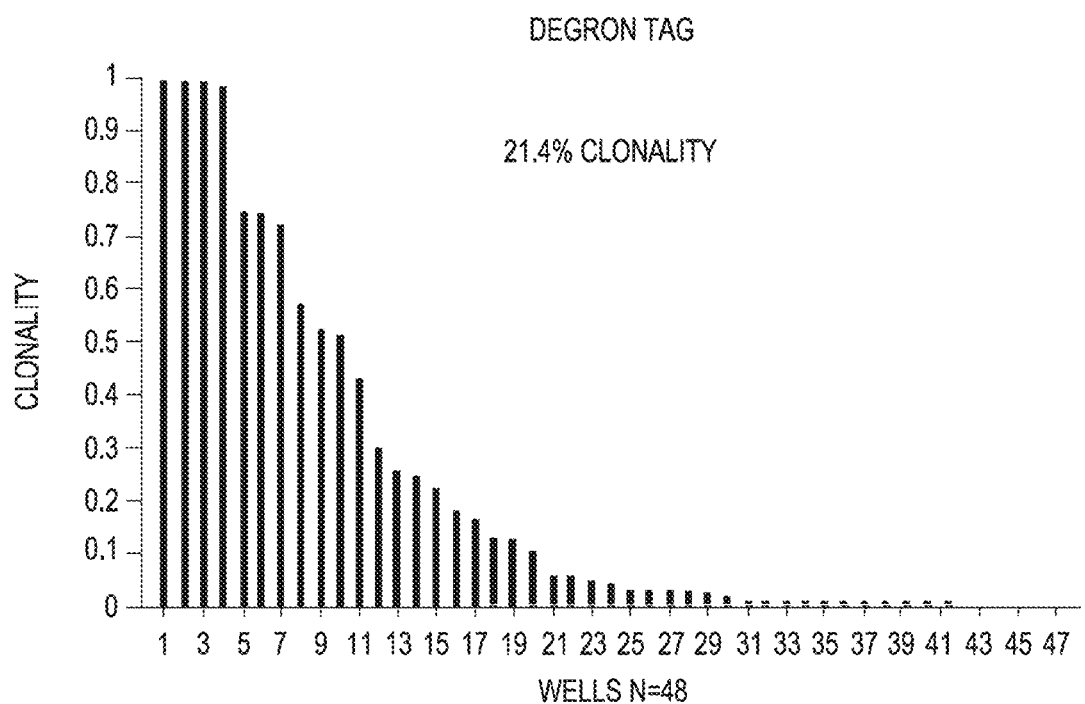
Figure 13C:
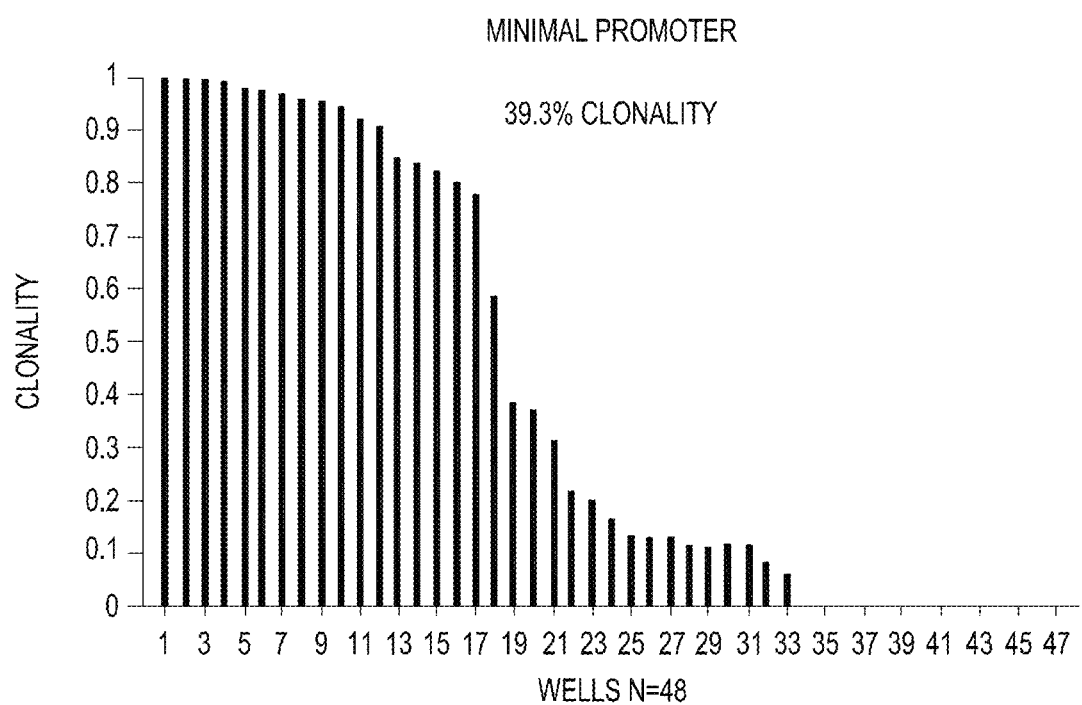

Three different survival marker proteins were tested: hygromycin (FIGS. 12A, 12B and 12C), kanamycin (FIGS. 13A, 13B, and 13C), and blasticidin (data not shown). The minimal promoter was the truncated version of the URA3 promoter, URA3-d, comprising only 47 nucleotides located upstream of the start codon. Using hygromycin as the survival marker, the standard editing plasmid resulted in clonality of 1.4%, the plasmid coding for the degron-hygromycin fusion protein resulted in clonality of 10.2%, and the plasmid with the minimal promoter driving transcription of the hygromycin gene resulted in 32.6% clonality. Using kanamycin as the survival marker, the standard editing plasmid resulted in clonality of 14.7%, the plasmid coding for the degron-kanamycin fusion protein resulted in clonality of 21.4%, and the plasmid with the minimal promoter driving transcription of the kanamycin gene resulted in 39.3% clonality. Preliminary data with the minimal promoter driving transcription of blasticidin as the survival marker, the clonality was 6.9% with 19/20 unique edits (data not shown).

Example VI: Growth and Editing of *S. cerevisae* Under Selective Pressure

Figure 14:
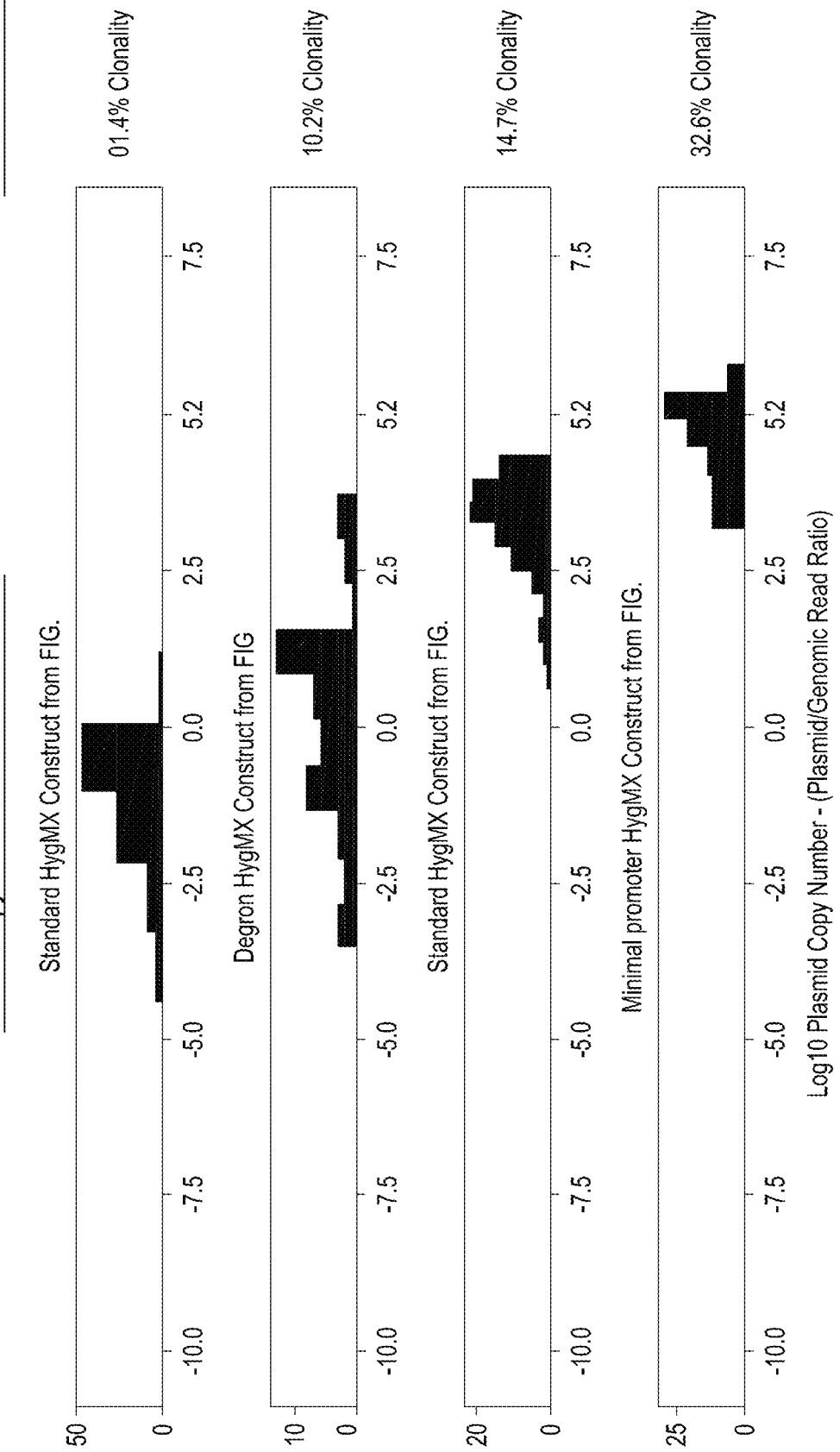
FIG. 14 shows plasmid copy number and edit rate of various plasmid constructs and their edit rates.

FIG. 14 shows the plasmid copy number and edit rate of various plasmid constructs and their edit rates measured via shotgun NGS sequencing. The plasmid copy number is calculated by taking the ratio of median plasmid read depth vs. median genomic read depth. The histograms show the measured plasmid copy number from at least 48 isolated colonies. The edit rates were calculated via next gen sequencing of isolated colonies and are the same values that appear in FIGS. 12 A-12C and FIGS. 13A-13C. Note the correlation between plasmid copy number and observed edit rate, which illustrates the utility of increasing the plasmid copy number of editing constructs to increase observed editing.

Example VII: Fully-Automated Singleplex RGN-directed Editing Run

Singleplex automated genomic editing using MAD7 nuclease was successfully performed with an automated multi-module instrument of the disclosure. An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. Coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example VIII: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. Coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in an isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶16.

We claim:

1. A method for performing editing in yeast comprising:
providing a population of yeast cells;
transforming the population of yeast cells with a population of editing vectors, wherein each editing vector comprises: a yeast 2μ backbone; a 2μ origin of replication; a first non-minimal or non-core constitutive promoter driving transcription of a gRNA sequence and donor DNA sequence with followed by a terminator element 3' to the gRNA and donor DNA sequences; a second non-minimal or non-core constitutive promoter driving transcription of a coding sequence for a degron-survival marker fusion gene followed by a terminator element 3' to the degron-survival marker fusion gene; a third non-minimal or non-core constitutive promoter driving transcription of a nuclease coding sequence with a terminator element 5' to the nuclease coding sequence; and an origin of replication for propagation of the editing vector in bacteria;
growing the transformed yeast cells in selective medium to select for cells expressing a degron-survival marker fusion protein;
providing conditions to allow the transformed yeast cells to edit nucleic acid sequences in the yeast cells; and
growing the edited yeast cells.

2. The method of claim 1, wherein the degron is an ubiquitin-dependent degron.

3. The method of claim 1, wherein the degron is selected from Ura3-d degon, Ubi-R degron, Ubi-M degron, Ubi-Q degron, Ubi-E degron, ZF1 degron, C-terminal phosphodegron; Ts-degron; lt-degron; auxin inducible degron; DD-degron, LID-degron; PSD degron, B-LID degron; and a TIPI degron.

4. The method of claim 3, wherein the degron is the Ura3-d degron.

5. The method of claim 1, wherein the survival marker is selected from the group of hygromycin, blasticidin, kanamycin, and nourseothricin.

6. The method of claim 1, wherein the first, second and third constitutive promoters are the same constitutive promoter.

7. The method of claim 1, wherein two of the first, second and third constitutive promoters are different constitutive promoters.

8. The method of claim 1, wherein all of the first, second and third constitutive promoters are different constitutive promoters.

9. A method for performing editing in yeast comprising:
providing a population of yeast cells;
transforming the population of yeast cells with a population of editing vectors, wherein each editing vector comprises: a yeast 2μ backbone; a 2μ origin of replication; a first non-minimal or non-core constitutive promoter driving transcription of a gRNA sequence and donor DNA sequence with followed by a terminator element 3' to the gRNA and donor DNA sequences; a minimal or weak promoter driving transcription of a coding sequence for a survival marker gene followed by a terminator element 3' to the survival marker gene; a second non-minimal or non-core constitutive promoter driving transcription of a nuclease coding sequence with a terminator element 5' to the nuclease coding sequence; and an origin of replication for propagation of the editing vector in bacteria;
growing the transformed yeast cells in selective medium to select for cells expressing a survival marker protein;
providing conditions to allow the transformed yeast cells to edit nucleic acid sequences in the yeast cells; and
growing the edited yeast cells.

10. The method of claim 9, wherein if the minimal or weak promoter driving transcription of a coding sequence for a survival marker gene is a minimal promoter, the minimal promoter is selected from a URA3-d promoter, a pHIS3 promoter, a pTRP1 promoter, a pLEU2 promoter, a pURA3 promoter, a pTEF1 promoter, and a pHXT7 promoter.

11. The method of claim 10, wherein the minimal or weak promoter driving transcription of the coding sequence for a survival marker gene is a URA3-d promoter.

12. The method of claim 9, wherein if the minimal or weak promoter driving transcription of a coding sequence for a survival marker gene is a weak promoter, the weak promoter is selected from a pSSA1 promoter, a pPDA1 promoter, a pCYC1 promoter, a pTPS1 promoter, and a pSSB1 promoter.

13. The method of claim 9, wherein the survival marker is selected from the group of hygromycin, blasticidin, kanamycin, and nourseothricin.

14. The method of claim 9, wherein the first and second constitutive promoters are the same constitutive promoter.

15. The method of claim 9, wherein the first and second constitutive promoters are different constitutive promoters.

* * * * *